(12) United States Patent
Xu et al.

(10) Patent No.: US 11,813,485 B2
(45) Date of Patent: Nov. 14, 2023

(54) SYSTEMS AND METHODS FOR HISTOTRIPSY IMMUNOSENSITIZATION

(71) Applicants: The Regents of the University of Michigan, Ann Arbor, MI (US); The United States Government as represented by the Department of Veterans Affairs, Washington, DC (US)

(72) Inventors: Zhen Xu, Ann Arbor, MI (US); Clifford Suhyun Cho, Ann Arbor, MI (US)

(73) Assignees: The Regents of the University of Michigan, Ann Arbor, MI (US); The United States Government as represented by the Department of Veterans Affairs, Washington, DC (US)

( * ) Notice: Subject to any disclaimer, the term of this patent is extended or adjusted under 35 U.S.C. 154(b) by 164 days.

(21) Appl. No.: 17/161,498

(22) Filed: Jan. 28, 2021

(65) Prior Publication Data
US 2021/0252313 A1    Aug. 19, 2021

Related U.S. Application Data

(60) Provisional application No. 62/966,960, filed on Jan. 28, 2020.

(51) Int. Cl.
*A61N 7/00* (2006.01)
*A61K 39/00* (2006.01)
*A61B 10/00* (2006.01)

(52) U.S. Cl.
CPC ............ *A61N 7/00* (2013.01); *A61K 39/0011* (2013.01); *A61B 10/0045* (2013.01)

(58) Field of Classification Search
CPC .... A61N 7/00; A61N 7/02; A61N 2007/0039; A61K 39/0011; A61B 10/0045;
(Continued)

(56) References Cited

U.S. PATENT DOCUMENTS

| 3,243,497 A | 3/1966 | Kendall et al. |
| 3,679,021 A | 7/1972 | Goldberg et al. |

(Continued)

FOREIGN PATENT DOCUMENTS

| AU | 2017222925 B2 | 11/2021 |
| BR | 112018017326 B1 | 12/2022 |

(Continued)

OTHER PUBLICATIONS

Qu et al., "Non-thermal histotripsy tumor ablation promotes abscopal immune responses that enhance cancer immunotherapy", Jan. 15, 2020, Journal for ImmunoTherapy of Cancer, v.8(1):e000200. (Year: 2020).*

(Continued)

*Primary Examiner* — Christopher Koharski
*Assistant Examiner* — Taylor Deutsch
(74) *Attorney, Agent, or Firm* — Shay Glenn LLP

(57) ABSTRACT

Systems and methods for histotripsy and immunotherapy are provided. In some embodiments, histotripsy can be applied to a target tissue volume to lyse and solubilize the target tissue volume to release tumor antigens. In some embodiments, an immune response of the treatment can be evaluated. In other embodiments, an immune therapy can be applied after applying the histotripsy. In one embodiment, the lysed and solubilized cells can be extracted from the tissue. The extracted cells can be used to create immune therapies, including vaccines.

25 Claims, 15 Drawing Sheets

(58) Field of Classification Search
CPC .......... A61B 2560/0437; A61B 5/0036; A61B 10/0233; A61B 34/30; A61B 90/50; A61B 2090/3762; A61B 2090/374; A61B 2090/378

See application file for complete search history.

(56) References Cited

U.S. PATENT DOCUMENTS

| | | |
|---|---|---|
| 3,879,699 A | 4/1975 | Pepper |
| 4,016,749 A | 4/1977 | Wachter |
| 4,024,501 A | 5/1977 | Herring et al. |
| 4,051,394 A | 9/1977 | Tieden |
| 4,117,446 A | 9/1978 | Alais |
| 4,266,747 A | 5/1981 | Souder, Jr. et al. |
| 4,269,174 A | 5/1981 | Adair |
| 4,277,367 A | 7/1981 | Madsen et al. |
| 4,351,038 A | 9/1982 | Alais |
| 4,406,153 A | 9/1983 | Ophir et al. |
| 4,440,025 A | 4/1984 | Hayakawa et al. |
| 4,447,031 A | 5/1984 | Souder, Jr. et al. |
| 4,453,408 A | 6/1984 | Clayman |
| 4,483,343 A | 11/1984 | Beyer et al. |
| 4,483,345 A | 11/1984 | Miwa |
| 4,548,374 A | 10/1985 | Thompson et al. |
| 4,549,533 A | 10/1985 | Cain et al. |
| 4,550,606 A | 11/1985 | Drost |
| 4,551,794 A | 11/1985 | Sandell |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,938,217 A | 7/1990 | Lele |
| 4,957,099 A | 9/1990 | Hassler |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,078,140 A | 1/1992 | Kwoh |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,174,294 A | 12/1992 | Saito et al. |
| 5,209,221 A | 5/1993 | Riedlinger |
| 5,215,680 A | 6/1993 | D'Arrigo |
| 5,219,401 A | 6/1993 | Cathignol et al. |
| 5,222,806 A | 6/1993 | Roberts |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,393,296 A | 2/1995 | Rattner |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,450,305 A | 9/1995 | Boys et al. |
| 5,469,852 A | 11/1995 | Nakamura et al. |
| 5,474,071 A | 12/1995 | Chapelon et al. |
| 5,474,531 A | 12/1995 | Carter |
| 5,490,051 A | 2/1996 | Messana |
| 5,492,126 A | 2/1996 | Hennige et al. |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,646,098 A | 7/1997 | Porter |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,694,936 A | 12/1997 | Fujimoto et al. |
| 5,695,460 A | 12/1997 | Siegel et al. |
| 5,717,657 A | 2/1998 | Ruffa |
| 5,720,287 A | 2/1998 | Chapelon et al. |
| 5,724,972 A | 3/1998 | Petrofsky |
| 5,743,863 A | 4/1998 | Chapelon |
| 5,753,929 A | 5/1998 | Bliss |
| 5,759,162 A | 6/1998 | Oppelt et al. |
| 5,766,138 A | 6/1998 | Rattner |
| 5,769,790 A | 6/1998 | Watkins et al. |
| 5,797,848 A | 8/1998 | Marian et al. |
| 5,820,623 A | 10/1998 | Ng |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,928,169 A | 7/1999 | Schitzle et al. |
| 5,932,807 A | 8/1999 | Mallart |
| 5,947,904 A | 9/1999 | Hossack et al. |
| 6,001,069 A | 12/1999 | Tachibana et al. |
| 6,022,309 A | 2/2000 | Celliers et al. |
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,165,144 A | 12/2000 | Talish et al. |
| 6,176,842 B1 | 1/2001 | Tachibana et al. |
| 6,296,619 B1 | 10/2001 | Brisken et al. |
| 6,308,585 B1 | 10/2001 | Nilsson et al. |
| 6,308,710 B1 | 10/2001 | Silva |
| 6,309,355 B1 | 10/2001 | Cain et al. |
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |

(56) References Cited

U.S. PATENT DOCUMENTS

| | | |
|---|---|---|
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugham, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckal et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,175,599 B2 | 2/2007 | Hynynen et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,429,249 B1 | 9/2008 | Winder et al. |
| 7,431,704 B2 | 10/2008 | Babaev |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 7,695,437 B2 | 4/2010 | Quistgaard et al. |
| 7,714,481 B2 | 5/2010 | Sakai |
| 7,771,359 B2 | 8/2010 | Adam |
| 7,967,763 B2 | 6/2011 | Deem et al. |
| 8,057,408 B2 | 11/2011 | Cain et al. |
| 8,295,912 B2 | 10/2012 | Gertner |
| 8,333,115 B1 | 12/2012 | Garvey et al. |
| 8,337,407 B2 | 12/2012 | Quistgaard et al. |
| 8,342,467 B2 | 1/2013 | Stachowski et al. |
| 8,376,970 B2 | 2/2013 | Babaev |
| 8,539,813 B2 | 9/2013 | Cain et al. |
| 8,568,339 B2 | 10/2013 | Rybyanets |
| 8,636,664 B2 | 1/2014 | Brannan |
| 8,715,187 B2 | 5/2014 | Landberg Davis et al. |
| 8,845,537 B2 | 9/2014 | Tanaka et al. |
| 8,932,239 B2 | 1/2015 | Sokka et al. |
| 9,028,434 B2 | 5/2015 | Tanaka |
| 9,049,783 B2 | 6/2015 | Teofilovic |
| 9,061,131 B2 | 6/2015 | Jahnke et al. |
| 9,144,694 B2 | 9/2015 | Cain |
| 9,220,476 B2 | 12/2015 | Coussios et al. |
| 9,228,730 B1 | 1/2016 | Inbody |
| 9,302,124 B2 | 4/2016 | Konofagou et al. |
| 9,457,201 B2 | 10/2016 | Hoelscher et al. |
| 9,526,923 B2 | 12/2016 | Jahnke et al. |
| 9,636,133 B2 | 5/2017 | Hall et al. |
| 9,642,634 B2 | 5/2017 | Cain et al. |
| 9,763,688 B2 | 9/2017 | Stulen et al. |
| 9,901,753 B2 | 2/2018 | Cain et al. |
| 9,943,708 B2 | 4/2018 | Roberts et al. |
| 10,022,107 B2 | 7/2018 | Thornton et al. |
| 10,046,181 B2 | 8/2018 | Barthe et al. |
| 10,058,352 B2 | 8/2018 | Carvell et al. |
| 10,071,266 B2 | 9/2018 | Cain |
| 10,130,828 B2 | 11/2018 | Vortman et al. |
| 10,219,815 B2 | 3/2019 | Maxwell et al. |
| 10,293,187 B2 | 5/2019 | Cannata et al. |
| 10,751,015 B2 | 8/2020 | Anderson et al. |
| 10,751,125 B2 | 8/2020 | Levy et al. |
| 10,765,892 B1 | 9/2020 | Vitek et al. |
| 10,780,298 B2 | 9/2020 | Cain et al. |
| 10,791,991 B2 | 10/2020 | Burkett et al. |
| 10,799,209 B2 | 10/2020 | Lahti et al. |
| 10,806,421 B2 | 10/2020 | Keller |
| 10,820,813 B2 | 11/2020 | Alpert |
| 10,847,264 B2 | 11/2020 | Mansker et al. |
| 10,849,511 B2 | 12/2020 | Tochterman et al. |
| 10,869,603 B2 | 12/2020 | Millett et al. |
| 10,869,633 B2 | 12/2020 | Burkett |
| 10,869,648 B2 | 12/2020 | Hubbard et al. |
| 10,874,353 B2 | 12/2020 | Assif |
| 10,874,409 B2 | 12/2020 | Matsubara et al. |
| 10,878,586 B2 | 12/2020 | Brokman et al. |
| 10,888,232 B2 | 1/2021 | Anderson et al. |
| 10,893,808 B2 | 1/2021 | Dorando |
| 10,900,933 B2 | 1/2021 | Prus et al. |
| 10,905,394 B2 | 2/2021 | Stigall et al. |
| 10,912,463 B2 | 2/2021 | Davies et al. |
| 10,925,688 B2 | 2/2021 | Millett et al. |
| 10,927,003 B2 | 2/2021 | Millett et al. |
| 10,932,678 B2 | 3/2021 | Burkett |
| 10,939,826 B2 | 3/2021 | Glynn et al. |
| 10,942,022 B2 | 3/2021 | Johansson et al. |
| 10,973,419 B2 | 4/2021 | Corl |
| 10,993,618 B2 | 5/2021 | Mansker et al. |
| 10,993,628 B2 | 5/2021 | Tochterman |
| 10,993,694 B2 | 5/2021 | Meyer et al. |
| 11,000,185 B2 | 5/2021 | Stigall et al. |
| 11,006,840 B2 | 5/2021 | Stigall |
| 11,013,491 B2 | 5/2021 | Rice et al. |
| 11,020,087 B2 | 6/2021 | Hoffman |
| 11,020,089 B2 | 6/2021 | Corl |
| 11,026,591 B2 | 6/2021 | Burkett et al. |
| 11,040,140 B2 | 6/2021 | Unser et al. |
| 11,071,522 B2 | 7/2021 | Hynynen et al. |
| 11,103,731 B2 | 8/2021 | Vortman et al. |
| 11,112,473 B2 | 9/2021 | Assif |
| 11,119,552 B2 | 9/2021 | Spencer et al. |
| 11,120,896 B2 | 9/2021 | Balignasay et al. |
| 11,123,019 B2 | 9/2021 | Merritt et al. |
| 11,123,575 B2 | 9/2021 | Vortman et al. |
| 11,141,063 B2 | 10/2021 | Kemp et al. |
| 11,141,131 B2 | 10/2021 | Stigall et al. |
| 11,160,513 B2 | 11/2021 | Anderson et al. |
| 11,205,507 B2 | 12/2021 | Anderson et al. |
| 11,219,748 B2 | 1/2022 | Burkett et al. |
| 11,224,349 B2 | 1/2022 | Davies et al. |
| 11,224,403 B2 | 1/2022 | Corl |
| 11,224,407 B2 | 1/2022 | Wrolstad et al. |

(56) References Cited

U.S. PATENT DOCUMENTS

| | | |
|---|---|---|
| 11,234,649 B2 | 2/2022 | Matsubara et al. |
| 11,246,533 B2 | 2/2022 | Henderson et al. |
| 11,246,565 B2 | 2/2022 | Corl |
| 11,253,225 B2 | 2/2022 | Hancock et al. |
| 11,260,160 B2 | 3/2022 | Matsubara et al. |
| 11,272,845 B2 | 3/2022 | Cheline et al. |
| 11,272,904 B2 | 3/2022 | Vortman et al. |
| 11,291,866 B2 | 4/2022 | Levy et al. |
| 11,298,030 B2 | 4/2022 | Davies et al. |
| 11,309,071 B2 | 4/2022 | Anderson |
| 11,311,271 B2 | 4/2022 | Stigall et al. |
| 11,324,410 B2 | 5/2022 | Burkett |
| 11,350,954 B2 | 6/2022 | De Cicco et al. |
| 11,369,346 B2 | 6/2022 | De Cicco et al. |
| 11,369,994 B2 | 6/2022 | Greenberg et al. |
| 11,395,638 B2 | 7/2022 | Shin et al. |
| 11,406,334 B2 | 8/2022 | Merritt |
| 11,406,355 B2 | 8/2022 | Hoffman et al. |
| 11,406,498 B2 | 8/2022 | Stigall et al. |
| 11,408,987 B2 | 8/2022 | Vignon et al. |
| 11,413,017 B2 | 8/2022 | Stigall et al. |
| 11,419,580 B2 | 8/2022 | Stigall et al. |
| 11,426,140 B2 | 8/2022 | Sudol et al. |
| 11,432,795 B2 | 9/2022 | Merritt |
| 11,446,000 B2 | 9/2022 | Minas et al. |
| 11,452,496 B2 | 9/2022 | Minas et al. |
| 11,452,506 B2 | 9/2022 | Perez et al. |
| 11,471,215 B2 | 10/2022 | Stigall et al. |
| 11,484,294 B2 | 11/2022 | Hancock et al. |
| 11,510,632 B2 | 11/2022 | Begin et al. |
| 11,517,291 B2 | 12/2022 | Kantor et al. |
| 11,520,874 B2 | 12/2022 | Kennedy et al. |
| 11,527,001 B2 | 12/2022 | Brokman et al. |
| 11,547,389 B2 | 1/2023 | Shin et al. |
| 11,553,889 B2 | 1/2023 | Spencer et al. |
| 11,554,386 B2 | 1/2023 | Pernot et al. |
| 11,559,207 B2 | 1/2023 | Stigall et al. |
| 11,576,649 B2 | 2/2023 | Corl |
| 11,576,652 B2 | 2/2023 | De Cicco et al. |
| 11,583,193 B2 | 2/2023 | Groenland et al. |
| 11,589,835 B2 | 2/2023 | Stigall et al. |
| 11,596,351 B2 | 3/2023 | Nair |
| 11,596,384 B2 | 3/2023 | Nair et al. |
| 11,596,387 B2 | 3/2023 | Song |
| 11,596,389 B2 | 3/2023 | Nair |
| 11,596,469 B2 | 3/2023 | Nair |
| 11,622,746 B2 | 4/2023 | Minas et al. |
| 11,638,576 B2 | 5/2023 | Groenland et al. |
| 11,647,989 B2 | 5/2023 | Hope Simpson et al. |
| 11,653,895 B2 | 5/2023 | Stigall et al. |
| 11,660,070 B2 | 5/2023 | Stigall et al. |
| 11,666,245 B2 | 6/2023 | Rajguru et al. |
| 11,666,307 B2 | 6/2023 | Unser |
| 11,672,433 B2 | 6/2023 | Park et al. |
| 11,672,552 B2 | 6/2023 | Pasquino et al. |
| 11,672,953 B2 | 6/2023 | May |
| 11,684,342 B2 | 6/2023 | Groenland et al. |
| 11,684,807 B2 | 6/2023 | Vortman et al. |
| 11,707,207 B2 | 7/2023 | Stigall et al. |
| 11,707,254 B2 | 7/2023 | Di Tullio et al. |
| 11,733,881 B2 | 8/2023 | Perez |
| 11,737,728 B2 | 8/2023 | Davies et al. |
| 11,744,527 B2 | 9/2023 | Scott et al. |
| 11,744,547 B2 | 9/2023 | Hynynen |
| 2001/0039420 A1 | 11/2001 | Burbank et al. |
| 2001/0041163 A1 | 11/2001 | Sugita et al. |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2002/0145091 A1 | 10/2002 | Talish et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0169591 A1 | 9/2003 | Cochran |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0162571 A1 | 8/2004 | Rabiner et al. |
| 2004/0236248 A1 | 11/2004 | Svedman |
| 2004/0243021 A1 | 12/2004 | Murphy et al. |
| 2004/0260214 A1 | 12/2004 | Echt et al. |
| 2005/0020945 A1 | 1/2005 | Tosaya et al. |
| 2005/0038339 A1 | 2/2005 | Chauhan et al. |
| 2005/0038361 A1 | 2/2005 | Zhong et al. |
| 2005/0152561 A1 | 7/2005 | Spencer |
| 2005/0154314 A1 | 7/2005 | Quistgaard |
| 2005/0154431 A1 | 7/2005 | Quistgaard et al. |
| 2005/0203399 A1 | 9/2005 | Vaezy et al. |
| 2005/0215901 A1 | 9/2005 | Anderson et al. |
| 2005/0234438 A1 | 10/2005 | Mast et al. |
| 2005/0283098 A1 | 12/2005 | Conston et al. |
| 2006/0060991 A1 | 3/2006 | Holsteyns et al. |
| 2006/0074303 A1 | 4/2006 | Chomenky et al. |
| 2006/0089636 A1 | 4/2006 | Christopherson et al. |
| 2006/0173321 A1 | 8/2006 | Kubota et al. |
| 2006/0173387 A1 | 8/2006 | Hansmann et al. |
| 2006/0206028 A1 | 9/2006 | Lee et al. |
| 2006/0241466 A1 | 10/2006 | Ottoboni et al. |
| 2006/0241523 A1 | 10/2006 | Sinelnikov et al. |
| 2006/0241533 A1 | 10/2006 | Geller |
| 2006/0264760 A1 | 11/2006 | Liu et al. |
| 2006/0293598 A1 | 12/2006 | Fraser |
| 2006/0293630 A1 | 12/2006 | Manna et al. |
| 2007/0010805 A1 | 1/2007 | Fedewa et al. |
| 2007/0016039 A1 | 1/2007 | Vortman et al. |
| 2007/0044562 A1 | 3/2007 | Sarr |
| 2007/0065420 A1 | 3/2007 | Johnson |
| 2007/0083120 A1 | 4/2007 | Cain et al. |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2007/0239001 A1 | 10/2007 | Mehl et al. |
| 2008/0013593 A1 | 1/2008 | Kawabata |
| 2008/0033297 A1 | 2/2008 | Sliwa |
| 2008/0033417 A1 | 2/2008 | Nields et al. |
| 2008/0051656 A1 | 2/2008 | Vaezy et al. |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0154132 A1 | 6/2008 | Hall et al. |
| 2008/0167555 A1 | 7/2008 | Qian et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0312561 A1 | 12/2008 | Chauhan |
| 2008/0319376 A1 | 12/2008 | Wilcox et al. |
| 2009/0030339 A1 | 1/2009 | Cheng et al. |
| 2009/0036773 A1 | 2/2009 | Lau et al. |
| 2009/0112098 A1 | 4/2009 | Vaezy et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2009/0254008 A1* | 10/2009 | Shields, Jr. ............... A61N 7/00 601/3 |
| 2009/0287083 A1 | 11/2009 | Kushculey et al. |
| 2010/0011845 A1 | 1/2010 | Laugham et al. |
| 2010/0056924 A1 | 3/2010 | Powers |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2010/0261994 A1 | 10/2010 | Davalos et al. |
| 2010/0274136 A1 | 10/2010 | Cerofolini |
| 2010/0286519 A1 | 11/2010 | Lee et al. |

(56) References Cited

U.S. PATENT DOCUMENTS

| | | |
|---|---|---|
| 2010/0298744 A1 | 11/2010 | Altshuler et al. |
| 2010/0305432 A1 | 12/2010 | Duhay et al. |
| 2010/0317971 A1 | 12/2010 | Fan et al. |
| 2010/0318002 A1 | 12/2010 | Prus et al. |
| 2011/0112400 A1 | 5/2011 | Emery et al. |
| 2011/0118602 A1 | 5/2011 | Weng et al. |
| 2011/0144490 A1 | 6/2011 | Davis et al. |
| 2011/0144545 A1 | 6/2011 | Fan et al. |
| 2011/0172529 A1 | 7/2011 | Gertner |
| 2011/0178444 A1 | 7/2011 | Slayton et al. |
| 2011/0245671 A1 | 10/2011 | Sato |
| 2011/0251528 A1 | 10/2011 | Canney et al. |
| 2011/0257524 A1 | 10/2011 | Gertner |
| 2011/0263967 A1 | 10/2011 | Bailey et al. |
| 2011/0270136 A1 | 11/2011 | Vitek et al. |
| 2011/0319927 A1 | 12/2011 | Nita |
| 2012/0029337 A1 | 2/2012 | Aoyagi |
| 2012/0029353 A1 | 2/2012 | Slayton et al. |
| 2012/0029393 A1 | 2/2012 | Lee |
| 2012/0059264 A1 | 3/2012 | Hope Simpson et al. |
| 2012/0059285 A1 | 3/2012 | Soltani et al. |
| 2012/0092724 A1 | 4/2012 | Pettis |
| 2012/0111339 A1 | 5/2012 | Barthe et al. |
| 2012/0130288 A1 | 5/2012 | Holland et al. |
| 2012/0136279 A1 | 5/2012 | Tanaka et al. |
| 2012/0158013 A1 | 6/2012 | Stefanchik et al. |
| 2012/0172720 A1 | 7/2012 | Asami et al. |
| 2012/0189998 A1 | 7/2012 | Kruecker et al. |
| 2012/0215157 A1 | 8/2012 | Berryman et al. |
| 2012/0232388 A1 | 9/2012 | Curra et al. |
| 2012/0259250 A1 | 10/2012 | Sapozhnikov et al. |
| 2012/0271167 A1 | 10/2012 | Holland et al. |
| 2012/0271223 A1 | 10/2012 | Khanna |
| 2013/0051178 A1 | 2/2013 | Rybyanets |
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0144165 A1 | 6/2013 | Ebbini et al. |
| 2013/0190623 A1 | 7/2013 | Bertolina et al. |
| 2013/0255426 A1 | 10/2013 | Kassow et al. |
| 2013/0303906 A1 | 11/2013 | Cain et al. |
| 2014/0030806 A1* | 1/2014 | Dudley ............ A61K 35/26 435/375 |
| 2014/0046181 A1 | 2/2014 | Benchimol et al. |
| 2014/0058293 A1 | 2/2014 | Hynynen et al. |
| 2014/0073995 A1 | 3/2014 | Teofilovic et al. |
| 2014/0074076 A1 | 3/2014 | Gertner |
| 2014/0088613 A1 | 3/2014 | Seo et al. |
| 2014/0100459 A1 | 4/2014 | Xu et al. |
| 2014/0112107 A1* | 4/2014 | Guo ............ B06B 1/00 427/596 |
| 2014/0128734 A1 | 5/2014 | Genstler et al. |
| 2014/0200489 A1 | 7/2014 | Behar et al. |
| 2014/0243664 A1 | 8/2014 | El-Sayed et al. |
| 2014/0330124 A1 | 11/2014 | Carol |
| 2014/0378832 A1 | 12/2014 | Sanghvi et al. |
| 2015/0063668 A1 | 3/2015 | You et al. |
| 2015/0073261 A1 | 3/2015 | Kohler et al. |
| 2015/0151141 A1 | 6/2015 | Arnal et al. |
| 2015/0190121 A1 | 7/2015 | Slayton et al. |
| 2015/0190659 A1 | 7/2015 | Kolher |
| 2015/0224347 A1 | 8/2015 | Barthe et al. |
| 2015/0258352 A1 | 9/2015 | Lin et al. |
| 2015/0273246 A1 | 10/2015 | Darlington et al. |
| 2015/0297177 A1 | 10/2015 | Boctor et al. |
| 2016/0004933 A1 | 1/2016 | Hu et al. |
| 2016/0114194 A1 | 4/2016 | Gertner |
| 2016/0120572 A1 | 5/2016 | Lee |
| 2016/0135782 A1 | 5/2016 | Chen et al. |
| 2016/0135916 A1 | 5/2016 | Rakic et al. |
| 2016/0151618 A1 | 6/2016 | Powers et al. |
| 2016/0184614 A1 | 6/2016 | Matula et al. |
| 2016/0206341 A1 | 7/2016 | Slayton |
| 2016/0206867 A1 | 7/2016 | Hossack et al. |
| 2016/0249859 A1 | 9/2016 | Babkin et al. |
| 2016/0287909 A1 | 10/2016 | Maxwell et al. |
| 2016/0303166 A1 | 10/2016 | Katz et al. |
| 2016/0331583 A1 | 11/2016 | Geringer |
| 2016/0331585 A1 | 11/2016 | Kim |
| 2016/0339273 A1 | 11/2016 | Al Mayiah |
| 2016/0354087 A1 | 12/2016 | Noonan et al. |
| 2016/0361574 A1 | 12/2016 | Barthe et al. |
| 2017/0000376 A1 | 1/2017 | Partanen et al. |
| 2017/0049463 A1 | 2/2017 | Popovic et al. |
| 2017/0071515 A1 | 3/2017 | Chevillet et al. |
| 2017/0072227 A1 | 3/2017 | Khokhlova et al. |
| 2017/0072228 A1 | 3/2017 | Wang et al. |
| 2017/0100145 A1 | 4/2017 | Khoklova et al. |
| 2017/0120080 A1 | 5/2017 | Phillips et al. |
| 2017/0165046 A1 | 6/2017 | Johnson et al. |
| 2017/0232277 A1 | 8/2017 | Hall et al. |
| 2017/0281983 A1 | 10/2017 | Marquet et al. |
| 2018/0000444 A1 | 1/2018 | Dayton et al. |
| 2018/0028841 A1 | 2/2018 | Konofagou et al. |
| 2018/0049719 A1 | 2/2018 | Xu et al. |
| 2018/0064412 A1 | 3/2018 | Messas et al. |
| 2018/0154186 A1 | 6/2018 | Xu et al. |
| 2018/0161086 A1* | 6/2018 | Davalos ............ A61B 18/1206 |
| 2018/0169444 A1 | 6/2018 | Averkiou et al. |
| 2018/0206816 A1 | 7/2018 | Prus et al. |
| 2018/0236271 A1 | 8/2018 | Tanter et al. |
| 2018/0317884 A1 | 11/2018 | Chapelon et al. |
| 2019/0000422 A1 | 1/2019 | West et al. |
| 2019/0023804 A1* | 1/2019 | Onik ............ A61K 39/39558 |
| 2019/0216478 A1 | 7/2019 | Maxwell et al. |
| 2019/0275353 A1 | 9/2019 | Cannata et al. |
| 2019/0282294 A1* | 9/2019 | Davalos ............ A61B 18/14 |
| 2020/0010575 A1* | 1/2020 | Hode ............ A61K 45/06 |
| 2020/0055085 A1 | 2/2020 | Taffler |
| 2020/0107843 A1 | 4/2020 | Goertz et al. |
| 2020/0164231 A1 | 5/2020 | Cannata et al. |
| 2020/0253550 A1 | 8/2020 | Nair |
| 2020/0260964 A1 | 8/2020 | Collins et al. |
| 2020/0323515 A1 | 10/2020 | Levy |
| 2020/0330039 A1 | 10/2020 | Burkett et al. |
| 2020/0330075 A1 | 10/2020 | O'Reilly et al. |
| 2020/0346046 A1 | 11/2020 | Cannata et al. |
| 2020/0353293 A1 | 11/2020 | Khokhlova et al. |
| 2020/0367835 A1 | 11/2020 | Anderson |
| 2020/0375576 A1 | 12/2020 | Moulton |
| 2020/0405258 A1 | 12/2020 | Dayton et al. |
| 2020/0405259 A1 | 12/2020 | Merritt |
| 2021/0000541 A1 | 1/2021 | Levy et al. |
| 2021/0008394 A1 | 1/2021 | Cain et al. |
| 2021/0022703 A1 | 1/2021 | Nair |
| 2021/0022714 A1 | 1/2021 | Zagrodsky et al. |
| 2021/0100527 A1 | 4/2021 | Martin |
| 2021/0108866 A1 | 4/2021 | Lucht et al. |
| 2021/0161398 A1 | 6/2021 | Millett et al. |
| 2021/0170204 A1 | 6/2021 | Vortman et al. |
| 2021/0170205 A1 | 6/2021 | Vortman et al. |
| 2021/0187331 A1 | 6/2021 | Zadicario et al. |
| 2021/0196295 A1 | 7/2021 | Goudot et al. |
| 2021/0220607 A1 | 7/2021 | Sasamine et al. |
| 2021/0353161 A1 | 11/2021 | Merritt et al. |
| 2021/0386451 A1 | 12/2021 | Escudero et al. |
| 2021/0401400 A1 | 12/2021 | Sheehan et al. |
| 2022/0008036 A1 | 1/2022 | Gulsen et al. |
| 2022/0022845 A1 | 1/2022 | Corl |
| 2022/0043143 A1 | 2/2022 | Prus et al. |
| 2022/0079563 A1 | 3/2022 | Kemp |
| 2022/0087640 A1 | 3/2022 | Minas et al. |
| 2022/0166462 A1 | 5/2022 | Deurenberg et al. |
| 2022/0168470 A1 | 6/2022 | Ricotti et al. |
| 2022/0196771 A1 | 6/2022 | Zur et al. |
| 2022/0203139 A1 | 6/2022 | Shapira |
| 2022/0233890 A1 | 7/2022 | Hynynen et al. |
| 2022/0257329 A1 | 8/2022 | Stigall et al. |
| 2022/0280233 A1* | 9/2022 | Park ............ A61B 18/14 |
| 2022/0296211 A1 | 9/2022 | Saroha et al. |
| 2022/0346756 A1 | 11/2022 | Chen |
| 2022/0395333 A1 | 12/2022 | Merritt et al. |
| 2022/0409858 A1 | 12/2022 | Lin |
| 2023/0000466 A1 | 1/2023 | Levy et al. |

(56) References Cited

U.S. PATENT DOCUMENTS

| | | |
|---|---|---|
| 2023/0000469 A1 | 1/2023 | Prus et al. |
| 2023/0008714 A1 | 1/2023 | Rajguru et al. |
| 2023/0012365 A1 | 1/2023 | Alpert et al. |
| 2023/0024998 A1 | 1/2023 | Greenberg |
| 2023/0037603 A1 | 2/2023 | Pombo et al. |
| 2023/0038543 A1 | 2/2023 | Minas et al. |
| 2023/0042834 A1 | 2/2023 | Henderson et al. |
| 2023/0050732 A1 | 2/2023 | Hancock et al. |
| 2023/0100912 A1 | 3/2023 | Amar et al. |

FOREIGN PATENT DOCUMENTS

| | | |
|---|---|---|
| CA | 3073552 A1 | 3/2019 |
| CA | 3101381 A1 | 11/2019 |
| CA | 3055856 A1 | 4/2020 |
| CA | 3153080 A1 | 4/2021 |
| CA | 2910561 C | 7/2021 |
| CA | 2908740 C | 10/2021 |
| CA | 2980976 C | 3/2023 |
| CA | 2840014 C | 8/2023 |
| CN | 1669672 A | 9/2005 |
| CN | 1732031 A | 2/2006 |
| CN | 201197744 Y | 2/2009 |
| CN | 102292123 A | 12/2011 |
| CN | 102481164 A | 5/2012 |
| CN | 102665585 A | 9/2012 |
| CN | 103537016 A | 1/2014 |
| CN | 103648361 A | 3/2014 |
| CN | 103812477 A | 5/2014 |
| CN | 104013444 A | 9/2014 |
| CN | 104135938 A | 11/2014 |
| CN | 106999076 B | 8/2017 |
| CN | 109185113 A | 1/2019 |
| CN | 109219415 A | 1/2019 |
| CN | 109689160 A | 4/2019 |
| CN | 111565642 A | 8/2020 |
| CN | 111655337 A | 9/2020 |
| CN | 111699022 A | 9/2020 |
| CN | 111712300 A | 9/2020 |
| CN | 111712301 A | 9/2020 |
| CN | 106999053 B | 10/2020 |
| CN | 107660137 B | 10/2020 |
| CN | 111757769 A | 10/2020 |
| CN | 112204412 A | 1/2021 |
| CN | 112236195 A | 1/2021 |
| CN | 106661535 B | 3/2021 |
| CN | 112533673 A | 3/2021 |
| CN | 112566694 A | 3/2021 |
| CN | 106999054 B | 5/2021 |
| CN | 106793997 B | 6/2021 |
| CN | 107530049 B | 6/2021 |
| CN | 112912011 A | 6/2021 |
| CN | 112912012 A | 6/2021 |
| CN | 112912013 A | 6/2021 |
| CN | 112969413 A | 6/2021 |
| CN | 112996445 A | 6/2021 |
| CN | 113167877 A | 7/2021 |
| CN | 113196080 A | 7/2021 |
| CN | 109196369 B | 8/2021 |
| CN | 109200484 B | 8/2021 |
| CN | 113316419 A | 8/2021 |
| CN | 113329788 A | 8/2021 |
| CN | 109640830 B | 10/2021 |
| CN | 113473917 A | 10/2021 |
| CN | 113507946 A | 10/2021 |
| CN | 113518588 A | 10/2021 |
| CN | 108135565 B | 11/2021 |
| CN | 113705586 A | 11/2021 |
| CN | 110662575 B | 12/2021 |
| CN | 109475755 B | 1/2022 |
| CN | 113905666 A | 1/2022 |
| CN | 114222536 A | 3/2022 |
| CN | 114423362 A | 4/2022 |
| CN | 108351394 B | 5/2022 |
| CN | 110248606 B | 6/2022 |
| CN | 115227992 A | 10/2022 |
| CN | 109843181 B | 11/2022 |
| CN | 115461000 A | 12/2022 |
| CN | 109091768 B | 3/2023 |
| CN | 115779285 A | 3/2023 |
| CN | 115779287 A | 3/2023 |
| CN | 115813438 A | 3/2023 |
| CN | 111032157 B | 4/2023 |
| CN | 110958858 B | 5/2023 |
| CN | 116172611 A | 5/2023 |
| CN | 111655337 B | 6/2023 |
| CN | 109416908 B | 7/2023 |
| DE | 3220751 A1 | 12/1983 |
| DE | 3544628 A1 | 6/1987 |
| DE | 3817094 A1 | 11/1989 |
| DE | 4012760 A1 | 5/1992 |
| EP | 0017382 A1 | 10/1980 |
| EP | 0320303 A2 | 6/1989 |
| EP | 0332871 A2 | 9/1989 |
| EP | 0384831 A2 | 8/1990 |
| EP | 0755653 A1 | 1/1997 |
| EP | 1374785 A1 | 1/2004 |
| EP | 1504713 A1 | 2/2005 |
| EP | 2397188 A1 | 12/2011 |
| EP | 2934308 B1 | 10/2015 |
| EP | 2934309 B1 | 10/2015 |
| EP | 3097180 B1 | 11/2016 |
| EP | 2759003 B1 | 8/2020 |
| EP | 3558457 A4 | 8/2020 |
| EP | 3700629 A1 | 9/2020 |
| EP | 3218829 B1 | 10/2020 |
| EP | 3229688 B1 | 10/2020 |
| EP | 3723857 A1 | 10/2020 |
| EP | 2887989 B1 | 2/2021 |
| EP | 3777689 A1 | 2/2021 |
| EP | 2938253 B1 | 3/2021 |
| EP | 3076864 B1 | 3/2021 |
| EP | 2802276 B1 | 4/2021 |
| EP | 2809221 B1 | 4/2021 |
| EP | 3801761 A1 | 4/2021 |
| EP | 3801762 A2 | 4/2021 |
| EP | 3801763 A1 | 4/2021 |
| EP | 2967369 B1 | 5/2021 |
| EP | 2967488 B1 | 6/2021 |
| EP | 3184048 B1 | 6/2021 |
| EP | 2967370 B1 | 9/2021 |
| EP | 3482390 B1 | 9/2021 |
| EP | 3870067 A1 | 9/2021 |
| EP | 3870069 A1 | 9/2021 |
| EP | 3876843 A1 | 9/2021 |
| EP | 2931130 B1 | 10/2021 |
| EP | 2934304 B1 | 10/2021 |
| EP | 3887843 A1 | 10/2021 |
| EP | 3888534 A1 | 10/2021 |
| EP | 3895604 A1 | 10/2021 |
| EP | 3897391 A1 | 10/2021 |
| EP | 3229672 B1 | 11/2021 |
| EP | 3558457 B1 | 11/2021 |
| EP | 3902603 A1 | 11/2021 |
| EP | 3903672 A1 | 11/2021 |
| EP | 2964096 B1 | 12/2021 |
| EP | 3930776 A1 | 1/2022 |
| EP | 3545829 B1 | 3/2022 |
| EP | 3959530 A2 | 3/2022 |
| EP | 3060129 B1 | 4/2022 |
| EP | 3986296 A1 | 4/2022 |
| EP | 3988167 A1 | 4/2022 |
| EP | 2914166 B1 | 5/2022 |
| EP | 3229674 B1 | 5/2022 |
| EP | 2779907 B1 | 6/2022 |
| EP | 3102098 B1 | 6/2022 |
| EP | 4017382 A1 | 6/2022 |
| EP | 2965263 B1 | 7/2022 |
| EP | 2726152 B1 | 8/2022 |
| EP | 4041387 A1 | 8/2022 |
| EP | 4042936 A1 | 8/2022 |
| EP | 3298959 B2 | 9/2022 |
| EP | 2931131 B1 | 11/2022 |
| EP | 2938268 B1 | 11/2022 |

(56) References Cited

FOREIGN PATENT DOCUMENTS

| | | |
|---|---|---|
| EP | 3581103 B1 | 11/2022 |
| EP | 4087492 A1 | 11/2022 |
| EP | 4093470 A1 | 11/2022 |
| EP | 3091905 B1 | 12/2022 |
| EP | 4098203 A1 | 12/2022 |
| EP | 2950737 B1 | 1/2023 |
| EP | 3057496 B1 | 1/2023 |
| EP | 2869804 B1 | 2/2023 |
| EP | 2938265 B1 | 2/2023 |
| EP | 3024403 B1 | 3/2023 |
| EP | 4151156 A1 | 3/2023 |
| EP | 2938271 B1 | 4/2023 |
| EP | 4179995 A2 | 5/2023 |
| EP | 3171764 B1 | 6/2023 |
| EP | 2931132 B1 | 7/2023 |
| EP | 3229695 B1 | 7/2023 |
| EP | 4226864 A1 | 8/2023 |
| EP | 4230121 A2 | 8/2023 |
| EP | 4230146 A1 | 8/2023 |
| EP | 4233972 A2 | 8/2023 |
| EP | 2866733 B1 | 9/2023 |
| ES | 2774069 T3 | 7/2020 |
| ES | 2819552 T3 | 4/2021 |
| ES | 2829822 T3 | 6/2021 |
| GB | 2099582 A | 12/1982 |
| HK | 1245715 B | 1/2021 |
| IL | 254768 A | 5/2021 |
| IL | 261285 B | 2/2022 |
| IN | 202117039853 A | 12/2021 |
| IN | 387413 B | 1/2022 |
| IN | 445766 B | 8/2023 |
| JP | 60-80779 A | 5/1985 |
| JP | 61-196718 A | 8/1986 |
| JP | 02-215451 A | 8/1990 |
| JP | H0422351 A | 1/1992 |
| JP | 06-197907 A | 7/1994 |
| JP | 07-504339 A | 5/1995 |
| JP | 08-84740 A | 4/1996 |
| JP | 06-304178 A | 5/1996 |
| JP | 08-131454 A | 5/1996 |
| JP | 09-55571 A | 2/1997 |
| JP | 10-512477 A | 12/1998 |
| JP | 2000300559 A | 10/2000 |
| JP | 2003510159 A | 3/2003 |
| JP | 2004505660 A | 2/2004 |
| JP | 2004249106 A | 9/2004 |
| JP | 2005167058 A | 6/2005 |
| JP | 2006511265 A | 4/2006 |
| JP | 2007144225 A | 6/2007 |
| JP | 2007520307 A | 7/2007 |
| JP | 2010019554 A | 1/2010 |
| JP | 2010029650 A | 2/2010 |
| JP | 2010204068 A | 9/2010 |
| JP | 2013538097 A | 10/2013 |
| JP | 2004512502 A | 4/2014 |
| JP | 2015519970 A | 7/2015 |
| JP | 2016508808 A | 3/2016 |
| JP | 2020525167 A | 8/2020 |
| JP | 2020525168 A | 8/2020 |
| JP | 2020525169 A | 8/2020 |
| JP | 6785554 B2 | 10/2020 |
| JP | 6789944 B2 | 11/2020 |
| JP | 2020534077 A | 11/2020 |
| JP | 2020195788 A | 12/2020 |
| JP | 2020535895 A | 12/2020 |
| JP | 6832958 B2 | 2/2021 |
| JP | 6835719 B2 | 2/2021 |
| JP | 6838057 B2 | 3/2021 |
| JP | 6849592 B2 | 3/2021 |
| JP | 2021510104 A | 4/2021 |
| JP | 6896719 B2 | 6/2021 |
| JP | 6934933 B2 | 9/2021 |
| JP | 6951560 B2 | 10/2021 |
| JP | 6979633 B2 | 12/2021 |
| JP | 6980696 B2 | 12/2021 |
| JP | 7012726 B2 | 1/2022 |
| JP | 2022500092 A | 1/2022 |
| JP | 2022500093 A | 1/2022 |
| JP | 2022501080 A | 1/2022 |
| JP | 2022504159 A | 1/2022 |
| JP | 2022509389 A | 1/2022 |
| JP | 2022509391 A | 1/2022 |
| JP | 2022509392 A | 1/2022 |
| JP | 2022509393 A | 1/2022 |
| JP | 2022509395 A | 1/2022 |
| JP | 2022509401 A | 1/2022 |
| JP | 2022509453 A | 1/2022 |
| JP | 2022510217 A | 1/2022 |
| JP | 7026118 B2 | 2/2022 |
| JP | 2022514272 A | 2/2022 |
| JP | 2022515488 A | 2/2022 |
| JP | 2022516078 A | 2/2022 |
| JP | 7053500 B2 | 4/2022 |
| JP | 2022526104 A | 5/2022 |
| JP | 2022527043 A | 5/2022 |
| JP | 2022095785 A | 6/2022 |
| JP | 7171645 B2 | 11/2022 |
| JP | 7171663 B2 | 11/2022 |
| JP | 7175640 B2 | 11/2022 |
| JP | 2022546288 A | 11/2022 |
| JP | 7187715 B2 | 12/2022 |
| JP | 2022551875 A | 12/2022 |
| JP | 2022552229 A | 12/2022 |
| JP | 7201819 B2 | 1/2023 |
| JP | 7232204 B2 | 3/2023 |
| JP | 7239466 B2 | 3/2023 |
| JP | 7265525 B2 | 4/2023 |
| JP | 2023071859 A | 5/2023 |
| JP | 7299992 B2 | 6/2023 |
| JP | 7302936 B2 | 7/2023 |
| JP | 7304344 B2 | 7/2023 |
| JP | 7321162 B2 | 8/2023 |
| JP | 7325430 B2 | 8/2023 |
| WO | WO94/06355 A1 | 3/1994 |
| WO | WO02/32506 A1 | 4/2002 |
| WO | WO2005/018469 A1 | 3/2005 |
| WO | WO2008/051484 A2 | 5/2008 |
| WO | WO2011/040054 A1 | 7/2011 |
| WO | WO2011/092683 A1 | 8/2011 |
| WO | WO2011/154654 A2 | 12/2011 |
| WO | WO2014/008594 A1 | 1/2014 |
| WO | WO2014/071386 A1 | 5/2014 |
| WO | WO2015/000953 A1 | 1/2015 |
| WO | WO2018/149671 A1 | 8/2018 |
| WO | WO2019/081329 A1 | 5/2019 |
| WO | WO2019/122941 A1 | 6/2019 |
| WO | WO2020/087049 A1 | 4/2020 |
| WO | WO2020/217098 A2 | 10/2020 |
| WO | WO2020/237382 A1 | 12/2020 |
| WO | WO2020/245660 A1 | 12/2020 |
| WO | WO2021/014221 A1 | 1/2021 |
| WO | WO2021/032887 A1 | 2/2021 |
| WO | WO2021/069216 A1 | 4/2021 |
| WO | WO2021/069971 A1 | 4/2021 |
| WO | WO2021/089810 A1 | 5/2021 |
| WO | WO2021/105358 A1 | 6/2021 |
| WO | WO2021/115958 A1 | 6/2021 |
| WO | WO2021/116763 A1 | 6/2021 |
| WO | WO2021/122253 A1 | 6/2021 |
| WO | WO2021/123905 A2 | 6/2021 |
| WO | WO2021/123906 A1 | 6/2021 |
| WO | WO2021/140042 A1 | 7/2021 |
| WO | WO2021/142090 A1 | 7/2021 |
| WO | WO2021/170510 A1 | 9/2021 |
| WO | WO2021/175626 A1 | 9/2021 |
| WO | WO2021/176275 A1 | 9/2021 |
| WO | WO2021/178961 A1 | 9/2021 |
| WO | WO2021/180501 A1 | 9/2021 |
| WO | WO2021/180550 A1 | 9/2021 |
| WO | WO2021/213927 A1 | 10/2021 |
| WO | WO2021/249936 A1 | 12/2021 |
| WO | WO2021/258007 A1 | 12/2021 |
| WO | WO2022/013266 A1 | 1/2022 |
| WO | WO2022/040493 A1 | 2/2022 |

(56) References Cited

FOREIGN PATENT DOCUMENTS

| WO | WO2022/047193 A1 | 3/2022 |
|---|---|---|
| WO | WO2022/056394 A1 | 3/2022 |
| WO | WO2022/069254 A1 | 4/2022 |
| WO | WO2022/069303 A2 | 4/2022 |
| WO | WO2022/069327 A2 | 4/2022 |
| WO | WO2022/078744 A1 | 4/2022 |
| WO | WO2022/106891 A1 | 5/2022 |
| WO | WO2022/152724 A1 | 7/2022 |
| WO | WO2022/152827 A1 | 7/2022 |
| WO | WO2022/152828 A1 | 7/2022 |

OTHER PUBLICATIONS

Wu et al.; Mechanism and dynamics of hydrodynamic-acoustic cavitation (HAC); Ultrasonics sonochemistry; vol. 49., pp. 89-96; Dec. 1, 2018.
Xu et al.; U.S. Appl. No. 17/790,975 entitled "Systems and methods for robotically-assisted histotripsy targeeting based on mri/ct scans taken prior to treatment," filed Jul. 6, 2022.
Stopek et al.; U.S. Appl. No. 17/904,326 entitled "Minimally invasive histotripsy systems and methods," filed Aug. 16, 2022.
Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.
Appel et al.; Stereoscopic highspeed recording of bubble filaments; Ultrasonics Sonochemistry; vol. 11(1); pp. 39-42; Jan. 2004.
Arani et al.; Transurethral prostate magnetic resonance elestography; prospective imaging requirements; Magn. Reson. Med.; 65(2); pp. 340-349; Feb. 2011.
Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.
Atchley et al.; Thresholds for cavitation produced in water by pulsed ultrasound; Ultrasonics.; vol. 26(5); pp. 280-285; Sep. 1988.
Avago Technologies; ACNV2601 High Insulation Voltage 10 MBd Digital Opotcoupler. Avago Technologies Data Sheet; pp. 1-11; Jul. 29, 2010.
Avago Technologies; Avago's ACNV2601 optocoupler is an optically coupled logic gate; Data Sheet; 2 pages; Jul. 29, 2010.
Avtech; AVR-8 Data sheet; May 23, 2004; 3 pages; retrieved from the internet (http//www.avtechpulse.com).
Bak; Rapid protytyping or rapid production? 3D printing processes move industry towards the latter; Assembly Automation; 23(4); pp. 340-345; Dec. 1, 2003.
Billson et al.; Rapid prototyping technologies for ultrasonic beam focussing in NDE; IEEE International Ultrasonic Symposium Proceedings; pp. 2472-2474; Oct. 2011.
Bjoerk et al.; Cool/MOS CP—How to make most beneficial use of the generation of super junction technology devices. Infineon Technologies AG. [retrieved Feb. 4, 2014] from the internet (http://www.infineon.com/dgdl/infineon+-+Application+Note+-+PowerMOSFETs+-+600V+CoolMOS%E284%A2+-+CP+Most+beneficial+use+of+superjunction+technologie+devices.pdf?folderId=db3a304412b407950112b408e8c90004&fileId=db3a304412b407950112b40ac9a40688>pp. 1, 4, 14; Feb. 2007.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).

Chan et al.; An image-guided high intensity focused ultrasound device for uterine fibroids treatment; Medical Physics, vol. 29, pp. 2611-2620, Nov. 2002.
Clasen et al.; MR-guided radiofrequency ablation of hepatocellular carcinoma: Long-term effectiveness; J Vasc Interv Radiol; 22(6); pp. 762-770; Jun. 2011.
Clement et al.; A hemisphere array for non-invasive ultrasound brain therapy and surgery; Physics in Medicine and Biology, vol. 45, p. 3707-3719, Dec. 2000.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Desilets et al.; The Design of Efficient Broad-Band Piezoelectric Transducers; Sonics and Ultrasonics, IEEE Transactions on, vol. 25, pp. 115-125, May 1978.
Emelianov et al.; Triplex ultrasound: Elasticity imaging to age deep venous thrombosis; Ultrasound Med Biol; 28(6); pp. 757-767; Jun. 2002.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System for Transcutaneous Ultrasound Surgery; AIP Conference Proceedings, Boston, MA; vol. 829, pp. 445-449, Oct. 27-29, 2005.
Hall et al.; Acoustic Access to the Prostate for Extracorporeal Ultrasound Ablation; Journal of Endourology, vol. 24, pp. 1875-1881, Nov. 2010.
Hall et al.; Histotripsy of the prostate: dose effects in a chronic canine model; Urology; 74(4); pp. 932-937; Oct. 2009 (author manuscript).
Hall et al.; Imaging feedback of tissue liquefaction (histotripsy) in ultrasound surgery; IEEE Ultrasonic Symposium, Sep. 18-21, 2005, pp. 1732-1734.
Hartmann; Ultrasonic properties of poly(4-methyl pentene-1), Journal of Applied Physics, vol. 51, pp. 310-314, Jan. 1980.
Hobarth et al.; Color flow doppler sonography for extracorporal shock wave lithotripsy; Journal of Urology; 150(6); pp. 1768-1770; Dec. 1, 1993.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.
Hynynen et al.; Tissue thermometry during ultrasound exposure; European Urology; 23(Suppl 1); pp. 12-16; (year of pub. sufficiently earlier than effective US filing date and any foreign priority date) 1993.
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.
Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.
Kim et al.; Dependence of particle volume fraction on sound velocity and attenuation of EPDM composites; Ultrasonics, vol. 46, pp. 177-183, Feb. 2007.
Konofagou; Quo vadis elasticity imaging?; Ultrasonics; 42(1-9); pp. 331-336; Apr. 2004.
Krimholtz et al.; New equivalent circuits for elementary piezoelectric transducers; Electronics Letters, vol. 6, pp. 398-399, Jun. 1970.
Kruse et al.; Tissue characterization using magnetic resonance elastography: Preliminary results; Phys. Med. Biol; 45(6); pp. 1579-1590; Jun. 2000.

(56) References Cited

OTHER PUBLICATIONS

Lake et al.; Histotripsy: minimally invasive technology for prostatic tissue ablation in an in vivo canine model; Urology; 72(3); pp. 682-686; Sep. 2008.
Lauterborn et al.; Cavitation bubble dynamics studied by high speed photography and holography: part one; Ultrasonics; vol. 23; pp. 260-268; Nov. 1985.
Lensing et al.; Deep-vein thrombosis; The Lancet, vol. 353, pp. 479-485, Feb. 6, 1999.
Lin et al; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).
Liu et al.; Real-time 2-D temperature imaging using ultrasound; IEEE Trans Biomed Eng; 57(1); pp. 12-16; Jan. 2010 (author manuscript, 16 pgs.).
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al; Effect of Radial Displacement of Lens on Response of Focused Ultrasonic Transducer; Japanese Journal of Applied Physics, vol. 46, p. 3077-3085; May 15, 2007.
Maréchal et al; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Cavitation clouds created by shock scattering from bubbles during histotripsy; J. Acoust. Soc. Am.; 130(4); pp. 1888-1898; Oct. 2011.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Maxwell; Noninvasive thrombolysis using histotripsy pulsed ultrasound cavitation therapy; PhD Dissertation. University of Michigan, Ann Arbor, Michigan. Jun. 2012.
Maxwell et al.; In-vivo study of non-invasive thrombolysis by histotripsy in a porcine model; IEEE international Ultrasonics Symposium; IEEE; p. 220-223; Sep. 20, 2009.
Maxwell et al.; The role of compressional pressure in the formation of dense bubble clouds in histotripsy; 2009 IEEE International Ultrasonics Symposium; pp. 81-84; Sep. 20, 2009.
Miller et al.; A review of in vitro bioeffects of inertial ultrasonic cavitation from a mechanistic perspective; Ultrasound in Medicine and Biology; vol. 22; pp. 1131-1154; (year of publication is sufficiently earlier than the effective U.S. filing date and any foreign priority date) 1996.
Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.
Miller et al.; Real-time elastography-based monitoring of histotripsy tissue fractionation using color doppler; Ultrasonics Symposium (IUS); 2012 IEEE International; 8 pages; Oct. 7-10, 2012.
Nightingale et al.; Analysis of contrast in images generated with transient acoustic radiation force; Ultrasound Med Biol; 32(1); pp. 61-72; Jan. 2006.
Ohl et al.; Bubble dynamics, shock waves and sonoluminescence; Phil. Trans. R. Soc. Lond. A; vol. 357; pp. 269-294; (year of publication is sufficiently earlier than the effective U.S. filing date and any foreign priority date) 1999.
Okada et al.; A case of hepatocellular carcinoma treated by MR-guided focused ultrasound ablation with respiratory gating; Magn Reson Med Sci; 5(3); pp. 167-171; Oct. 2006.
Palmeri et al.; Acoustic radiation force-based elasticity imaging methods; Interface Focus; 1; pp. 553-564; Aug. 2011.
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Parsons et al.; Pulsed cavitational ultrasound therapy for controlled tissue homogenization; Ultrasound in Med. & Biol.; vol. 32(1); pp. 115-129; Jan. 2006.
Pishchalnikov et al.; Cavitation Bubble Cluster Activity in the Breakage of Kidney Stones by Lithotripter Shock Waves; J Endourol.; 17(7): 435-446; Sep. 2003.
Porter et al.; Reduction in left ventricular cavitary attenuation and improvement in posterior myocardial contrast . . . ; J Am Soc Echocardiography; pp. 437-441; Jul.-Aug. 1996.
Qu et al.; Non-thermal histotripsy tumor ablation promotes abscopal immune responses that enhance cancer immunotherapy; Journal for immunotherapy of cancer; 8(1); Jan. 15, 2020.
Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.
Rosenschein et al.; Ultrasound Imaging-Guided Noninvasive Ultrasound Thrombolysis: Preclinical Results; Circulation; vol. 102; pp. 238-245, Jul. 11, 2000.
Rowland et al.; MRI study of hepatic tumours following high intensity focused ultrasound surgery; British Journal of Radiology; 70; pp. 144-153; Feb. 1997.
Roy et al.; A precise technique for the measurement of acoustic cavitation thresholds and some preliminary results; Journal of the Acoustical Society of America; vol. 78(5); pp. 1799-1805; Nov. 1985.
Sapareto et al.; Thermal dose determination in cancer therapy; Int J Radiat Oncol Biol Phys; 10(6); pp. 787-800; Apr. 1984.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.
Sato et al.; Experimental Investigation of Phased Array Using Tapered Matching Layers. 2002 IEEE Ultrasound Symposium. vol. 2; pp. 1235-1238, Oct. 2002.
Sferruzza et al.; Generation of high power unipolar pulse with a piezocomposite transducer; In 1999 IEEE Ultrasonics Symposium Proceedings; International Symposium (Cat. No. 99CH37027); vol. 2; pp. 1125-1128; Oct. 17, 1999.
Shung; Diagnostic Ultrasound: Imaging and Blood Flow Measurements; Taylor and Francis Group, LLC; Boca Raton, FL; 207 pages; (year of pub. sufficiently earlier than effective US filing date and any foreign priority date) 2006.
Simonin et al.; Characterization of heterogeneous structure in a polymer object manufactured by stereolithography with low-frequency microechography; Journal of Materials Chemistry; vol. 6, pp. 1595-1599, Sep. 1996.
Sokolov et al.; Use of a dual-pulse lithotripter to generate a localized and intensified cavitation field; Journal of the Acoustical Society of America; vol. 110(3); pp. 1685-1695; Sep. 2001.
Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).
Souchon et al.; Visualisation of HIFU lesions using elastography of the human prostate in vivo: Preliminary results; Ultrasound Med. Biol; 29(7); pp. 1007-1015; Jul. 2003.
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011[retrieved on Jan. 28, 2014] from: (http://web.archive.org/web/20110720091822/http://www.histotripsy.umich.edu/index.html>.entiredocument) Jul. 2011.
Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.

(56) References Cited

OTHER PUBLICATIONS

Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.

Van Kervel et al.; A calculation scheme for the optimum design of ultrasonic transducers; Ultrasonics, vol. 21, pp. 134-140, May 1983.

Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.

Wikipedia; Medical ultrasound; 15 pages; retrieved from the internet (https://en.wikipedia.org/w/index.php?title=Medical_utrasound&oldid=515340960) on Jan. 12, 2018.

Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).

Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.

Xu et al.; Controlled ultrasound tissue erosion: the role of dynamic interaction between insonation and microbubble activity; Journal of the Acoustical Society of America; vol. 117(1); pp. 424-435; Jan. 2005.

Xu et al.; Controlled ultrasound tissue erosion; IEEE Transaction on Ultrasonics, Ferroelectrics, and Frequency Control; vol. 51 (6); pp. 726-736; Jun. 2004.

Xu et al.; Effects of acoustic parameters on bubble cloud dynamics in ultrasound tissue erosion (histotripsy); Journal of the Acoustical Society of America; vol. 122(1); pp. 229-236; Jul. 2007.

Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.

Xu et al.; Investigation of intensity threshold for ultrasound tissue erosion; Ultrasound in Med. & Biol.; vol. 31(12); pp. 1673-1682; Dec. 2005.

Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.

Yan et al.; A review of rapid prototyping technologies and systems; Computer-Aided Design, vol. 28, pp. 307-318, Apr. 1996.

Zhang et al.; A fast tissue stiffness-dependent elastography for HIFU-induced lesions inspection; Ultrasonics; 51(8); pp. 857-869; Dec. 2011.

Zheng et al.; An acoustic backscatter-based method for localization of lesions induced by high-intensity focused ultrasound; Ultrasound Med Biol; 36(4); pp. 610-622; Apr. 2010.

Haller et al.; Determination of acoustic cavitation probabilities and thresholds using a single focusing transducer to induce and detect acoustic cavitation events: I. Method and terminology; Ultrasound in Medicine & Biology; 44(2); pp. 377-396; Feb. 1, 2018.

Macoskey; Acoustic methods for histotripsy feedback; (Dissertation); Biomedical Engineering and Science Computing; University of Michigan 2019; 207 pages; retrived from the internet (https://deepblue.lib.umich.edu/handle/2027.42/149988) on Feb. 2022.

Xu et al.; U.S. Appl. No. 17/407,780 entitled "Histotripsy therapy systems and methods for the treatment of brain tissue," filed Aug. 20, 2021.

Dovedi et al.; Acquired Resistance to Fractionated Radiotherapy Can Be Overcome by Concurrent PD-LI Blockade; Cancer Research; 74(19); pp. 5458-5468; Oct. 1, 2014.

Rakic et al.; U.S. Appl. No. 17/929,951 entitled "Articulating arm limiter for cavitational ultrasound therapy system," filed Sep. 6, 2022.

Stopek et al.; U.S. Appl. No. 18/002,204 entitled "Histotripsy acoustic and patient coupling systems and methods," filed Dec. 16, 2022.

\* cited by examiner

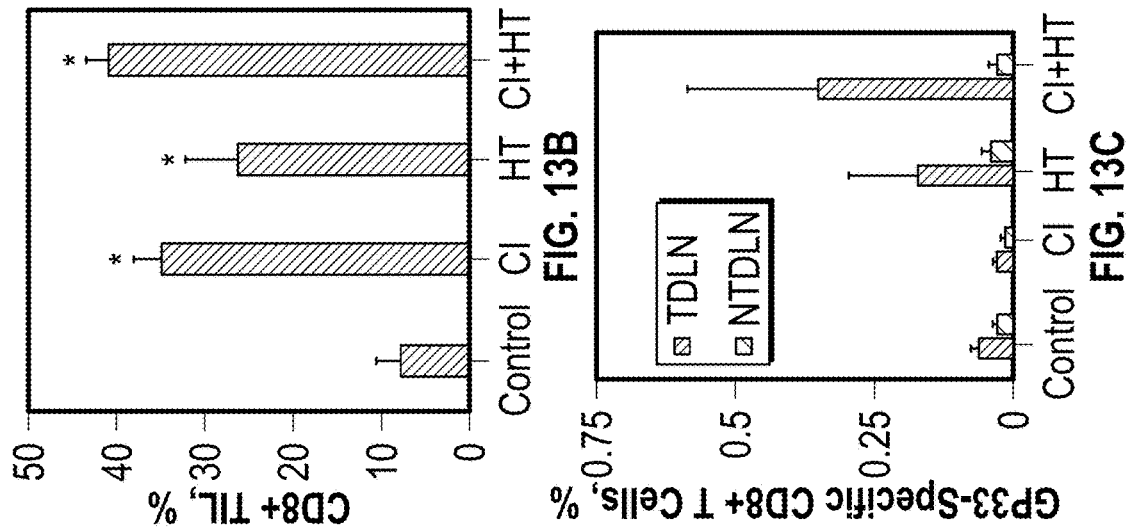
FIG. 13B
FIG. 13C
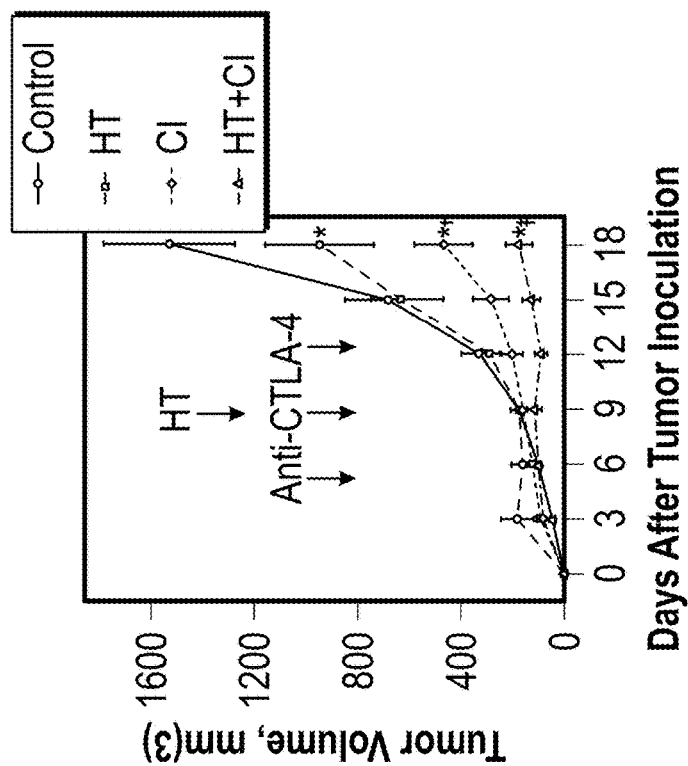
FIG. 13A

SYSTEMS AND METHODS FOR HISTOTRIPSY IMMUNOSENSITIZATION

CROSS REFERENCE TO RELATED APPLICATIONS

This application claims the benefit of priority of U.S. Provisional Application No. 62/966,960, filed Jan. 28, 2020, the disclosure of which is herein incorporated by reference in its entirety.

STATEMENT AS TO FEDERALLY SPONSORED RESEARCH

This invention was made with Government support under CA211217 awarded by the National Institutes of Health. The Government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure details novel high intensity therapeutic ultrasound (HITU) systems configured to produce acoustic cavitation, methods, devices and procedures for the minimally and non-invasive treatment of healthy, diseased and/or injured tissue. The acoustic cavitation systems and methods described herein, also referred to Histotripsy, may include transducers, drive electronics, positioning robotics, imaging systems, and integrated treatment planning and control software to provide comprehensive treatment and therapy for soft tissues in a patient.

BACKGROUND

Histotripsy, or pulsed ultrasound cavitation therapy, is a technology where extremely short, intense bursts of acoustic energy induce controlled cavitation (microbubble formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm; it is necessary to deliver acoustic energy in the form of high amplitude acoustic pulses with low duty cycle.

Compared with conventional focused ultrasound technologies, Histotripsy has important advantages: 1) the destructive process at the focus is mechanical, not thermal; 2) cavitation appears bright on ultrasound imaging thereby confirming correct targeting and localization of treatment; 3) treated tissue generally, but not always, appears darker (more hypoechoic) on ultrasound imaging, so that the operator knows what has been treated; and 4) Histotripsy produces lesions in a controlled and precise manner. It is important to emphasize that unlike thermal ablative technologies such as microwave, radiofrequency, and high-intensity focused ultrasound (HIFU), Histotripsy relies on the mechanical action of cavitation for tissue destruction.

Cancer immunotherapy harnesses the flexibility and power of the immune system to recognize and reject tumors based on their expression of foreign antigens. Contemporary immunotherapy using monoclonal antibodies against CTLA-4 and PD-1 that disable the ability of cancers to suppress CD8+ T cells has revolutionized the management of cancers like melanoma and lung cancer. Cancers overcome the immune system in two ways: (1) actively disabling immune responses, such as through the engagement of checkpoint mechanisms, and; (2) passively avoiding detection, veiling their antigens from the immune system. Advances in cancer immunotherapy are finally being actualized with checkpoint inhibition (CI) therapy. CI targets the first mechanism of immune suppression, but does nothing to mitigate the second mechanism of immune avoidance.

The limits of these types of immunotherapy are already evident. The first limit is inherent non-specificity; because the effects of CI are not limited to tumor-directed T cell responses, its efficacy is inextricably linked to autoimmune complications, and more aggressive combinatorial approaches to CI have only increased the risk of occasionally life-threatening autoimmunity. The second limit is its limited utility; whereas CI works well against inherently immunogenic cancers like melanoma and lung cancer, it has not altered the prognosis of stubbornly non-immunogenic cancers like liver and pancreatic malignancies.

Recently, high intensity focused ultrasound (HIFU) thermal ablation has been shown to induce anti-tumor immunity in preclinical and clinical studies. Some evidence suggests that cells in the periphery of the HIFU ablation zone do not receive a lethal thermal dose, but experience thermal stresses that ultimately lead to apoptosis, triggering tumor-specific inflammation. HIFU has been shown to induce anti-tumor immunity in poorly immunogenic murine tumor models. In addition, there is early evidence showing that boiling histotripsy, which uses millisecond pulses to reach boiling and liquefy tissue, may stimulate immune responses to tumor.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 13A-13C illustrate an experiment which shows that histotripsy enhances the efficacy of immunotherapy.

SUMMARY OF THE DISCLOSURE

Figure 1A:
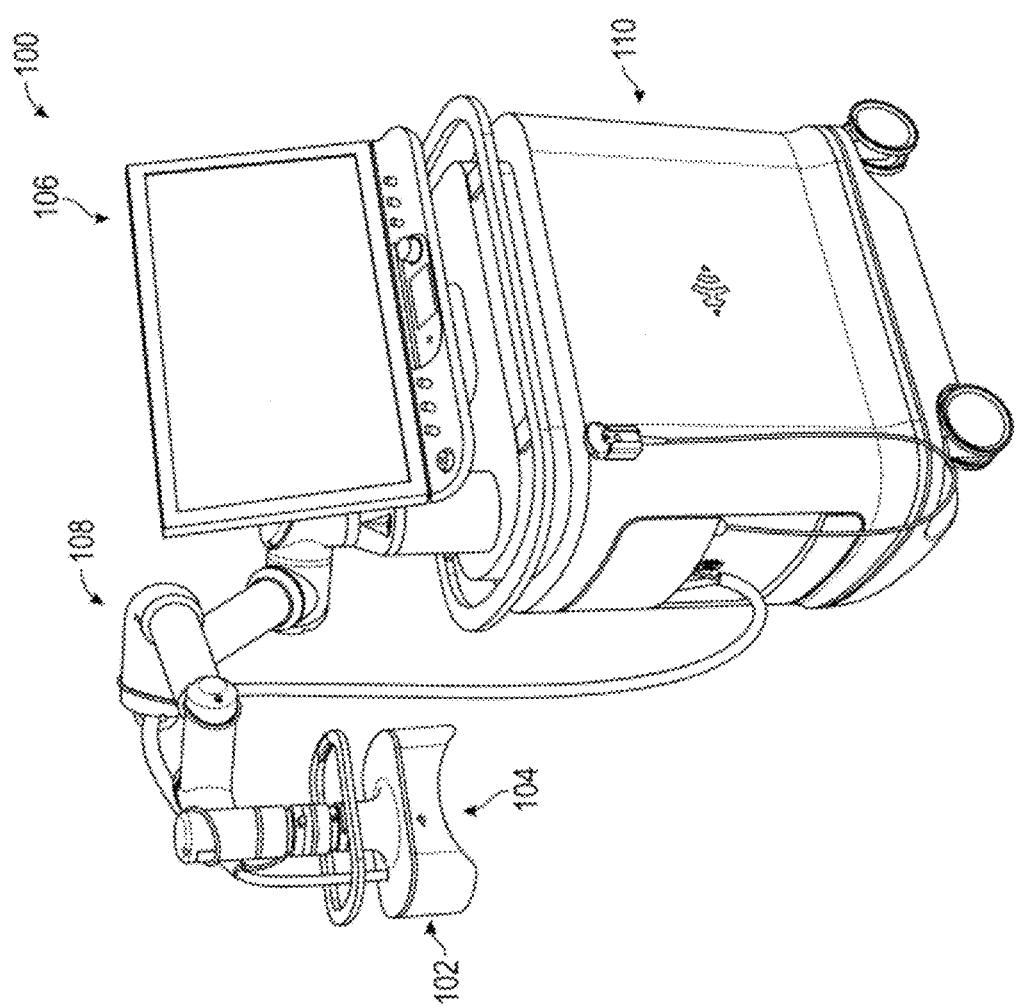
FIGS. 1A-1B illustrate an ultrasound imaging and therapy system.

A method of treating tissue is provided, comprising identifying at least one target tumor, determining a treatment volume and a treatment location of the at least one target tumor that will increase a cell response of releasing tumor antigens, applying histotripsy treatment based on the treatment volume and treatment location to the at least one target tumor to mechanically lyse and solubilize tumor cells to release tumor antigens. In some embodiments, the method can be for treating tissue previously treated with radiation therapy and/or resistant to radiation therapy. In other embodiments, the method can be for treating tissue previously treated with immunotherapy and non-responsive or resistant to immunotherapy.

In some embodiments, the cell response includes immunogenic cell death, infiltration of inflammatory and antigen presenting cells, infiltration and activation of T cells, increased tumor-specific T cells, infiltration of natural killer cells, B cells and CD4+ T cells, and/or depletion of immunosuppressive regulatory T cells and myeloid-derived suppressor cells.

In some embodiments, the treatment volume of the at least one target tumor ranges from 25% to 90% of a volume of the at least one target tumor. In other embodiments, the treatment volume of the at least one target tumor is at least 1 cm3 in volume.

In some embodiments, the method further includes evaluating an immune response of the lysed and solubilized tumor cells.

In one embodiment, evaluating the immune response includes assessment of immunological cell death and/or immune activation. In one embodiment, evaluating the immune response comprises imaging the at least one target tumor and/or performing a tissue biopsy on the at least one target tumor. In one embodiment, the imaging comprises CT, MRI, and/or PET imaging. In some embodiments, performing the tissue biopsy comprises performing a liquid biopsy.

In one embodiment, the method further includes applying immune therapy after applying histotripsy treatment. In one embodiment, the immune therapy is selected from the group consisting of checkpoint inhibitors, immunostimulatory therapies, cancer vaccines, oncolytic viruses, neutralizing immune inhibitors, and activating cytokines. In some examples, the checkpoint inhibitors include CTLA-4, LAG3, TIM3, and combinations thereof. In other examples, the checkpoint inhibitors include PD-1 blockade, PD-L1 blockade, and combinations thereof.

In some embodiments, the method further includes harvesting the lysed and solubilized tumor cells. In some embodiments, the method includes preparing an immune directed therapy using the lysed and solubilized tumor cells, and administering the immune directed therapy into a patient. In some embodiments, administering the immune directed therapy is selected from the group consisting of oral administration, systemic infusion, loco-regional catheter-based infusion, intratumoral injection, loco-regional injection, subcutaneous injection, and combinations thereof. In one embodiment, the immune directed therapy is a cell therapy.

In some implementations, applying the histotripsy treatment is configured to elicit an immune response in at least one distant tumor of the same phenotype as the at least one target tumor. In one example, the at least one distant tumor is located in a different organ or anatomical location than the at least one target tumor.

In some embodiments, the at least one target tumor is located in the group consisting of a liver, a kidney, a spleen, a pancreas, a colorectal, a bowel, a stomach, an esophagus, a breast, a lung, a head, a neck, a thyroid, skin, nervous tissue, hematological malignancies, a sarcoma, primary and metastatic lesions, and brain tissue.

In some embodiments, the treatment location comprises only an inner portion of the at least one target tumor. In other embodiments, the treatment location comprises only an outer portion of the at least one target tumor. In another embodiment, the treatment location comprises a plurality of programmed treatment locations distributed spatially through the at least one target tumor.

A method of treating tissue previously treated with radiation therapy and/or resistant to radiation therapy is provided, comprising identifying at least one target tumor, determining a treatment volume and a treatment location of the at least one target tumor that will increase cell response of releasing tumor antigens, determining a treatment location that will increase cell response of releasing tumor antigens, applying histotripsy treatment to the at least one target tumor to mechanically lyse and solubilize tumor cells to release tumor antigens.

A method of treating tissue previously treated with immunotherapy and non-responsive or resistant to immunotherapy is also provided, comprising identifying at least one target tumor, determining a treatment volume and a treatment location of the at least one target tumor that will increase cell response of releasing tumor antigens, determining a treatment location that will increase cell response of releasing tumor antigens, applying histotripsy treatment to the at least one target tumor to mechanically lyse and solubilize tumor cells to release tumor antigens.

A method of treating tissue is provided, comprising identifying at least one target tumor, determining a treatment volume and a treatment location of the at least one target tumor that will increase induction of immunogenic cell death, applying histotripsy treatment based on the treatment volume and treatment location to the at least one target tumor to mechanically lyse and solubilize tumor cells and induce immunogenic cell death.

In some embodiments, applying the histotripsy treatment causes the release of damage associated molecular patterns (DAMPs). In one embodiment, the DAMPs are selected from the group consisting of High Mobility Group Box 1 (HMGB1), calreticulin (CRT), adenosine triphosphate (ATP), heat shock proteins (HSP), fibronectin (FN), deoxyribonucleic acid (DNA), ribonucleic acid (RNA) and combinations thereof. In some examples, DNA comprises cell-free DNA. In other embodiments, RNA comprises mRNA.

In some embodiments, the method further comprises evaluating an immune response of the lysed and solubilized tumor cells.

In some embodiments, the method further includes applying immune therapy after applying histotripsy treatment. In some examples, applying the immune therapy is selected from the group consisting of checkpoint inhibitors, immunostimulatory therapies, cancer vaccines, oncolytic viruses, neutralizing immune inhibitors, activating cytokines and various combinations of. In one embodiment, the checkpoint inhibitors include CTLA-4, LAGS, TIM3, and combinations thereof. In another embodiment, the checkpoint inhibitors include PD-1 blockade, PD-L1 blockade, and combinations thereof.

In some embodiments, the method further includes harvesting the lysed and solubilized tumor cells.

In another embodiment, the method includes preparing an immune directed therapy using the lysed and solubilized tumor cells; and administering the immune directed therapy into a patient.

In some examples, the at least one target tumor is located in the group consisting of a liver, a kidney, a spleen, a pancreas, a colorectal, a bowel, a stomach, an esophagus, a breast, a lung, a head, a neck, a thyroid, skin, nervous tissue, hematological malignancies, a sarcoma, primary and metastatic lesions, and brain tissue.

A method of treating tissue is provided, comprising identifying a target tissue volume, placing a focus of a histotripsy transducer within the target tissue volume, applying histotripsy to a subset of the target tissue volume to mechanically lyse and solubilize tumor cells of only a portion of the target tissue volume to release tumor antigens, and evaluating an immune response of the lysed and solubilized tumor cells.

In some embodiments, the method includes identifying a target tissue volume further comprises identifying a first target tissue volume and a second target tissue volume. In some embodiments, the first and second target tissue volumes are located in the same organ or anatomical location. In other embodiments, the first and second target tissue volumes are located in different organs or anatomical locations.

In one embodiment, evaluating the immune response comprises evaluating the immune response in one or more organs or anatomical locations. In other embodiments, evaluating the immune response comprises imaging the at least one target tumor and/or performing a tissue biopsy on the at least one target tumor. In another embodiment, evaluating the immune response includes biomarker analyses of tissue, cells, blood and/or combinations thereof.

In some embodiments, applying histotripsy to a subset of the target tissue volume further comprises applying histotripsy to only an inner portion of the target tissue volume. In another embodiment, applying histotripsy to a subset of the target tissue volume further comprises applying histotripsy to only an outer portion of the target tissue volume. In some embodiments, applying histotripsy to a subset of the target tissue volume further comprises applying histotripsy to a plurality of programmed treatment locations distributed spatially through the target tissue volume.

In one example, the subset of the target tissue volume comprises approximately 25% to 90% of the target tissue volume. In another example, the subset of the target tissue volume is at least 1 cm3 in volume.

In some embodiments, the method includes applying immune therapy after applying histotripsy. In one embodiment, the immune therapy is selected from the group consisting of checkpoint inhibitors, immunostimulatory therapies, cancer vaccines, oncolytic viruses, neutralizing immune inhibitors, and activating cytokines. In some embodiments, the checkpoint inhibitors include CTLA-4, LAG3, TIM3, and combinations thereof. In other embodiments, the checkpoint inhibitors include PD-1 blockade, PD-L1 blockade, and combinations thereof.

In one example, applying the immune therapy further comprises applying the immune therapy between 1 to 6 weeks after applying histotripsy. In other examples, applying the immune therapy further comprises applying the immune therapy between 2 to 4 weeks after applying histotripsy.

In one embodiment, placing the focus further comprises placing the focus with a robotic positioning system. In some examples, the robotic positioning system comprises a robotic arm with a minimum of 3 degrees of freedom. In another embodiment, the robotic positioning system comprises a robotic arm that directs a histotripsy therapy transducer through a pre-programmed three-dimensional treatment routine.

In some embodiments, applying the immune therapy is selected from the group consisting of oral administration, systemic infusion, loco-regional catheter-based infusion, intratumoral injection, loco-regional injection, subcutaneous injection, and combinations thereof.

In another embodiment, the robotic positioning system is used for the loco-regional catheter infusion, loco-regional injection, intratumoral injection, and/or combinations thereof.

In some embodiments, the method further comprises harvesting the lysed and solubilized tumor cells.

In another embodiment, the method includes preparing an immune directed therapy using the lysed and solubilized tumor cells, and administering the immune directed therapy into a patient.

In one embodiment, the at least one target tumor is located in the group consisting of a liver, a kidney, a spleen, a pancreas, a colorectal, a bowel, a stomach, an esophagus, a breast, a lung, a head, a neck, a thyroid, skin, nervous tissue, hematological malignancies, a sarcoma, primary and metastatic lesions, and brain tissue.

A method of creating a vaccine is provided, comprising identifying a target tissue volume, placing a focus of a histotripsy transducer within the target tissue volume, applying histotripsy to a subset of the target tissue volume to mechanically lyse and solubilize cells of only a portion of the target tissue volume to release tumor antigens, harvesting the lysed and solubilized cells, and creating a targeted cancer vaccine from components of the harvested cells.

In some embodiments, the target tissue volume is a cancerous tumor. In other embodiments, the target tissue volume is located in a patient. In another embodiment, the target tissue volume is located outside of a patient. In another example, the target tissue is derived from a biopsy. In some embodiments, the biopsy includes a cytological, whole tissue, surgical, fresh, fresh frozen, embedded, or fixed tissue samples, and/or combinations thereof.

In one embodiment, the target tissue volume is derived from multiple patients having the same target tumor phenotypes. In another embodiment, the target tissue volume is derived from multiple target tumor phenotypes.

In some examples, the method further includes administering the vaccine to one or more patients. In one embodiment, the vaccine is administered locally, regionally or systemically.

In some examples, the target tissue volume is derived from the group consisting of a liver, a kidney, a spleen, a pancreas, a colorectal, a bowel, a stomach, an esophagus, a breast, a lung, a head, a neck, a thyroid, skin, nervous tissue, and brain tissue.

A method of treating tissue is also provided, comprising identifying a first target tumor and one or more additional non-target tumors, placing a focus of a histotripsy transducer within the first target tumor, applying histotripsy to a subset of the first target tumor to mechanically lyse and solubilize tumor cells of only a portion of the first target tumor to release tumor antigens, and evaluating a distant immune effect of the lysed and solubilized tumor cells on the one or more additional non-target tumors.

In some embodiments, the method further comprises applying immune therapy after applying histotripsy. In one example, applying histotripsy is neoadjuvant to applying immune therapy.

In one embodiment, the distant immune effect on the one or more additional non-target tumors is located in the same organ or anatomical space as the first target tumor. In another example, the distant immune effect on the one or more additional non-target tumors are located in different organs or anatomical spaces than the first target tumor.

In some embodiments, evaluating the immune response comprises imaging the at least one target tumor and/or performing a tissue biopsy on the at least one target tumor. In other embodiments, evaluating the immune response comprises performing a biomarker analyses of tissue, cells, blood and/or combinations thereof. In another embodiment, evaluating the immune response includes assessing an amount of immune response to the lysed and solubilized tumor cells.

In some examples, the subset comprises an inner portion of the first target tumor. In another embodiment, the subset comprises an outer portion of the first target tumor. In another embodiment, the subset comprises a plurality of programmed treatment locations distributed spatially through the first target tumor. In some examples, the subset ranges from 25% to 90% of the first target tumor. In another example, the subset of the target tissue volume is at least 1 cm$^3$ in volume.

In some embodiments, the method further includes applying immune therapy after applying histotripsy. In some embodiments, the immune therapy is selected from the group consisting of checkpoint inhibitors, immunostimulatory therapies, cancer vaccines, oncolytic viruses, neutralizing immune inhibitors, and activating cytokines. In some embodiments, the checkpoint inhibitors include CTLA-4, LAG3, TIM3, and combinations thereof. In another embodiment, the checkpoint inhibitors include PD-1 blockade, PD-L1 blockade, and combinations thereof.

In some embodiments, the method further includes harvesting the lysed and solubilized tumor cells.

In another embodiment, the method includes preparing an immune directed therapy using the lysed and solubilized tumor cells, and administering the immune directed therapy into a patient.

In one embodiment, the placing step comprises placing the focus with a robotic positioning system. In one embodiment, the robotic positioning system comprises a robotic arm with a minimum of 3 degrees of freedom. In another embodiment, the robotic positioning system comprises a robotic arm that directs a histotripsy therapy transducer through a pre-programmed three-dimensional treatment routine.

In some examples, applying the immune therapy is selected from the group consisting of oral administration, systemic infusion, loco-regional catheter-based infusion, intratumoral injection, loco-regional injection, subcutaneous injection, and combinations thereof.

In one embodiment, the robotic positioning is used for the loco-regional catheter infusion, loco-regional injection, intratumoral injection, and/or combinations thereof.

In some embodiments, the first target tumor is located in the group consisting of a liver, a kidney, a spleen, a pancreas, a colorectal, a bowel, a stomach, an esophagus, a breast, a lung, a head, a neck, a thyroid, skin, nervous tissue, hematological malignancies, a sarcoma, primary and metastatic lesions, and brain tissue.

A method of treating tissue is further provided, comprising identifying at least one target tumor of a plurality of tumors, placing a focus of a histotripsy transducer within the at least one target tumor, applying histotripsy test pulses to the at least one target tumor to determine a cavitation threshold at one or more test locations within the at least one target tumor, deriving a histotripsy treatment plan based on the determined cavitation threshold at the one or more test locations, applying an automated histotripsy therapy using the treatment plan to mechanically lyse and solubilize tumor cells of only a portion of the at least one target tumor to release tumor antigens, evaluating an immune response of the lysed and solubilized tumor cells, and administering an immune therapy to treat the plurality of tumors.

In one example, applying the immune therapy further comprises applying the immune therapy between 1 to 6 weeks after applying histotripsy. In other examples, applying the immune therapy further comprises applying the immune therapy between 2 to 4 weeks after applying histotripsy.

In some embodiments, the plurality of tumors are in the same organ or anatomical locations. In other embodiments, the plurality of tumors are in different organs or anatomical locations.

In one embodiment, evaluating the immune response comprises evaluating the immune response in one or more organs or anatomical locations. In other embodiments, evaluating the immune response comprises imaging the at least one target tumor and/or performing a tissue biopsy on the at least one target tumor.

In one embodiment, evaluating the immune response includes biomarker analyses of tissue, cells, blood and/or combinations thereof.

In other embodiments, evaluating the immune response includes evaluating an amount of immune response to the lysed and solubilized tumor cells.

In one example, only an inner portion of the at least one target tumor is lysed and solubilized. In another embodiment, only an outer of the at least one target tumor is lysed and solubilized.

In some examples, the histotripsy treatment plan comprises a plurality of programmed treatment locations distributed spatially through the at least one target tumor.

In one embodiment, the histotripsy treatment plan lyses and solubilizes between 25% to 90% of the at least one target tumor. In another embodiment, the histotripsy treatment plan lyses and solubilizes at least 1 cm3 of the at least one target tumor.

In some examples, the immune therapy is selected from the group consisting of checkpoint inhibitors, immunostimulatory therapies, cancer vaccines, oncolytic viruses, neutralizing immune inhibitors, and activating cytokines. In some embodiments, the checkpoint inhibitors include CTLA-4, LAG3, TIM3, and combinations thereof. In another embodiment, the checkpoint inhibitors include PD-1 blockade, PD-L1 blockade, and combinations thereof.

In some examples, the method further comprises harvesting the lysed and solubilized tumor cells. The method can additionally include preparing an immune directed therapy using the lysed and solubilized tumor cells, and administering the immune directed therapy into a patient.

In some embodiments, the placing step comprises placing the focus with a robotic positioning system. In one embodiment, the robotic positioning system comprises a robotic arm with a minimum of 3 degrees of freedom. In another embodiment, the robotic positioning system comprises a robotic arm that directs a histotripsy therapy transducer through a pre-programmed three-dimensional treatment routine.

In some embodiments, applying the immune therapy is selected from the group consisting of oral administration, systemic infusion, loco-regional catheter-based infusion, intratumoral injection, loco-regional injection, subcutaneous injection, and combinations thereof.

In one example, the robotic positioning is used for the loco-regional catheter infusion, loco-regional injection, intratumoral injection, and/or combinations thereof.

In some embodiments, the first target tumor is located in the group consisting of a liver, a kidney, a spleen, a pancreas, a colorectal, a bowel, a stomach, an esophagus, a breast, a lung, a head, a neck, a thyroid, skin, nervous tissue, hematological malignancies, a sarcoma, primary and metastatic lesions, and brain tissue.

A histotripsy therapy system is provided comprising a medical imaging modality configured to identify at least one target tumor of a plurality of tumors, a robotic positioning system including a histotripsy therapy transducer, the robotic positioning system being configured to place a focus of the histotripsy transducer within the at least one target tumor, an electronic controller configured to apply histotripsy test pulses to the at least one target tumor from the histotripsy therapy transducer to determine a cavitation threshold at one or more test locations within the at least one target tumor, the electronic controller being further configured to derive a histotripsy treatment plan based on the determined cavitation threshold at the one or more test locations, the electronic controller being further configured to apply automated histotripsy therapy with the histotripsy therapy transducer using the treatment plan to mechanically lyse and solubilize tumor cells of only a portion of the at least one target tumor to release tumor antigens, and an evaluation device configured to evaluate an immune response of the lysed and solubilized tumor cells.

In some embodiments, the robotic positioning system is further configured to administer an immune therapy to treat the plurality of tumors.

In another embodiment, the evaluation device comprises a biopsy device, a blood testing device or system, or a medical imaging device or system.

DETAILED DESCRIPTION

The system, methods and devices of the disclosure may be used for the minimally or non-invasive acoustic cavitation and treatment of healthy, diseased and/or injured tissue, including in extracorporeal, percutaneous, endoscopic, laparoscopic, and/or as integrated into a robotically-enabled medical system and procedures. As will be described below, the acoustic cavitation system may include various sub-systems, including a Cart, Therapy, Integrated Imaging, Robotics, Coupling and Software. The system also may comprise various Other Components, Ancillaries and Accessories, including but not limited to computers, cables and connectors, networking devices, power supplies, displays, drawers/storage, doors, wheels, and various simulation and training tools, etc. All systems, methods and means creating/controlling/delivering histotripsy are considered to be a part of this disclosure, including new related inventions disclosed herein.

FIG. 1A generally illustrates histotripsy system 100 according to the present disclosure, comprising a therapy transducer 102, an imaging system 104, a display and control panel 106, a robotic positioning arm 108, and a cart 110. The system can further include an ultrasound coupling interface and a source of coupling medium, not shown.

Figure 1B:
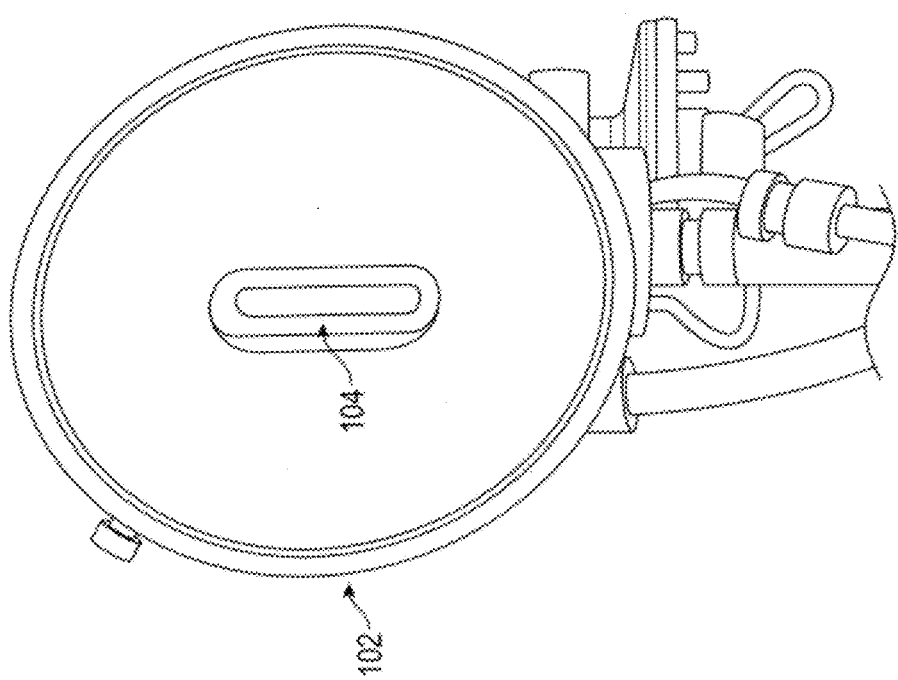

FIG. 1B is a bottom view of the therapy transducer 102 and the imaging system 104. As shown, the imaging system can be positioned in the center of the therapy transducer. However, other embodiments can include the imaging system positioned in other locations within the therapy transducer, or even directly integrated into the therapy transducer. In some embodiments, the imaging system is configured to produce real-time imaging at a focal point of the therapy transducer.

The histotripsy system may comprise one or more of various sub-systems, including a Therapy sub-system that can create, apply, focus and deliver acoustic cavitation/histotripsy through one or more therapy transducers, Integrated Imaging sub-system (or connectivity to) allowing real-time visualization of the treatment site and histotripsy effect through-out the procedure, a Robotics positioning sub-system to mechanically and/or electronically steer the therapy transducer, further enabled to connect/support or interact with a Coupling sub-system to allow acoustic coupling between the therapy transducer and the patient, and Software to communicate, control and interface with the system and computer-based control systems (and other external systems) and various Other Components, Ancillaries and Accessories, including one or more user interfaces and displays, and related guided work-flows, all working in part or together. The system may further comprise various fluidics and fluid management components, including but not limited to, pumps, valve and flow controls, temperature and degassing controls, and irrigation and aspiration capabilities, as well as providing and storing fluids. It may also contain various power supplies and protectors.

Cart

The Cart 110 may be generally configured in a variety of ways and form factors based on the specific uses and procedures. In some cases, systems may comprise multiple Carts, configured with similar or different arrangements. In some embodiments, the cart may be configured and arranged to be used in a radiology environment and in some cases in concert with imaging (e.g., CT, cone beam CT and/or MRI scanning). In other embodiments, it may be arranged for use in an operating room and a sterile environment, or in a robotically enabled operating room, and used alone, or as part of a surgical robotics procedure wherein a surgical robot conducts specific tasks before, during or after use of the system and delivery of acoustic cavitation/histotripsy. As such and depending on the procedure environment based on the aforementioned embodiments, the cart may be positioned to provide sufficient work-space and access to various anatomical locations on the patient (e.g., torso, abdomen, flank, head and neck, etc.), as well as providing work-space for other systems (e.g., anesthesia cart, laparoscopic tower, surgical robot, endoscope tower, etc.).

The Cart may also work with a patient surface (e.g., table or bed) to allow the patient to be presented and repositioned in a plethora of positions, angles and orientations, including allowing changes to such to be made pre, peri and post-procedurally. It may further comprise the ability to interface and communicate with one or more external imaging or image data management and communication systems, not limited to ultrasound, CT, fluoroscopy, cone beam CT, PET, PET/CT, MRI, optical, ultrasound, and image fusion and or image flow, of one or more modalities, to support the procedures and/or environments of use, including physical/mechanical interoperability (e.g., compatible within cone beam CT work-space for collecting imaging data pre, peri and/or post histotripsy).

In some embodiments one or more Carts may be configured to work together. As an example, one Cart may comprise a bedside mobile Cart equipped with one or more Robotic arms enabled with a Therapy transducer, and Therapy generator/amplifier, etc., while a companion cart working in concert and at a distance of the patient may comprise Integrated Imaging and a console/display for controlling the Robotic and Therapy facets, analogous to a surgical robot and master/slave configurations.

In some embodiments, the system may comprise a plurality of Carts, all slave to one master Cart, equipped to conduct acoustic cavitation procedures. In some arrangements and cases, one Cart configuration may allow for storage of specific sub-systems at a distance reducing operating room clutter, while another in concert Cart may comprise essentially bedside sub-systems and componentry (e.g., delivery system and therapy).

One can envision a plethora of permutations and configurations of Cart design, and these examples are in no way limiting the scope of the disclosure.

Histotripsy

Histotripsy comprises short, high amplitude, focused ultrasound pulses to generate a dense, energetic, "bubble cloud", capable of the targeted fractionation and destruction of tissue. Histotripsy is capable of creating controlled tissue erosion when directed at a tissue interface, including tissue/fluid interfaces, as well as well-demarcated tissue fractionation and destruction, at sub-cellular levels, when it is targeted at bulk tissue. Unlike other forms of ablation, including thermal and radiation-based modalities, histotripsy does not rely on heat or ionizing (high) energy to treat tissue. Instead, histotripsy uses acoustic cavitation generated at the focus to mechanically effect tissue structure, and in some cases liquefy, suspend, solubilize and/or destruct tissue into sub-cellular components.

Histotripsy can be applied in various forms, including: 1) Intrinsic-Threshold Histotripsy: Delivers pulses with a 1-2 cycles of high amplitude negative/tensile phase pressure exceeding the intrinsic threshold to generate cavitation in the medium (e.g., ~24-28 MPa for water-based soft tissue), 2) Shock-Scattering Histotripsy: Delivers typically pulses 3-20 cycles in duration. The shockwave (positive/compressive phase) scattered from an initial individual microbubble generated forms inverted shockwave, which constructively interfere with the incoming negative/tensile phase to form high amplitude negative/rarefactional phase exceeding the intrinsic threshold. In this way, a cluster of cavitation microbubbles is generated. The amplitude of the tensile phases of the pulses is sufficient to cause bubble nuclei in the medium to undergo inertial cavitation within the focal zone throughout the duration of the pulse. These nuclei scatter the incident shockwaves, which invert and constructively interfere with the incident wave to exceed the threshold for intrinsic nucleation, and 3) Boiling Histotripsy: Employs pulses roughly 1-20 ms in duration. Absorption of the shocked pulse rapidly heats the medium, thereby reducing the threshold for intrinsic nuclei. Once this intrinsic threshold coincides with the peak negative pressure of the incident wave, boiling bubbles form at the focus.

The large pressure generated at the focus causes a cloud of acoustic cavitation bubbles to form above certain thresholds, which creates localized stress and strain in the tissue and mechanical breakdown without significant heat deposition. At pressure levels where cavitation is not generated, minimal effect is observed on the tissue at the focus. This cavitation effect is observed only at pressure levels significantly greater than those which define the inertial cavitation threshold in water for similar pulse durations, on the order of 10 to 30 MPa peak negative pressure.

Histotripsy may be performed in multiple ways and under different parameters. It may be performed totally non-invasively by acoustically coupling a focused ultrasound transducer over the skin of a patient and transmitting acoustic pulses transcutaneously through overlying (and intervening) tissue to the focal zone (treatment zone and site). It may be further targeted, planned, directed and observed under direct visualization, via ultrasound imaging, given the bubble clouds generated by histotripsy may be visible as highly dynamic, echogenic regions on, for example, B Mode ultrasound images, allowing continuous visualization through its use (and related procedures). Likewise, the treated and fractionated tissue shows a dynamic change in echogenicity (typically a reduction), which can be used to evaluate, plan, observe and monitor treatment.

Generally, in histotripsy treatments, ultrasound pulses with 1 or more acoustic cycles are applied, and the bubble cloud formation relies on the pressure release scattering of the positive shock fronts (sometimes exceeding 100 MPa, P+) from initially initiated, sparsely distributed bubbles (or a single bubble). This is referred to as the "shock scattering mechanism".

This mechanism depends on one (or a few sparsely distributed) bubble(s) initiated with the initial negative half cycle(s) of the pulse at the focus of the transducer. A cloud of microbubbles then forms due to the pressure release backscattering of the high peak positive shock fronts from these sparsely initiated bubbles. These back-scattered high-amplitude rarefactional waves exceed the intrinsic threshold thus producing a localized dense bubble cloud. Each of the following acoustic cycles then induces further cavitation by the backscattering from the bubble cloud surface, which grows towards the transducer. As a result, an elongated dense bubble cloud growing along the acoustic axis opposite the ultrasound propagation direction is observed with the shock scattering mechanism. This shock scattering process makes the bubble cloud generation not only dependent on the peak negative pressure, but also the number of acoustic cycles and the amplitudes of the positive shocks. Without at least one intense shock front developed by nonlinear propagation, no dense bubble clouds are generated when the peak negative half-cycles are below the intrinsic threshold.

When ultrasound pulses less than 2 cycles are applied, shock scattering can be minimized, and the generation of a dense bubble cloud depends on the negative half cycle(s) of the applied ultrasound pulses exceeding an "intrinsic threshold" of the medium. This is referred to as the "intrinsic threshold mechanism".

This threshold can be in the range of 26-30 MPa for soft tissues with high water content, such as tissues in the human body. In some embodiments, using this intrinsic threshold mechanism, the spatial extent of the lesion may be well-defined and more predictable. With peak negative pressures (P−) not significantly higher than this threshold, sub-wavelength reproducible lesions as small as half of the −6 dB beam width of a transducer may be generated.

With high-frequency Histotripsy pulses, the size of the smallest reproducible lesion becomes smaller, which is beneficial in applications that require precise lesion generation. However, high-frequency pulses are more susceptible to attenuation and aberration, rendering problematical treatments at a larger penetration depth (e.g., ablation deep in the body) or through a highly aberrative medium (e.g., transcranial procedures, or procedures in which the pulses are transmitted through bone(s)). Histotripsy may further also be applied as a low-frequency "pump" pulse (typically <2 cycles and having a frequency between 100 kHz and 1 MHz) can be applied together with a high-frequency "probe" pulse (typically <2 cycles and having a frequency greater than 2 MHz, or ranging between 2 MHz and 10 MHz) wherein the peak negative pressures of the low and high-frequency pulses constructively interfere to exceed the intrinsic threshold in the target tissue or medium. The low-frequency pulse, which is more resistant to attenuation and aberration, can raise the peak negative pressure P− level for a region of interest (ROI), while the high-frequency pulse, which provides more precision, can pinpoint a targeted location within the ROI and raise the peak negative pressure P− above the intrinsic threshold. This approach may be referred to as "dual frequency", "dual beam histotripsy" or "parametric histotripsy."

Additional systems, methods and parameters to deliver optimized histotripsy, using shock scattering, intrinsic threshold, and various parameters enabling frequency compounding and bubble manipulation, are herein included as part of the system and methods disclosed herein, including additional means of controlling said histotripsy effect as pertains to steering and positioning the focus, and concurrently managing tissue effects (e.g., prefocal thermal collateral damage) at the treatment site or within intervening tissue. Further, it is disclosed that the various systems and methods, which may include a plurality of parameters, such as but not limited to, frequency, operating frequency, center frequency, pulse repetition frequency, pulses, bursts, number of pulses, cycles, length of pulses, amplitude of pulses, pulse period, delays, burst repetition frequency, sets of the former, loops of multiple sets, loops of multiple and/or different sets, sets of loops, and various combinations or permutations of, etc., are included as a part of this disclosure, including future envisioned embodiments of such.

Therapy Components

The Therapy sub-system may work with other sub-systems to create, optimize, deliver, visualize, monitor and control acoustic cavitation, also referred to herein and in following as "histotripsy", and its derivatives of, including boiling histotripsy and other thermal high frequency ultrasound approaches. It is noted that the disclosed inventions may also further benefit other acoustic therapies that do not comprise a cavitation, mechanical or histotripsy component. The therapy sub-system can include, among other features, an ultrasound therapy transducer and a pulse generator system configured to deliver ultrasound pulses into tissue.

In order to create and deliver histotripsy and derivatives of histotripsy, the therapy sub-system may also comprise components, including but not limited to, one or more function generators, amplifiers, therapy transducers and power supplies.

The therapy transducer can comprise a single element or multiple elements configured to be excited with high amplitude electric pulses (>1000V or any other voltage that can cause harm to living organisms). The amplitude necessary to drive the therapy transducers for Histotripsy vary depending on the design of the transducer and the materials used (e.g., solid or polymer/piezoelectric composite including ceramic or single crystal) and the transducer center frequency which is directly proportional to the thickness of the piezoelectric material. Transducers therefore operating at a high frequency require lower voltage to produce a given surface pressure than is required by low frequency therapy transducers. In some embodiments, the transducer elements are formed using a piezoelectric-polymer composite material or a solid piezoelectric material. Further, the piezoelectric material can be of polycrystalline/ceramic or single crystalline formulation. In some embodiments the transducer elements can be formed using silicon using MEMs technology, including CMUT and PMUT designs.

In some embodiments, the function generator may comprise a field programmable gate array (FPGA) or other suitable function generator. The FPGA may be configured with parameters disclosed previously herein, including but not limited to frequency, pulse repetition frequency, bursts, burst numbers, where bursts may comprise pulses, numbers of pulses, length of pulses, pulse period, delays, burst repetition frequency or period, where sets of bursts may comprise a parameter set, where loop sets may comprise various parameter sets, with or without delays, or varied delays, where multiple loop sets may be repeated and/or new loop sets introduced, of varied time delay and independently controlled, and of various combinations and permutations of such, overall and throughout.

In some embodiments, the generator or amplifier may be configured to be a universal single-cycle or multi-cycle pulse generator, and to support driving via Class D or inductive driving, as well as across all envisioned clinical applications, use environments, also discussed in part later in this disclosure. In other embodiments, the class D or inductive current driver may be configured to comprise transformer and/or auto-transformer driving circuits to further provide step up/down components, and in some cases, to preferably allow a step up in the amplitude. They may also comprise specific protective features, to further support the system, and provide capability to protect other parts of the system (e.g., therapy transducer and/or amplifier circuit components) and/or the user, from various hazards, including but not limited to, electrical safety hazards, which may potentially lead to use environment, system and therapy system, and user harms, damage or issues.

Disclosed generators may allow and support the ability of the system to select, vary and control various parameters (through enabled software tools), including, but not limited to those previously disclosed, as well as the ability to start/stop therapy, set and read voltage level, pulse and/or burst repetition frequency, number of cycles, duty ratio, channel enabled and delay, etc., modulate pulse amplitude on a fast time-scale independent of a high voltage supply, and/or other service, diagnostic or treatment features.

In some embodiments, the Therapy sub-system and/or components of, such as the amplifier, may comprise further integrated computer processing capability and may be networked, connected, accessed, and/or be removable/portable, modular, and/or exchangeable between systems, and/or driven/commanded from/by other systems, or in various combinations. Other systems may include other acoustic cavitation/histotripsy, HIFU, HITU, radiation therapy, radiofrequency, microwave, and cryoablation systems, navigation and localization systems, laparoscopic, single incision/single port, endoscopic and non-invasive surgical robots, laparoscopic or surgical towers comprising other energy-based or vision systems, surgical system racks or booms, imaging carts, etc.

In some embodiments, one or more amplifiers may comprise a Class D amplifier and related drive circuitry including matching network components. Depending on the transducer element electric impedance and choice of the matching network components (e.g., an LC circuit made of an inductor L1 in series and the capacitor C1 in parallel), the combined impedance can be aggressively set low in order to have high amplitude electric waveform necessary to drive the transducer element. The maximum amplitude that Class D amplifiers is dependent on the circuit components used, including the driving MOSFET/IGBT transistors, matching network components or inductor, and transformer or auto-transformer, and of which may be typically in the low kV (e.g., 1-3 kV) range.

Therapy transducer element(s) are excited with an electrical waveform with an amplitude (voltage) to produce a pressure output sufficient for Histotripsy therapy. The excitation electric field can be defined as the necessary waveform voltage per thickness of the piezoelectric element. For example, because a piezoelectric element operating at 1 MHz transducer is half the thickness of an equivalent 500 kHz element, it will require half the voltage to achieve the same electric field and surface pressure.

To sufficiently drive therapy transducers for histotripsy therapy, in other embodiments, the amplifier may be required to produce voltages that exceed operational limits of conventional amplifier circuit components. For example, an inductive driver circuit can be provided that is configured to excite ultrasound transducers for histotripsy therapy. With an inductive driver circuit, therapy transducer elements can be driven up to approximately 3 kV peak-positive or up to about 4.5 kV peak-to-peak. These voltages may, for example, be adequate for a therapy transducer operating at 1 MHz but not sufficient for a 500 kHz transducer. The maximum driving voltage in this example of the inductive driver is limited by the maximum operating voltage of the IGBT transistor Q1 and its switching time. The IGBT transistor with best performance for the inductive driving circuit currently available is rated for maximum of 3 kV. It should be understood that this driving voltage can improve as advances in transistors are made.

An inductive driver circuit described above also offers many advantages to higher frequency transducers, including the ability to produce smaller/more precise bubble clouds (i.e., microtripsy), producing a reduced thermal effect in tissue, etc.

The Therapy sub-system may also comprise therapy transducers of various designs and working parameters, supporting use in various procedures (and procedure settings). Systems may be configured with one or more therapy transducers, that may be further interchangeable, and work with various aspects of the system in similar or different ways (e.g., may interface to a robotic arm using a common interface and exchange feature, or conversely, may adapt to work differently with application specific imaging probes, where different imaging probes may interface and integrate with a therapy transducer in specifically different ways).

Therapy transducers may be configured of various parameters that may include size, shape (e.g., rectangular or round; anatomically curved housings, etc.), geometry, focal length, number of elements, size of elements, distribution of elements (e.g., number of rings, size of rings for annular patterned transducers), frequency, enabling electronic beam steering, etc. Transducers may be composed of various materials (e.g., piezoelectric, silicon, etc.), form factors and types (e.g., machined elements, chip-based, etc.) and/or by various methods of fabrication.

Transducers may be designed and optimized for clinical applications (e.g., abdominal tumors, peripheral vascular disease, fat ablation, etc.) and desired outcomes (e.g., acoustic cavitation/histotripsy without thermal injury to intervening tissue), and affording a breadth of working ranges, including relatively shallow and superficial targets (e.g., thyroid or breast nodules), versus, deeper or harder to reach targets, such as central liver or brain tumors. They may be configured to enable acoustic cavitation/histotripsy under various parameters and sets of, as enabled by the aforementioned system components (e.g., function generator and amplifier, etc.), including but not limited to frequency, pulse repetition rate, pulses, number of pulses, pulse length, pulse period, delays, repetitions, sync delays, sync period, sync pulses, sync pulse delays, various loop sets, others, and permutations.

Integrated Imaging

The disclosed system may comprise various imaging modalities to allow users to visualize, monitor and collect/use feedback of the patient's anatomy, related regions of interest and treatment/procedure sites, as well as surrounding and intervening tissues to assess, plan and conduct procedures, and adjust treatment parameters as needed. Imaging modalities may comprise various ultrasound, x-ray, CT, MRI, PET, fluoroscopy, optical, contrast or agent enhanced versions, and/or various combinations of. It is further disclosed that various image processing and characterization technologies may also be utilized to afford enhanced visualization and user decision making. These may be selected or commanded manually by the user or in an automated fashion by the system. The system may be configured to allow side by side, toggling, overlays, 3D reconstruction, segmentation, registration, multi-modal image fusion, image flow, and/or any methodology affording the user to identify, define and inform various aspects of using imaging during the procedure, as displayed in the various system user interfaces and displays. Examples may include locating, displaying and characterizing regions of interest, organ systems, potential treatment sites within, with on and/or surrounding organs or tissues, identifying critical structures such as ducts, vessels, nerves, ureters, fissures, capsules, tumors, tissue trauma/injury/disease, other organs, connective tissues, etc., and/or in context to one another, of one or more (e.g., tumor draining lymphatics or vasculature; or tumor proximity to organ capsule or underlying other organ), as unlimited examples.

Systems may be configured to include onboard integrated imaging hardware, software, sensors, probes and wetware, and/or may be configured to communicate and interface with external imaging and image processing systems. The aforementioned components may be also integrated into the system's Therapy sub-system components wherein probes, imaging arrays, or the like, and electrically, mechanically or electromechanically integrated into therapy transducers. This may afford, in part, the ability to have geometrically aligned imaging and therapy, with the therapy directly within the field of view, and in some cases in line, with imaging. In some embodiments, this integration may comprise a fixed orientation of the imaging capability (e.g., imaging probe) in context to the therapy transducer. In other embodiments, the imaging solution may be able to move or adjust its position, including modifying angle, extension (e.g., distance from therapy transducer or patient), rotation (e.g., imaging plane in example of an ultrasound probe)

and/or other parameters, including moving/adjusting dynamically while actively imaging. The imaging component or probe may be encoded so its orientation and position relative to another aspect of the system, such as the therapy transducer, and/or robotically-enabled positioning component may be determined.

In one embodiment, the system may comprise onboard ultrasound, further configured to allow users to visualize, monitor and receive feedback for procedure sites through the system displays and software, including allowing ultrasound imaging and characterization (and various forms of), ultrasound guided planning and ultrasound guided treatment, all in real-time. The system may be configured to allow users to manually, semi-automated or in fully automated means image the patient (e.g., by hand or using a robotically-enabled imager).

In some embodiments, imaging feedback and monitoring can include monitoring changes in: backscatter from bubble clouds; speckle reduction in backscatter; backscatter speckle statistics; mechanical properties of tissue (i.e., elastography); tissue perfusion (i.e., ultrasound contrast); shear wave propagation; acoustic emissions, electrical impedance tomography, and/or various combinations of, including as displayed or integrated with other forms of imaging (e.g., CT or MRI).

In some embodiments, imaging including feedback and monitoring from backscatter from bubble clouds, may be used as a method to determine immediately if the histotripsy process has been initiated, is being properly maintained, or even if it has been extinguished. For example, this method enables continuously monitored in real time drug delivery, tissue erosion, and the like. The method also can provide feedback permitting the histotripsy process to be initiated at a higher intensity and maintained at a much lower intensity. For example, backscatter feedback can be monitored by any transducer or ultrasonic imager. By measuring feedback for the therapy transducer, an accessory transducer can send out interrogation pulses or be configured to passively detect cavitation. Moreover, the nature of the feedback received can be used to adjust acoustic parameters (and associated system parameters) to optimize the drug delivery and/or tissue erosion process.

In some embodiments, imaging including feedback and monitoring from backscatter, and speckle reduction, may be configured in the system.

For systems comprising feedback and monitoring via backscattering, and as means of background, as tissue is progressively mechanically subdivided, in other words homogenized, disrupted, or eroded tissue, this process results in changes in the size and distribution of acoustic scatter. At some point in the process, the scattering particle size and density is reduced to levels where little ultrasound is scattered, or the amount scattered is reduced significantly. This results in a significant reduction in speckle, which is the coherent constructive and destructive interference patterns of light and dark spots seen on images when coherent sources of illumination are used; in this case, ultrasound. After some treatment time, the speckle reduction results in a dark area in the therapy volume. Since the amount of speckle reduction is related to the amount of tissue subdivision, it can be related to the size of the remaining tissue fragments. When this size is reduced to sub-cellular levels, no cells are assumed to have survived. So, treatment can proceed until a desired speckle reduction level has been reached. Speckle is easily seen and evaluated on standard ultrasound imaging systems. Specialized transducers and systems, including those disclosed herein, may also be used to evaluate the backscatter changes.

Further, systems comprising feedback and monitoring via speckle, and as means of background, an image may persist from frame to frame and change very little as long as the scatter distribution does not change and there is no movement of the imaged object. However, long before the scatters are reduced enough in size to cause speckle reduction, they may be changed sufficiently to be detected by signal processing and other means. This family of techniques can operate as detectors of speckle statistics changes. For example, the size and position of one or more speckles in an image will begin to decorrelate before observable speckle reduction occurs. Speckle decorrelation, after appropriate motion compensation, can be a sensitive measure of the mechanical disruption of the tissues, and thus a measure of therapeutic efficacy. This feedback and monitoring technique may permit early observation of changes resulting from the acoustic cavitation/histotripsy process and can identify changes in tissue before substantial or complete tissue effect (e.g., erosion occurs). In one embodiment, this method may be used to monitor the acoustic cavitation/histotripsy process for enhanced drug delivery where treatment sites/tissue is temporally disrupted, and tissue damage/erosion is not desired. In other embodiments, this may comprise speckle decorrelation by movement of scatters in an increasingly fluidized therapy volume. For example, in the case where partial or complete tissue erosion is desired.

For systems comprising feedback and monitoring via elastography, and as means of background, as treatment sites/tissue are further subdivided per an acoustic cavitation/histotripsy effect (homogenized, disrupted, or eroded), its mechanical properties change from a soft but interconnected solid to a viscous fluid or paste with few long-range interactions. These changes in mechanical properties can be measured by various imaging modalities including MRI and ultrasound imaging systems. For example, an ultrasound pulse can be used to produce a force (i.e., a radiation force) on a localized volume of tissue. The tissue response (displacements, strains, and velocities) can change significantly during histotripsy treatment allowing the state of tissue disruption to be determined by imaging or other quantitative means.

Systems may also comprise feedback and monitoring via shear wave propagation changes. As means of background, the subdivision of tissues makes the tissue more fluid and less solid and fluid systems generally do not propagate shear waves. Thus, the extent of tissue fluidization provides opportunities for feedback and monitoring of the histotripsy process. For example, ultrasound and MRI imaging systems can be used to observe the propagation of shear waves. The extinction of such waves in a treated volume is used as a measure of tissue destruction or disruption. In one system embodiment, the system and supporting sub-systems may be used to generate and measure the interacting shear waves. For example, two adjacent ultrasound foci might perturb tissue by pushing it in certain ways. If adjacent foci are in a fluid, no shear waves propagate to interact with each other. If the tissue is not fluidized, the interaction would be detected with external means, for example, by a difference frequency only detected when two shear waves interact nonlinearly, with their disappearance correlated to tissue damage. As such, the system may be configured to use this modality to enhance feedback and monitoring of the acoustic cavitation/histotripsy procedure.

For systems comprising feedback and monitoring via acoustic emission, and as means of background, as a tissue volume is subdivided, its effect on acoustic cavitation/histotripsy (e.g., the bubble cloud here) is changed. For example, bubbles may grow larger and have a different lifetime and collapse changing characteristics in intact versus fluidized tissue. Bubbles may also move and interact after tissue is subdivided producing larger bubbles or cooperative interaction among bubbles, all of which can result in changes in acoustic emission. These emissions can be heard during treatment and they change during treatment. Analysis of these changes, and their correlation to therapeutic efficacy, enables monitoring of the progress of therapy, and may be configured as a feature of the system.

For systems comprising feedback and monitoring via electrical impedance tomography, and as means of background, an impedance map of a therapy site can be produced based upon the spatial electrical characteristics throughout the therapy site. Imaging of the conductivity or permittivity of the therapy site of a patient can be inferred from taking skin surface electrical measurements. Conducting electrodes are attached to a patient's skin and small alternating currents are applied to some or all of the electrodes. One or more known currents are injected into the surface and the voltage is measured at a number of points using the electrodes. The process can be repeated for different configurations of applied current. The resolution of the resultant image can be adjusted by changing the number of electrodes employed. A measure of the electrical properties of the therapy site within the skin surface can be obtained from the impedance map, and changes in and location of the acoustic cavitation/histotripsy (e.g., bubble cloud, specifically) and histotripsy process can be monitored using this as configured in the system and supporting sub-systems.

The user may be allowed to further select, annotate, mark, highlight, and/or contour, various regions of interest or treatment sites, and defined treatment targets (on the image(s)), of which may be used to command and direct the system where to image, test and/or treat, through the system software and user interfaces and displays. In some arrangements, the user may use a manual ultrasound probe (e.g., diagnostic hand-held probe) to conduct the procedure. In another arrangement, the system may use a robot and/or electromechanical positioning system to conduct the procedure, as directed and/or automated by the system, or conversely, the system can enable combinations of manual and automated uses.

The system may further include the ability to conduct image registration, including imaging and image data set registration to allow navigation and localization of the system to the patient, including the treatment site (e.g., tumor, critical structure, bony anatomy, anatomy and identifying features of, etc.). In one embodiment, the system allows the user to image and identify a region of interest, for example the liver, using integrated ultrasound, and to select and mark a tumor (or surrogate marker of) comprised within the liver through/displayed in the system software, and wherein said system registers the image data to a coordinate system defined by the system, that further allows the system's Therapy and Robotics sub-systems to deliver synchronized acoustic cavitation/histotripsy to said marked tumor. The system may comprise the ability to register various image sets, including those previously disclosed, to one another, as well as to afford navigation and localization (e.g., of a therapy transducer to a CT or MRI/ultrasound fusion image with the therapy transducer and Robotics sub-system tracking to said image).

The system may also comprise the ability to work in a variety of interventional, endoscopic and surgical environments, including alone and with other systems (surgical/laparoscopic towers, vision systems, endoscope systems and towers, ultrasound enabled endoscopic ultrasound (flexible and rigid), percutaneous/endoscopic/laparoscopic and minimally invasive navigation systems (e.g., optical, electromagnetic, shape-sensing, ultrasound-enabled, etc.), of also which may work with, or comprise various optical imaging capabilities (e.g., fiber and or digital). The disclosed system may be configured to work with these systems, in some embodiments working alongside them in concert, or in other embodiments where all or some of the system may be integrated into the above systems/platforms (e.g., acoustic cavitation/histotripsy-enabled endoscope system or laparoscopic surgical robot). In many of these environments, a therapy transducer may be utilized at or around the time of use, for example, of an optically guided endoscope/bronchoscope, or as another example, at the time a laparoscopic robot (e.g., Intuitive Da Vinci*Xi system) is viewing/manipulating a tissue/treatment site. Further, these embodiments and examples may include where said other systems/platforms are used to deliver (locally) fluid to enable the creation of a man-made acoustic window, where on under normal circumstances may not exist (e.g., fluidizing a segment or lobe of the lung in preparation for acoustic cavitation/histotripsy via non-invasive transthoracic treatment (e.g., transducer externally placed on/around patient). Systems disclosed herein may also comprise all or some of their sub-system hardware packaged within the other system cart/console/systems described here (e.g., acoustic cavitation/histotripsy system and/or sub-systems integrated and operated from said navigation or laparoscopic system).

The system may also be configured, through various aforementioned parameters and other parameters, to display real-time visualization of a bubble cloud in a spatial-temporal manner, including the resulting tissue effect peri/post-treatment from tissue/bubble cloud interaction, wherein the system can dynamically image and visualize, and display, the bubble cloud, and any changes to it (e.g., decreasing or increasing echogenicity), which may include intensity, shape, size, location, morphology, persistence, etc. These features may allow users to continuously track and follow the treatment in real-time in one integrated procedure and interface/system, and confirm treatment safety and efficacy on the fly (versus other interventional or surgical modalities, which either require multiple procedures to achieve the same, or where the treatment effect is not visible in real-time (e.g., radiation therapy), or where it is not possible to achieve such (e.g., real-time visualization of local tissue during thermal ablation), and/or where the other procedure further require invasive approaches (e.g., incisions or punctures) and iterative imaging in a scanner between procedure steps (e.g., CT or MRI scanning). The above disclosed systems, sub-systems, components, modalities, features and work-flows/methods of use may be implemented in an unlimited fashion through enabling hardware, software, user interfaces and use environments, and future improvements, enhancements and inventions in this area are considered as included in the scope of this disclosure, as well as any of the resulting data and means of using said data for analytics, artificial intelligence or digital health applications and systems.

Robotics

The system may comprise various Robotic sub-systems and components, including but not limited to, one or more robotic arms and controllers, which may further work with other sub-systems or components of the system to deliver and monitor acoustic cavitation/histotripsy. As previously discussed herein, robotic arms and control systems may be integrated into one or more Cart configurations.

For example, one system embodiment may comprise a Cart with an integrated robotic arm and control system, and Therapy, Integrated Imaging and Software, where the robotic arm and other listed sub-systems are controlled by the user through the form factor of a single bedside Cart.

In other embodiments, the Robotic sub-system may be configured in one or more separate Carts, that may be a driven in a master/slave configuration from a separate master or Cart, wherein the robotically-enabled Cart is positioned bed/patient-side, and the Master is at a distance from said Cart.

Disclosed robotic arms may be comprised of a plurality of joints, segments, and degrees of freedom and may also include various integrated sensor types and encoders, implemented for various use and safety features. Sensing technologies and data may comprise, as an example, vision, potentiometers, position/localization, kinematics, force, torque, speed, acceleration, dynamic loading, and/or others. In some cases, sensors may be used for users to direct robot commands (e.g., hand gesture the robot into a preferred set up position, or to dock home). Additional details on robotic arms can be found in US Patent Pub. No. 2013/0255426 to Kassow et al. which is disclosed herein by reference in its entirety.

The robotic arm receives control signals and commands from the robotic control system, which may be housed in a Cart. The system may be configured to provide various functionalities, including but not limited to, position, tracking, patterns, triggering, and events/actions.

Position may be configured to comprise fixed positions, pallet positions, time-controlled positions, distance-controlled positions, variable-time controlled positions, variable-distance controlled positions.

Tracking may be configured to comprise time-controlled tracking and/or distance-controlled tracking.

The patterns of movement may be configured to comprise intermediate positions or waypoints, as well as sequence of positions, through a defined path in space.

Triggers may be configured to comprise distance measuring means, time, and/or various sensor means including those disclosed herein, and not limited to, visual/imaging-based, force, torque, localization, energy/power feedback and/or others.

Events/actions may be configured to comprise various examples, including proximity-based (approaching/departing a target object), activation or de-activation of various end-effectors (e.g., therapy transducers), starting/stopping/pausing sequences of said events, triggering or switching between triggers of events/actions, initiating patterns of movement and changing/toggling between patterns of movement, and/or time-based and temporal over the defined work and time-space.

In one embodiment, the system comprises a three degree of freedom robotic positioning system, enabled to allow the user (through the software of the system and related user interfaces), to micro-position a therapy transducer through X, Y, and Z coordinate system, and where gross macro-positioning of the transducer (e.g., aligning the transducer on the patient's body) is completed manually. In some embodiments, the robot may comprise 6 degrees of freedom including X, Y, Z, and pitch, roll and yaw. In other embodiments, the Robotic sub-system may comprise further degrees of freedom, that allow the robot arm supporting base to be positioned along a linear axis running parallel to the general direction of the patient surface, and/or the supporting base height to be adjusted up or down, allowing the position of the robotic arm to be modified relative to the patient, patient surface, Cart, Coupling sub-system, additional robots/robotic arms and/or additional surgical systems, including but not limited to, surgical towers, imaging systems, endoscopic/laparoscopic systems, and/or other.

One or more robotic arms may also comprise various features to assist in maneuvering and modifying the arm position, manually or semi-manually, and of which said features may interface on or between the therapy transducer and the most distal joint of the robotic arm. In some embodiments, the feature is configured to comprise a handle allowing maneuvering and manual control with one or more hands. The handle may also be configured to include user input and electronic control features of the robotic arm, to command various drive capabilities or modes, to actuate the robot to assist in gross or fine positioning of the arm (e.g., activating or deactivating free drive mode). The work-flow for the initial positioning of the robotic arm and therapy head can be configured to allow either first positioning the therapy transducer/head in the coupling solution, with the therapy transducer directly interfaced to the arm, or in a different work-flow, allowing the user to set up the coupling solution first, and enabling the robot arm to be interfaced to the therapy transducer/coupling solution as a later/terminal set up step.

In some embodiments, the robotic arm may comprise a robotic arm on a laparoscopic, single port, endoscopic, hybrid or combination of, and/or other robot, wherein said robot of the system may be a slave to a master that controls said arm, as well as potentially a plurality of other arms, equipped to concurrently execute other tasks (vision, imaging, grasping, cutting, ligating, sealing, closing, stapling, ablating, suturing, marking, etc.), including actuating one or more laparoscopic arms (and instruments) and various histotripsy system components. For example, a laparoscopic robot may be utilized to prepare the surgical site, including manipulating organ position to provide more ideal acoustic access and further stabilizing said organ in some cases to minimize respiratory motion. In conjunction and parallel to this, a second robotic arm may be used to deliver non-invasive acoustic cavitation through a body cavity, as observed under real-time imaging from the therapy transducer (e.g., ultrasound) and with concurrent visualization via a laparoscopic camera. In other related aspects, a similar approach may be utilized with a combination of an endoscopic and non-invasive approach, and further, with a combination of an endoscopic, laparoscopic and non-invasive approach.

Coupling

Systems may comprise a variety of Coupling sub-system embodiments, of which are enabled and configured to allow acoustic coupling to the patient to afford effective acoustic cavitation/histotripsy (e.g., provide acoustic medium between transducer and patient, and support of). These may include different form factors of such, including open and enclosed solutions, and some arrangements which may be configured to allow dynamic control over the acoustic medium (e.g., temperature, dissolved gas content, level of particulate filtration, sterility, etc.). Such dynamic control components may be directly integrated to the system (within the Cart), or may be in communication with the system, but externally situated.

The Coupling sub-system typically comprises, at a minimum, coupling medium, a reservoir/container to contain said coupling medium, and a support structure. In most embodiments, the coupling medium is water, and wherein the water may be conditioned before or during the procedure (e.g., chilled, degassed, filtered, etc.). Various conditioning parameters may be employed based on the configuration of the system and its intended use/application.

The reservoir or medium container may be formed and shaped to adapt/conform to the patient, allow the therapy transducer to engage and work within the acoustic medium, per defined and required working space (minimum volume of medium to allow the therapy transducer to be positioned and/or move through one or more treatment positions or patterns, and at various standoffs or depths from the patient, etc.), and wherein said reservoir or medium container may also mechanically support the load, and distribution of the load, through the use of a mechanical and/or electromechanical support structure. The container may be of various shapes, sizes, curvatures, and dimensions, and may be comprised of a variety of materials (single, multiple, composites, etc.), of which may vary throughout. In some embodiments, it may comprise features such as films, drapes, membranes, bellows, etc. that may be insertable and removable, and/or fabricated within. It may further contain various sensors, drains, lighting (e.g., LEDs), markings, text, etc.

In one embodiment, the reservoir or medium container contains a sealable frame, of which a membrane and/or film may be positioned within, to afford a conformable means of contacting the reservoir (later comprising the therapy transducer) as an interface to the patient, that further provides a barrier to the medium (e.g., water) between the patient and transducer). In other embodiments, the membrane and/or film may comprise an opening, the edge of which affords mechanical sealing to the patient, but in contrast allows medium communication with the patient (e.g., direct water interface with patient). The superstructure of the reservoir or medium container in both these examples may further afford the proximal portion of the structure (e.g., top) to be open or enclosed (e.g., to prevent spillage or afford additional features).

Disclosed membranes may be comprised of various elastomers, viscoelastic polymers, thermoplastics, thermoset polymers, silicones, urethanes, rigid/flexible co-polymers, block co-polymers, random block co-polymers, etc. Materials may be hydrophilic, hydrophobic, surface modified, coated, extracted, etc., and may also contain various additives to enhance performance, appearance or stability.

Said materials may be formed into useful membranes through molding, casting, spraying, ultrasonic spraying and/or any other processing methodology that produces useful embodiments. They may be single use or reposable/reusable. They may be provided non-sterile, aseptically cleaned or sterile, where sterilization may comprise any known method, including but not limited to ethylene oxide, gamma, e-beam, autoclaving, steam, peroxide, plasma, chemical, etc.

Open reservoirs or medium containers may comprise various methods of filling, including using pre-prepared medium or water, that may be delivered into the such, in some cases to a defined specification of water (level of temperature and gas saturation, etc.), or they may comprise additional features integral to the design that allow filling and draining (e.g., ports, valves, hoses, tubing, fittings, bags, pumps, etc.).

Enclosed iterations of the reservoir or medium container may comprise various features for sealing, in some embodiments sealing to a proximal/top portion or structure of a reservoir/container, or in other cases where sealing may comprise embodiments that seal to the transducer, or a feature on the transducer housings. Further, some embodiments may comprise the dynamic ability to control the volume of fluid within these designs, to minimize the potential for air bubbles or turbulence in said fluid. As such, integrated features allowing fluid communication, and control of, may be provided (ability to provide/remove fluid on demand), including the ability to monitor and control various fluid parameters, some disclosed above. In order to provide this functionality, the overall system, and as part, the Coupling sub-system, may comprise a fluid conditioning system, which may contain various electromechanical devices, systems, power, sensing, computing and control systems, etc.

Coupling support systems may include various mechanical support devices to interface the reservoir/container and medium to the patient, and the workspace (e.g., bed). In some embodiments, the support system comprises a mechanical arm with 3 or more degrees of freedom. Said arm may interface with one or more locations (and features) of the bed, including but not limited to, the frame, rails, customized rails or inserts, as well as one or more locations of the reservoir or container. The arm may be a feature implemented on one or more Carts, wherein Carts may be configured in various unlimited permutations, in some cases where a Cart only comprises the role of supporting and providing the disclosed support structure.

In some embodiments, the support structure and arm may be a robotically-enabled arm, implemented as a stand-alone Cart, or integrated into a Cart further comprising two or more system sub-systems, or where in the robotically-enabled arm is an arm of another robot, of interventional, surgical or other type, and may further comprise various user input features to actuate/control the robotic arm (e.g., positioning into/within coupling medium) and/or Coupling solution features (e.g., filling, draining, etc.).

Software

The system may comprise various software applications, features and components which allow the user to interact, control and use the system for a plethora of clinical applications. The Software may communicate and work with one or more of the sub-systems, including but not limited to Therapy, Integrated Imaging, Robotics and Other Components, Ancillaries and Accessories of the system.

Overall, in no specific order of importance, the software may provide features and support to initialize and set up the system, service the system, communicate and import/export/store data, modify/manipulate/configure/control/command various settings and parameters by the user, mitigate safety and use-related risks, plan procedures, provide support to various configurations of transducers, robotic arms and drive systems, function generators and amplifier circuits/slaves, test and treatment ultrasound sequences, transducer steering and positioning (electromechanical and electronic beam steering, etc.), treatment patterns, support for imaging and imaging probes, manual and electromechanical/robotically-enabling movement of, imaging support for measuring/characterizing various dimensions within or around procedure and treatment sites (e.g., depth from one anatomical location to another, etc., pre-treatment assessments and protocols for measuring/characterizing in situ treatment site properties and conditions (e.g., acoustic cavitation/histotripsy thresholds and heterogeneity of), targeting and target alignment, calibration, marking/annotating, localizing/navigating, registering, guiding, providing and guiding through work-flows, procedure steps, executing treatment plans and protocols autonomously, autonomously and while under direct observation and viewing with real-time imaging as displayed through the software, including various views and viewports for viewing, communication tools (video, audio, sharing, etc.), troubleshooting, providing directions, warnings, alerts, and/or allowing communication through various networking devices and protocols. It is further envisioned that the software user interfaces and supporting displays may comprise various buttons, commands, icons, graphics, text, etc., that allow the user to interact with the system in a user-friendly and effective manner, and these may be presented in an unlimited number of permutations, layouts and designs, and displayed in similar or different manners or feature sets for systems that may comprise more than one display (e.g., touch screen monitor and touch pad), and/or may network to one or more external displays or systems (e.g., another robot, navigation system, system tower, console, monitor, touch display, mobile device, tablet, etc.).

The software, as a part of a representative system, including one or more computer processors, may support the various aforementioned function generators (e.g., FPGA), amplifiers, power supplies and therapy transducers. The software may be configured to allow users to select, determine and monitor various parameters and settings for acoustic cavitation/histotripsy, and upon observing/receiving feedback on performance and conditions, may allow the user to stop/start/modify said parameters and settings.

The software may be configured to allow users to select from a list or menu of multiple transducers and support the auto-detection of said transducers upon connection to the system (and verification of the appropriate sequence and parameter settings based on selected application). In other embodiments, the software may update the targeting and amplifier settings (e.g., channels) based on the specific transducer selection. The software may also provide transducer recommendations based on pre-treatment and planning inputs. Conversely, the software may provide error messages or warnings to the user if said therapy transducer, amplifier and/or function generator selections or parameters are erroneous, yield a fault or failure. This may further comprise reporting the details and location of such.

In addition to above, the software may be configured to allow users to select treatment sequences and protocols from a list or menu, and to store selected and/or previous selected sequences and protocols as associated with specific clinical uses or patient profiles. Related profiles may comprise any associated patient, procedure, clinical and/or engineering data, and may be used to inform, modify and/or guide current or future treatments or procedures/interventions, whether as decision support or an active part of a procedure itself (e.g., using serial data sets to build and guide new treatments).

As a part of planning or during the treatment, the software (and in working with other components of the system) may allow the user to evaluate and test acoustic cavitation/histotripsy thresholds at various locations in a user-selected region of interest or defined treatment area/volume, to determine the minimum cavitation thresholds throughout said region or area/volume, to ensure treatment parameters are optimized to achieve, maintain and dynamically control acoustic cavitation/histotripsy. In one embodiment, the system allows a user to manually evaluate and test threshold parameters at various points. Said points may include those at defined boundary, interior to the boundary and center locations/positions, of the selected region of interest and treatment area/volume, and where resulting threshold measurements may be reported/displayed to the user, as well as utilized to update therapy parameters before treatment. In another embodiment, the system may be configured to allow automated threshold measurements and updates, as enabled by the aforementioned Robotics sub-system, wherein the user may direct the robot, or the robot may be commanded to execute the measurements autonomously.

Software may also be configured, by working with computer processors and one or more function generators, amplifiers and therapy transducers, to allow various permutations of delivering and positioning optimized acoustic cavitation/histotripsy in and through a selected area/volume. This may include, but not limited to, systems configured with a fixed/natural focus arrangement using purely electromechanical positioning configuration(s), electronic beam steering (with or without electromechanical positioning), electronic beam steering to a new selected fixed focus with further electromechanical positioning, axial (Z axis) electronic beam steering with lateral (X and Y) electromechanical positioning, high speed axial electronic beam steering with lateral electromechanical positioning, high speed beam steering in 3D space, various combinations of including with dynamically varying one or more acoustic cavitation/histotripsy parameters based on the aforementioned ability to update treatment parameters based on threshold measurements (e.g., dynamically adjusting amplitude across the treatment area/volume).

Threshold Testing

The systems described herein include the capability to evaluate and test acoustic cavitation/histotripsy thresholds at various locations in a user-selected region of interest or defined treatment area/volume, to determine the minimum cavitation thresholds throughout said region or area/volume, to ensure treatment parameters are optimized to achieve, maintain and dynamically control acoustic cavitation/histotripsy. During treatment planning or during therapy, cavitation threshold test pulses can be transmitted into a plurality of locations of interest. The number of test locations of interest can be chosen based on the size and/or shape of the treatment region. For example, a spherical treatment region benefits from at least seven test locations to probe the extremes of the spherical volume. In one example, the test protocol and test pulses can be positioned at 1) the center of the treatment volume, 2) the proximal-most aspect of the treatment volume (top), 3) the distal-most aspect of the treatment volume, 4) the left-most aspect of the treatment volume, 5) the right-most aspect of the treatment volume, 6) the cranial-most aspect of the treatment volume (head), and 7) the caudal-most aspect of the treatment volume (tail).

During therapy, the cavitation threshold at each of the locations of interest can be evaluated with a single therapy PRF to determine if cavitation has formed before incrementing to the next PRF. For example, the formation (or not) of cavitation can be observed in real-time with imaging such as ultrasound imaging. In general, the driving voltage required to initiate a vigorous bubble cloud in tissue decreases as the therapy PRF increases. The cavitation threshold in the tissue can also vary as a treatment procedure progresses. Thus, testing various points of interest within a treatment volume during treatment can be a useful tool to evaluate the cavitation threshold(s) in real-time and adjust the PRF and/or driving voltage of the therapy pulses to optimize treatment at each of the tested locations. The treatment protocol itself can then be adjusted based on the test pulses to utilize variable amplitudes/PRF based on the test results to ensure the optimal amount of energy is delivered into each location of the tissue for histotripsy therapy. Additionally, the depth at each of the test locations can be measured or determined (either manually or automatically with the system) to provide additional information to the system for determining optimal treatment parameters.

In some embodiments, the test locations can be used to determine a maximum amount of energy that may be applied without generating undesired damage to the test location or surround or intervening tissues. For example, while determining the cavitation thresholds at each of the test locations, the drive voltage and/or PRF of the system can be increased until cavitation is observed under real-time imaging. In some embodiments, the drive voltage and/or PRF can be increased until undesirable damage to the test location or cavitation/thermal damage to other locations outside of the test location are observed. This can be used to determine the maximum amount of energy that can be applied for a given test location.

Based on the test protocol and tested cavitation thresholds, the appropriate driving voltage for each point in the treatment grid can be chosen. With the required voltage at the center and six extremes of the target volume serving as inputs, the voltages for the remaining points comprising the treatment volume can be interpolated. The driving voltage can then be adjusted automatically by the software as the therapy progresses through the automated treatment volume. In this way each point is ablated using an amplitude sufficient to maintain an efficacious bubble cloud, but not overly so in order to minimize the thermal deposition in the acoustic path.

For example, a method of delivering histotripsy therapy to tissue can comprise delivering histotripsy pulses into tissue at a plurality of target test locations and imaging the test location in real-time to evaluate whether cavitation has formed at the test locations. If cavitation has not formed at the test locations, the driving voltage and/or the PRF of the histotripsy pulses can be adjusted, and histotripsy pulses with the adjusted parameters can be delivered into the tissue at the test locations. Real-time imaging can again be used to evaluate whether cavitation has formed at each test location. This process can be repeated until the cavitation threshold at each test location is determined, and a high-density map can be created based on various algorithms to extrapolate thresholds across the targeted region of interest/treatment volume, specific to the acoustic pathway and target depth. For example, if cavitation thresholds are known at a first test location and a second test location, then the cavitation threshold at a third test location can be extrapolated based on the cavitation thresholds of the first and second test locations. This extrapolation can be further based on the tissue type, target tissue depth, and acoustic pathway of the third test location.

In one example, a method of treating tissue can comprise transmitting ultrasound pulses into a first test location with at least one ultrasound transducer, determining a first cavitation threshold at the first test location, transmitting ultrasound pulses into a second test location with the at least one ultrasound transducer, determining a second cavitation threshold at the second test location, adjusting a first driving voltage and/or PRF of the at least one transducer based on the first cavitation threshold, transmitting ultrasound pulses into the first test location with the at least one ultrasound transducer at the first adjusted driving voltage and/or PRF to generate cavitation at the first test location, adjusting a second driving voltage and/or PRF of the at least one transducer based on the second cavitation threshold, and transmitting ultrasound pulses into the second test location with the at least one ultrasound transducer at the second adjusted driving voltage and/or PRF to generate cavitation at the second test location.

Other Components, Ancillaries and Accessories

The system may comprise various other components, ancillaries and accessories, including but not limited to computers, computer processors, power supplies including high voltage power supplies, controllers, cables, connectors, networking devices, software applications for security, communication, integration into information systems including hospital information systems, cellular communication devices and modems, handheld wired or wireless controllers, goggles or glasses for advanced visualization, augmented or virtual reality applications, cameras, sensors, tablets, smart devices, phones, internet of things enabling capabilities, specialized use "apps" or user training materials and applications (software or paper based), virtual proctors or trainers and/or other enabling features, devices, systems or applications, and/or methods of using the above.

System Variations and Methods/Applications

In addition to performing a breadth of procedures, the system may allow additional benefits, such as enhanced planning, imaging and guidance to assist the user. In one embodiment, the system may allow a user to create a patient, target and application specific treatment plan, wherein the system may be configured to optimize treatment parameters based on feedback to the system during planning, and where planning may further comprise the ability to run various test protocols to gather specific inputs to the system and plan.

Feedback may include various energy, power, location, position, tissue and/or other parameters.

The system, and the above feedback, may also be further configured and used to autonomously (and robotically) execute the delivery of the optimized treatment plan and protocol, as visualized under real-time imaging during the procedure, allowing the user to directly observe the local treatment tissue effect, as it progresses through treatment, and start/stop/modify treatment at their discretion. Both test and treatment protocols may be updated over the course of the procedure at the direction of the user, or in some embodiments, based on logic embedded within the system.

It is also recognized that many of these benefits may further improve other forms of acoustic therapy, including thermal ablation with high intensity focused ultrasound (HIFU), high intensity therapeutic ultrasound (HITU) including boiling histotripsy (thermal cavitation), and are considered as part of this disclosure.

In another aspect, the Therapy sub-system, comprising in part, one or more amplifiers, transducers and power supplies, may be configured to allow multiple acoustic cavitation and histotripsy driving capabilities, affording specific benefits based on application, method and/or patient specific use. These benefits may include, but are not limited to, the ability to better optimize and control treatment parameters, which may allow delivery of more energy, with more desirable thermal profiles, increased treatment speed and reduced procedure times, enable electronic beam steering and/or other features.

This disclosure also includes novel systems and concepts as related to systems and sub-systems comprising new and "universal" amplifiers, which may allow multiple driving approaches (e.g., single and multi-cycle pulsing). In some embodiments, this may include various novel features to further protect the system and user, in terms of electrical safety or other hazards (e.g., damage to transducer and/or amplifier circuitry).

In another aspect, the system, and Therapy sub-system, may include a plethora of therapy transducers, where said therapy transducers are configured for specific applications and uses and may accommodate treating over a wide range of working parameters (target size, depth, location, etc.) and may comprise a wide range of working specifications (detailed below). Transducers may further adapt, interface and connect to a robotically-enabled system, as well as the Coupling sub-system, allowing the transducer to be positioned within, or along with, an acoustic coupling device allowing, in many embodiments, concurrent imaging and histotripsy treatments through an acceptable acoustic window. The therapy transducer may also comprise an integrated imaging probe or localization sensors, capable of displaying and determining transducer position within the treatment site and affording a direct field of view (or representation of) the treatment site, and as the acoustic cavitation/histotripsy tissue effect and bubble cloud may or may not change in appearance and intensity, throughout the treatment, and as a function of its location within said treatment (e.g., tumor, healthy tissue surrounding, critical structures, adipose tissue, etc.).

The systems, methods and use of the system disclosed herein, may be beneficial to overcoming significant unmet needs in the areas of soft tissue ablation, oncology, advanced image guided procedures, surgical procedures including but not limited to open, laparoscopic, single incision, natural orifice, endoscopic, non-invasive, various combination of, various interventional spaces for catheter-based procedures of the vascular, cardiovascular and/or neuro-related spaces, cosmetics/aesthetics, metabolic (e.g., type 2 diabetes), plastics and reconstructive, ocular and ophthalmology, gynecology and men's health, and other systems, devices and methods of treating diseased, injured, undesired, or healthy tissues, organs or cells.

Systems and methods are also provided for improving treatment patterns within tissue that can reduce treatment time, improve efficacy, and reduce the amount of energy and prefocal tissue heating delivered to patients.

Use Environments

The disclosed system, methods of use, and use of the system, may be conducted in a plethora of environments and settings, with or without various support systems such as anesthesia, including but not limited to, procedure suites, operating rooms, hybrid rooms, in and out-patient settings, ambulatory settings, imaging centers, radiology, radiation therapy, oncology, surgical and/or any medical center, as well as physician offices, mobile healthcare centers or systems, automobiles and related vehicles (e.g., van), and/or any structure capable of providing temporary procedure support (e.g., tent). In some cases, systems and/or subsystems disclosed herein may also be provided as integrated features into other environments, for example, the direct integration of the histotripsy Therapy sub-system into a MRI scanner or patient surface/bed, wherein at a minimum the therapy generator and transducer are integral to such, and in other cases wherein the histotripsy configuration further includes a robotic positioning system, which also may be integral to a scanner or bed centered design. In some embodiments, the system and/or various sub-systems may be configured to be used in a laboratory and bench setting, wherein some cases histotripsy is performed to produce tissue homogenates or lysates for further use directly as therapies, immunotherapies or biologically targeted therapies, or in the further preparation of such. This may specifically include the use of histotripsy lysates to prime cell therapies (dendritic or T cell) as an unlimited example. Further, such homogenates or lysates may be stored and banked for immediate or later use.

Cancer Immunotherapy

As described above, Histotripsy is a non-invasive ablation method that delivers focused, microsecond-length, high-pressure, ultrasound pulses that create cavitation microbubbles in the target tissues, with no need for supplementary external agents. The rapid expansion and collapse of cavitation microbubbles produces high strain that mechanically disrupts cell membranes and structures in the target tissue, resulting in a liquefied and soluble tissue homogenate. Thus, the histotripsy therapy is configured to liquefy, lyse, and/or solubilize the target tissue. Unlike HIFU thermal ablation, histotripsy destroys tumors by causing cell and nuclear membrane disruption, without heating or denaturing potentially antigenic tumor peptides. Although boiling histotripsy also produces liquefied acellular debris, the process is different as it creates rapid heating to boiling temperatures to produce large vapor bubbles that disrupt cells. Therefore, protein is also presumably denatured during the boiling process, and due to the partial thermal coagulation of the tissue, the resulting treatment debris may not be as readily soluble as traditional histotripsy. The mechanically disrupted and soluble acellular debris generated by histotripsy is systemically reabsorbed. In this way, histotripsy can destroy tumors while preserving and showcasing their previously hidden subcellular contents via the liquefication and solubilization of such, including tumor antigens and biomarkers, to the immune system.

Furthermore, histotripsy effectively induces cancer cell immunogenic cell death (ICD). The manner in which a cancer cell dies can have vastly different implications on immune detection. Apoptotic non-immunogenic cell death (NICD) results in macrophage-mediated clearance of cancer cell debris amidst a non-inflammatory cytokine milieu that ultimately suppresses adaptive immune responses to cancer. In contrast, ICD is a process in which necrotic cancer cells release subcellular contents called damage associated molecular patterns (DAMPs). When released outside the protective confines of the cancer cell membrane, DAMPs trigger a cascade of inflammatory events culminating in the activation of T cells and natural killer cells. It is postulated that induction of cancer cell ICD could promote immunological detection of cancers. Unfortunately, the ability of traditional oncological therapies, like radiation therapy, chemotherapy, radiofrequency ablation, and microwave ablation, to cause ICD is modest. In addition, these interventions cause off-target effects that undercut ICD. For example, chemotherapy and radiation have systemic cytotoxicities that skew the immune system toward global immune suppression. Radiation and thermal ablation causes extensive denaturation of subcellular contents that can limit the potency of DAMP-mediated ICD, as well as more limited bioavailability of DAMPs. However, the novel approaches described herein, utilizing histotripsy therapy, can trigger and allow DAMP release and inflammation events through ICD. Moreover, the completely non-invasive and precisely targeted nature of its delivery minimizes the risk of negative or adverse off-target effects.

Histotripsy "immunosensitization" techniques described herein are configured to release, and in some cases liquefy, lyse, and/or solubilize, tumor antigens and produce ICD, which is expected to potentiate the immunogenicity of treated tumors and make cancers more responsive to conventional immunotherapy. Thus, histotripsy "immunosensitization" as described herein can be used to sensitize previously resistant cancers to immunotherapy further allowing immune recognition. Histotripsy immunosensitization is not merely a modality of local tumor ablation, but a trigger to allow patients whose disseminated, refractory cancers outside of the ablation zone can be made responsive to immune therapy, regionally and systemically. This can be done by histotripsy ablation itself or a combination of histotripsy ablation with various bioactive agents and therapeutics (e.g., RNA/DNA, gene, protein, antibody, cell and/or other therapies) including, but not limited to, as an example, checkpoint inhibitor (CI) immunotherapies to maximize therapeutic effect.

Histotripsy immunosensitization as described herein is qualitatively distinct from conventional histotripsy treatment, including histotripsy tumor ablation. The purpose of histotripsy immunosensitization is to stimulate immune responses to treated tumors that are of sufficient magnitude to produce regional and/or systemic (abscopal) effects (growth inhibition of tumors outside the ablation zone) at distant tumor sites. In some examples, this may be modulated through the dose and distribution of histotripsy through the selected volume/location of treated tumor(s). In some cases, complete tumor ablation is not the ultimate goal or required for/of histotripsy immunosensitization; rather, the overall goal is to stimulate a systemic tumor-specific immune response. In some uses, to achieve this immune stimulation, histotripsy immunosensitization can be implemented with the innovative approaches described herein. Histotripsy can also be combined with various therapeutics, including checkpoint inhibition therapy and other adjuvant therapies to enhance/maximize the abscopal effect, as described herein. Moreover, histotripsy immunosensitization can be used to produce histotripsy cancer vaccines or lysate based therapeutics as described herein. In some examples, histotripsy lysates may be re-administered to patients as autologous therapies wherein the solubilized lysate is used directly as therapy (systemic or locally delivered), or is used to stimulate and/or produce enhanced therapies (e.g., activated or primed cell therapies), and/or may be further combined with other therapies.

Figure 2:
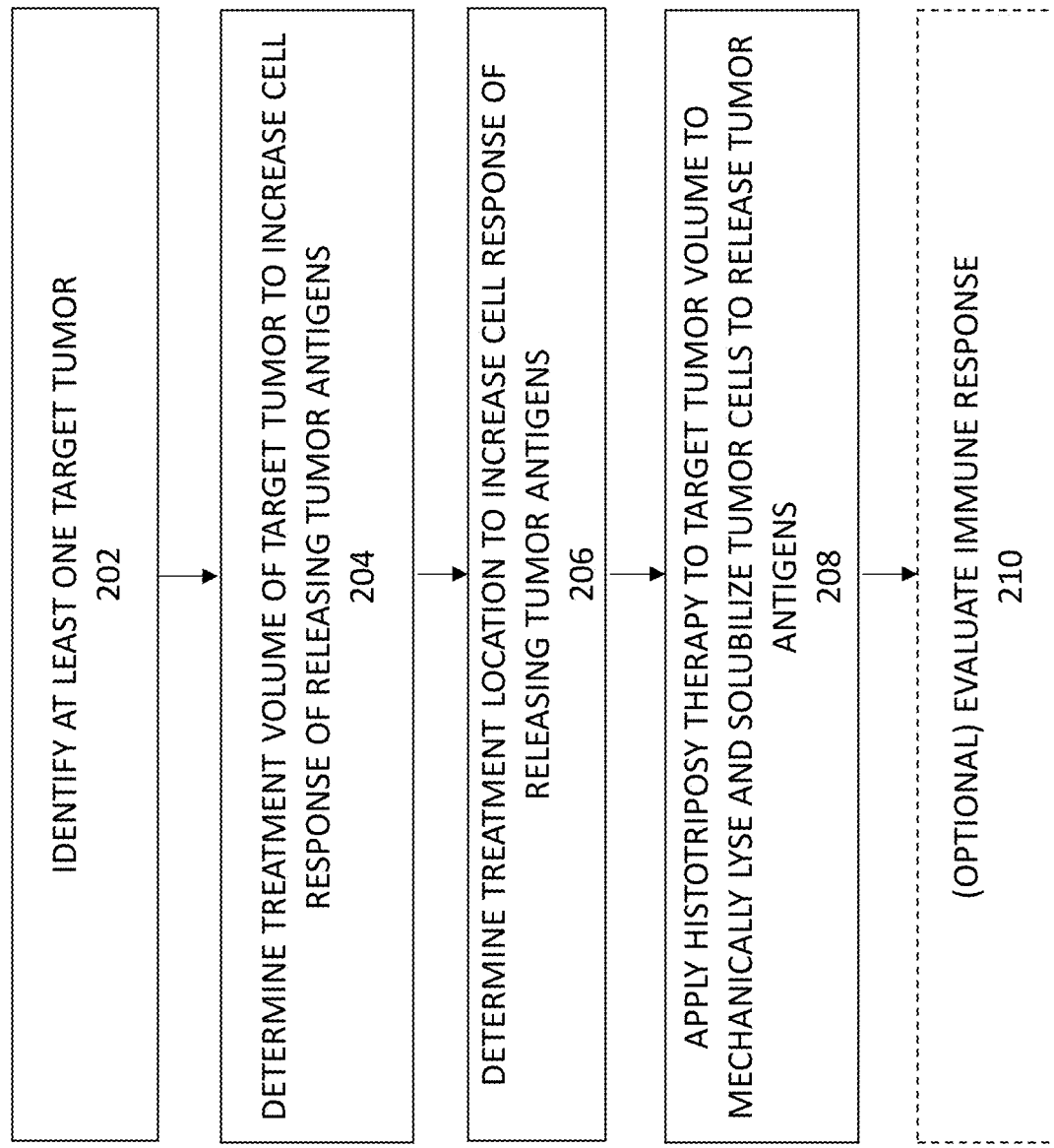
FIG. 2 illustrates a flowchart that describes one method for treating tissue with histotripsy therapy.

FIG. 2 depicts a flowchart 200 that describes example steps for performing histotripsy immunosensitization using the system components described above, including a histotripsy therapy transducer, a robotic positioning system, and/or a surgical navigation system. In some embodiments, the method can be used for treating tissue previously treated with radiation therapy and/or resistant to radiation therapy. In another embodiment, the method can be used for treating tissue previously treated with immunotherapy and non-responsive or resistant to immunotherapy.

At step 202 of flowchart 200, at least one target tumor can be identified with the therapy system. Step 202 can include identifying the precise location of the target tumor location within the body of the patient, including identifying details about the size, shape, volume, mass, and tissue type(s) of the target tumor location. For example, the identifying step can include identifying the type of tumor, the type of tissue or organ within which the tumor is located, and the volume or mass of the tumor itself. In some implementations, identifying the at least one target tumor can be achieved with a medical imaging modality such as ultrasound, MRI, CT, or the like.

The target tumor can comprise tumors or other abnormal tissue volumes within a liver, a kidney, a spleen, a pancreas, a colorectal, a bowel, a stomach, an esophagus, a breast, a lung, a head, a neck, a thyroid, skin, nervous tissue, hematological malignancies, a sarcoma, primary and metastatic lesions, and brain tissue.

At step 204 of flowchart 200, the method can include determining a treatment volume of the target tumor to ablate so as to increase, enhance, and/or maximize the cell response of releasing tumor antigens. For example, if the chosen treatment volume is too small, the stimulated immune response will be insufficient. Conversely, if the ablation volume is too large, treatment-related clinical complications could ensue and/or the immune response may be sub-optimal. Determining treatment volume can be critical for the purpose of immune stimulation, such that sufficient immune stimulation is achieved without significant complications. In some examples, ablation of sufficient number of cells typically comprises ablation of >1 mL tissue or >10% of the target tumor. In another embodiment, the treatment volume of the at least one target tumor ranges from 25% to 90% of a volume of the at least one target tumor. In another implementation, the treatment volume of the at least one target tumor is at least 1 cm$^3$ in volume. The extent of immune stimulation by histotripsy may be impacted by ablation volume (20% vs. 80% vs. 100%; 1 mL vs. 20 mL vs. 60 mL) and can also be impacted by the type of cancer or the location of the target tumor region. For example, the location of the target tissue volume or the target tumor type can be used to determine the optimal treatment volume.

Alternatively, at step 204 of flowchart 200, the method can include determining a treatment volume of the target tumor to ablate that will increase, enhance, and/or maximize induction of immunogenic cell death.

At step 206 of flowchart 200, the method can further include determining a treatment location to increase, enhance, and/or maximize the cell response of releasing tumor antigens. For example, in some embodiments, the treatment location comprises only a central/inner portion of the at least one target tumor. In other embodiments, the treatment location comprises only a periphery/outer portion of the at least one target tumor. In another implementation, the treatment location comprises a plurality of programmed treatment locations distributed spatially through the at least one target tumor. It is possible that the extent of immune stimulation by histotripsy may be impacted by the pattern of ablation (e.g., ablation of the inner core/central portion vs. outer rim/periphery only; contiguous ablation vs. checkerboard pattern). For example, a checkerboard ablation pattern may allow more vascular access to the ablated acellular debris, which may increase the magnitude of the stimulated immune response as compared to a contiguous pattern of ablation. The treatment location chosen at step 206 can depend on the type of tissue to be treated, including the tumor type/cancer type, the surrounding tissues, the size and or shape of the target tumor, etc.

Alternatively, at step 206 of flowchart 200, the method can include determining a treatment location of the target tumor to ablate that will maximize induction of immunogenic cell death.

In some embodiments, the cell response includes immunogenic cell death, infiltration of inflammatory and antigen presenting cells, infiltration and activation of T cells, increased tumor-specific T cells, infiltration of natural killer cells, B cells and CD4+ T cells, and/or depletion of immunosuppressive regulatory T cells and myeloid-derived suppressor cells.

Figure 3:
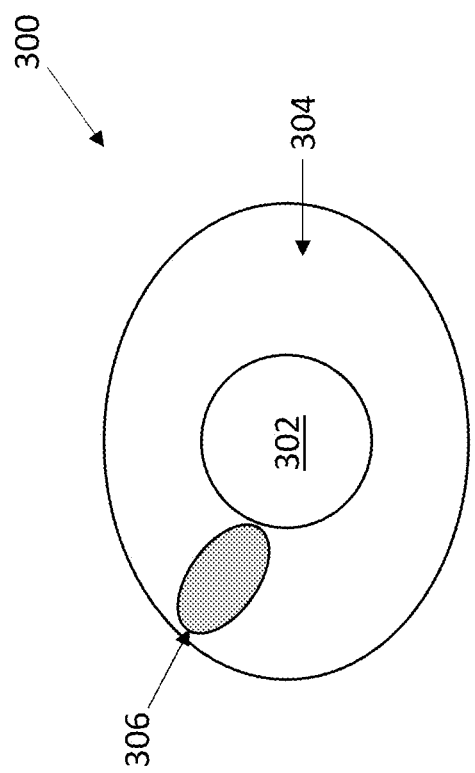
FIG. 3 is an example of a target tissue volume having a central/inner portion and a peripheral/outer portion.

FIG. 3 is an example of a target tumor or target tissue volume 300, including a central/inner portion 302 and a periphery or peripheral/outer portion 304. The periphery or peripheral portion 304 of the target tumor can be thought of as a portion or section of the tumor that adjacent to the outer edges of the target volume. The central/inner portion 302 can be referred to as a volume within the target tumor that is entirely surrounded by the periphery, as shown in FIG. 3. In some examples, the entirety of the peripheral portion can comprise the treatment location from step 206 of flowchart 200. In other examples, only a portion of the peripheral portion can be treated, such as, for example, a volume 306 (having the desired treatment volume from step 204 of flowchart 200) within the peripheral portion.

At step 208 of flowchart 200, the histotripsy therapy transducer can apply histotripsy therapy to a target tumor volume with the selected treatment volume and treatment location to mechanically lyse, solubilize, and/or liquefy the tumor cell membranes of a sufficient number of tumor cells to release tumor antigens in the target tumor volume. In some embodiments, the application of histotripsy therapy induces immunogenic cell death. The histotripsy therapy is applied so as to disrupt the tumor cell membranes without generating adequate heating in the target tissue volume to cause protein denaturation. To achieve this goal, the histotripsy immunosensitization therapy described in step 208 may be carried out in one or more sessions, over which an optimal volume is ablated during each session.

As described above, histotripsy therapy creates cavitation in a target tissue volume with by applying histotripsy pulses to the histotripsy therapy transducer that have microsecond pulse lengths (<20 us), high peak negative pressure (>10 MPa), and a low duty cycle (<5%), to mechanically lyse, solubilize, and/or liquefy the target tumor volume and to disrupt the tumor cell membrane, while avoiding tissue heating.

In another example, our preliminary data shows that histotripsy monotherapy of one tumor site results in significant reduction in the number and volume of distant untreated tumor site, including metastases (abscopal effect). This includes therapeutic response locally, regionally (draining lymphatic) and systemically (circulation). Thus, the method provided herein can be used not only to treat the ablated tumor volume, but also tumor/cancer volumes that are separate from or apart from the targeted tumor volume. As a further example, one of a plethora of colorectal metastases may be treated in the liver, with an observed therapeutic response seen in the stabilization or reduction in tumor burden of other non-treated tumors (and of non-liver origin).

To control the ablation of specific volume, shape, and patter, histotripsy delivery can be assisted by the robotic arm and/or navigation system described above, which can be used to mechanically move the histotripsy transducer, such that the histotripsy focus will be scanned to cover the planned tumor volume, with specific volume, shape, and pattern. Furthermore, the system can be configured to control the ablation of specific volume, shape, and pattern, histotripsy delivery by electronic focal steering using a 2D phased array ultrasound transducer, which can be used to electronically move the histotripsy transducer, such that the histotripsy focus will be scanned to cover the planned tumor volume, with specific volume, shape, and pattern.

As described above, histotripsy targeting and delivery to the target tumor can be guided by real-time imaging, e.g., ultrasound imaging, CT, or MRI. The imaging feedback can confirm that histotripsy is used to treat the planned tumor volume of a specific volume, shape, and pattern.

In some embodiments, applying the histotripsy treatment causes the release of damage associated molecular patterns (DAMPs). The DAMPs can be, for example, High Mobility Group Box 1 (HMGB1), calreticulin (CRT), adenosine triphosphate (ATP), heat shock proteins (HSP), fibronectin (FN), deoxyribonucleic acid (DNA), ribonucleic acid (RNA) and combinations thereof. In one embodiment, the DNA comprises cell-free DNA. In another embodiment, the RNA comprises mRNA.

Optionally, at step 210 of flowchart 200, the method can further include evaluating the immune response and therapeutic effect after delivery of histotripsy therapy to the target tumor location. Evaluating the immune response can allow time for the lysed, solubilized, and or liquefied acellular debris produced by histotripsy to stimulate adaptive immune responses in tumor draining lymph nodes and within the systemic circulation, and can allow time to cause inflammation and DAMP release. These changes are expected to lead to regional and systemic tumor-specific immune responses. The evaluation step can include assessment of immunological cell death and/or immune activation.

The evaluating step can comprise imaging the cell response, the imaging comprising ultrasound, CT, MRI, and/or PET imaging. In some embodiments, evaluating the immune response comprises imaging the at least one target tumor and/or performing a tissue biopsy on the at least one target tumor. The stimulated immune response can be evaluated with blood tests, and abscopal effects on distant tumor sites can be evaluated with non-invasive imaging following histotripsy immunosensitization. In some examples, evaluating the immune response comprises evaluating the immune response in one or more organs or anatomical locations. In other embodiments, evaluating the immune response includes biomarker analyses of tissue, cells, blood and/or combinations thereof. In some examples, the evaluation can takes 1-10 days to stimulate sufficient immune response. In other embodiments, the evaluation can occur weeks to months after delivering histotripsy therapy.

The nature and magnitude of immune stimulation may vary between patients and tumor types. Blood drawn from patients may be used for testing of specific immune biomarkers (e.g., quantity and activation status of T cell subsets, dendritic cells, neutrophils, natural killer cells, macrophages, regulatory T cells, myeloid-derived suppressor cells, etc.) to evaluate the extent of immunostimulation induced by histotripsy. In addition, abscopal immune responses can be measured using immunohistochemical analyses of relevant immune cell infiltration can be performed on biopsies obtained from distant tumor sites after histotripsy treatment. Abscopal effects on distant tumors can be monitored using non-invasive imaging following histotripsy immunosensitization, such as magnetic resonant imaging (MRI), computed tomography (CT), or ultrasonography (US).

The techniques described herein can be combined with other immunomodulatory treatments to increase, enhance, and/or maximize abscopal effects. Immunotherapy drugs (e.g., checkpoint inhibition monoclonal antibodies against PD-1 and CTLA-4) can be applied in conjunction with histotripsy immunosensitization described above. The timing with which checkpoint inhibitors are delivered can ideally be concurrent with the timing of maximal immune response stimulated by histotripsy. Thus, the evaluation at step 710 of flowchart 700 can be used to determine when immunomodulatory treatments can or will be applied to the patient.

Additionally, adjuvant may be combined with histotripsy and immunotherapy to enhance the therapeutic effect. Various types of adjuvant (e.g., CpG, Ibrutinib, etc.) have been combined with immunotherapy, radiation therapy, or other ablation therapy to enhance the therapeutic effect. One or more adjuvant administrations can be applied before or after histotripsy, in addition to or potentially instead of immunotherapy drug administration.

The nature and magnitude of immune stimulation may vary between patients and tumor types. Blood drawn from patients may be used for testing of specific immune biomarkers (e.g., quantity and activation status of T cell subsets, dendritic cells, neutrophils, natural killer cells, macrophages, regulatory T cells, myeloid-derived suppressor cells, etc.) to determine the timing of maximal immune response and optimal timing of immunotherapy drug administration. In addition, abscopal immune responses can be measured using immunohistochemical analyses of relevant immune cell infiltration can be performed on biopsies obtained from distant tumor sites after histotripsy treatment.

Figure 4:
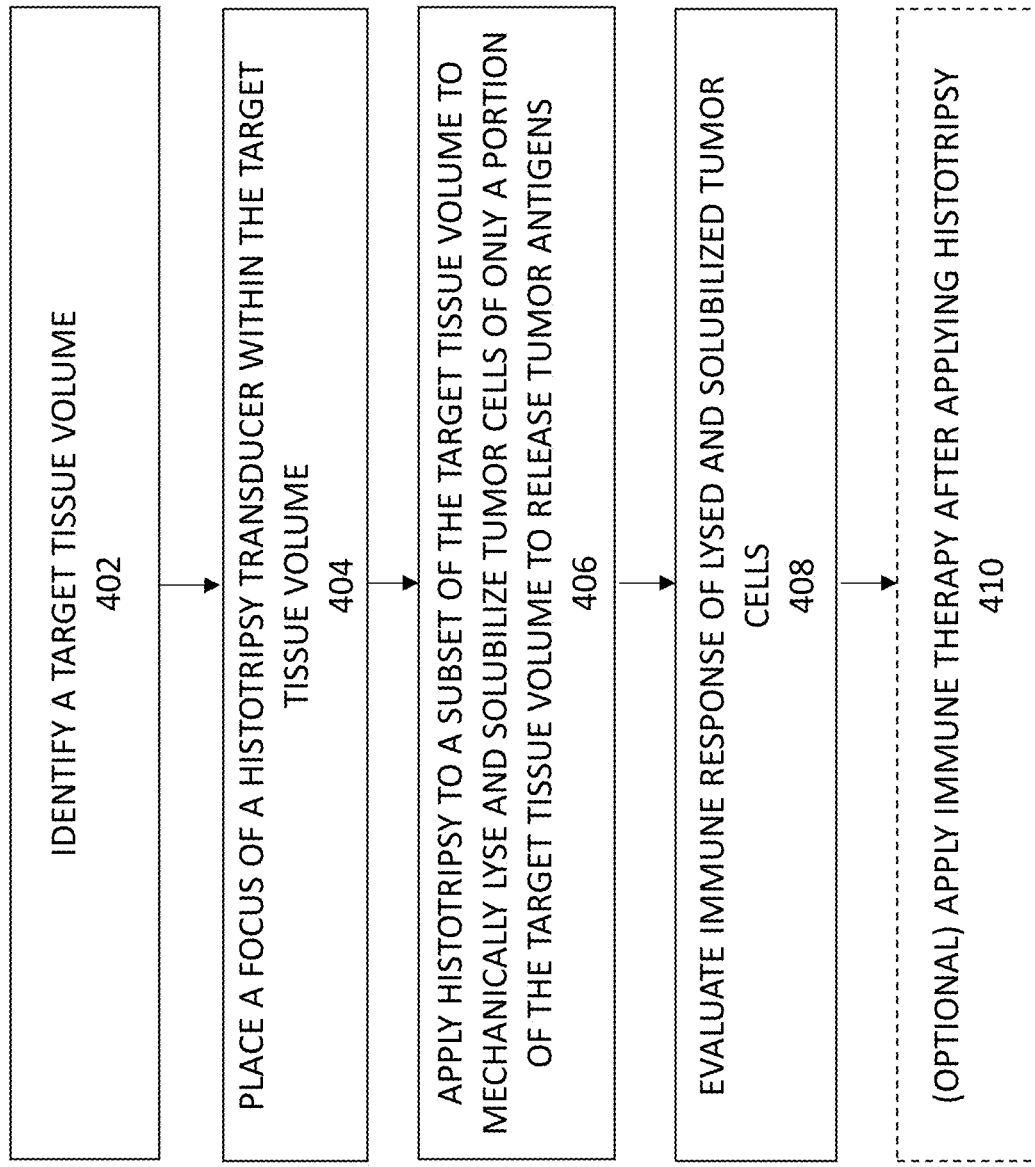
FIG. 4 illustrates another flowchart that describes one method for treating tissue with histotripsy therapy.

FIG. 4 depicts a flowchart 400 that describes example steps for performing histotripsy immunosensitization using the system components described above, including a histotripsy therapy transducer, a robotic positioning system, and/or a surgical navigation system.

At step 402 of flowchart 400, at least one target tissue volume can be identified with the therapy system. Step 402 can include identifying the precise location of the target tissue volume within the body of the patient, including identifying details about the size, shape, volume, mass, and tissue type(s) of the target tissue volume. For example, the identifying step can include identifying the type of volume (e.g., tumor), the type of tissue or organ within which the volume is located, and the volume or mass of the target volume itself. In some implementations, identifying the at least one target tissue volume can be achieved with a medical imaging modality such as ultrasound, MRI, CT, or the like.

The target tissue volume can comprise tumors or other abnormal tissue volumes within a liver, a kidney, a spleen, a pancreas, a colorectal, a bowel, a stomach, an esophagus, a breast, a lung, a head, a neck, a thyroid, skin, nervous tissue, hematological malignancies, a sarcoma, primary and metastatic lesions, and brain tissue.

In some examples, identifying the target tissue volume can further include determining a treatment volume of the target tumor to ablate so as to maximize the cell response of releasing tumor antigens. For example, if the chosen treatment volume is too small, the stimulated immune response will be insufficient. Conversely, if the ablation volume is too large, treatment-related clinical complications could ensue and/or the immune response may be sub-optimal. Determining treatment volume can be critical for the purpose of immune stimulation, such that sufficient immune stimulation is achieved without significant complications. In some examples, ablation of sufficient number of cells typically comprises ablation of >1 mL tissue or >10% of the target tumor. In another embodiment, the treatment volume of the at least one target tumor ranges from 25% to 90% of a volume of the at least one target tumor. In another implementation, the treatment volume of the at least one target tumor is at least 1 cm$^3$ in volume. The extent of immune stimulation by histotripsy may be impacted by ablation volume (20% vs. 80% vs. 100%; 1 mL vs. 20 mL vs. 60 mL) and can also be impacted by the type of cancer or the location of the target tumor region. For example, the location of the target tissue volume or the target tumor type can be used to determine the optimal treatment volume.

In other embodiments, identifying the target tissue volume can further include determining a treatment location to increase, enhance, and/or maximize the cell response of releasing tumor antigens. For example, in some embodiments, the treatment location comprises only a central/inner portion of the at least one target tumor. In other embodiments, the treatment location comprises only a periphery/outer portion of the at least one target tumor. In another implementation, the treatment location comprises a plurality of programmed treatment locations distributed spatially through the at least one target tumor. It is possible that the extent of immune stimulation by histotripsy may be impacted by the pattern of ablation (e.g., ablation of the inner core/central portion vs. outer rim/periphery only; contiguous ablation vs. checkerboard pattern). For example, a checkerboard ablation pattern may allow more vascular access to the ablated acellular debris, which may increase the magnitude of the stimulated immune response as compared to a contiguous pattern of ablation. The treatment location chosen at step 206 can depend on the type of tissue to be treated, including the tumor type/cancer type, the surrounding tissues, the size and or shape of the target tumor, etc.

In some embodiments, identifying the target tissue volume further comprises identifying a first target tissue volume and a second target tissue volume. In some embodiments, the first and second target tissue volumes are located in the same organ or anatomical location. In other embodiments, the first and second target tissue volumes are located in different organs or anatomical locations.

At step 404 of flowchart 400, the method can include placing a focus of a histotripsy therapy transducer within the target tissue volume. In some examples, placing the focus can comprise placing the focus with a robotic positioning system. For example, a histotripsy therapy transducer can be positioned on a robotic arm of the robotic positioning system, and the robotic positioning system can use real-time feedback to place the focus within the target tissue volume, or alternatively, the robotic positioning system can use knowledge of the focal distance of the transducer to accurately place the focus at the desired position within tissue. in some embodiments, the robotic positioning system comprises a robotic arm with a minimum of 3 degrees of freedom. In other embodiments, the robotic positioning system comprises a robotic arm that directs a histotripsy therapy transducer through a pre-programmed three-dimensional treatment routine.

In some embodiments, the method can further include applying histotripsy test pulses to the at least one target tumor to determine a cavitation threshold at one or more test locations within the at least one target tumor. Using these test pulses, the method can further include deriving a histotripsy treatment plan based on the determined cavitation threshold at the one or more test locations.

At step 406 of flowchart 400, the histotripsy therapy transducer can apply histotripsy therapy to a subset of the target tissue volume to mechanically lyse, solubilize, and/or liquefy tumor cells of only a portion of the target tissue volume to release tumor antigens. The histotripsy therapy is applied so as to disrupt the tumor cell membranes without generating adequate heating in the target tissue volume to cause protein denaturation. To achieve this goal, the histotripsy immunosensitization therapy described in step 406 may be carried out in one or more sessions, over which an optimal volume is ablated during each session. In embodiment in which test pulses are used to derive a histotripsy treatment plan based on cavitation threshold(s), applying the histotripsy therapy can be based on the histotripsy treatment plan.

As described above, histotripsy therapy creates cavitation in a target tissue volume with by applying histotripsy pulses to the histotripsy therapy transducer that have microsecond pulse lengths (<20 us), high peak negative pressure (>10 MPa), and a low duty cycle (<5%), to mechanically lyse, solubilize, and/or liquefy the target tumor volume and to disrupt the tumor cell membrane, while avoiding tissue heating.

In another example, our preliminary data shows that histotripsy monotherapy of one tumor site results in significant reduction in the number and volume of distant untreated tumor site, including metastases (abscopal effect). This includes therapeutic response locally, regionally (draining lymphatic) and systemically (circulation). Thus, the method provided herein can be used not only to treat the ablated tumor volume, but also tumor/cancer volumes that are separate from or apart from the targeted tumor volume. As a further example, one of a plethora of colorectal metastases may be treated in the liver, with an observed therapeutic response seen in the stabilization or reduction in tumor burden of other non-treated tumors (and of non-liver origin).

To control the ablation of specific volume, shape, and patter, histotripsy delivery can be assisted by the robotic arm and/or navigation system described above, which can be used to mechanically move the histotripsy transducer, such that the histotripsy focus will be scanned to cover the planned tumor volume, with specific volume, shape, and pattern. Furthermore, the system can be configured to control the ablation of specific volume, shape, and pattern, histotripsy delivery by electronic focal steering using a 2D phased array ultrasound transducer, which can be used to electronically move the histotripsy transducer, such that the histotripsy focus will be scanned to cover the planned tumor volume, with specific volume, shape, and pattern.

In some embodiments, the histotripsy can be applied to only a subset of the target tissue volume. For example, the histotripsy can be applied only to a subset of the target tissue volume that comprises approximately 25% to 90% of the target tissue volume. Alternatively, the subset can comprise at least 1 cm$^3$ in volume. In some embodiments, the subset comprises only a central/inner portion of the target tissue volume. Alternatively, the subset can include only a periphery or peripheral/outer portion of the target tissue volume. In one implementation, the applying histotripsy to the subset of the target tissue volume further comprises applying histotripsy to a plurality of programmed treatment locations distributed spatially through the target tissue volume.

As described above, histotripsy targeting and delivery to the target tumor can be guided by real-time imaging, e.g., ultrasound imaging, CT, or MRI. The imaging feedback can confirm that histotripsy is used to treat the planned tumor volume of a specific volume, shape, and pattern.

At step 408 of flowchart 400, the method can further include evaluating the immune response and therapeutic effect after delivery of histotripsy therapy to the target tumor location. Evaluating the immune response can allow time for the lysed, solubilized, and or liquefied acellular debris produced by histotripsy to stimulate adaptive immune responses in tumor draining lymph nodes and within the systemic circulation, and can allow time to cause inflammation and DAMP release. These changes are expected to lead to regional and systemic tumor-specific immune responses. The evaluation step can include assessment of immunological cell death and/or immune activation.

The evaluating step can comprise imaging the cell response, the imaging comprising ultrasound, CT, MRI, and/or PET imaging. In some embodiments, evaluating the immune response comprises imaging the at least one target tumor and/or performing a tissue biopsy on the at least one target tumor. The stimulated immune response can be evaluated with blood tests, and abscopal effects on distant tumor sites can be evaluated with non-invasive imaging following histotripsy immunosensitization. In some examples, evaluating the immune response comprises evaluating the immune response in one or more organs or anatomical locations. In other embodiments, evaluating the immune response includes biomarker analyses of tissue, cells, blood and/or combinations thereof. In some examples, the evaluation can takes 1-10 days to stimulate sufficient immune response. In other embodiments, the evaluation can occur weeks to months after delivering histotripsy therapy.

Optionally, at step 410 of flowchart 400, the method can further include applying immune therapy after applying histotripsy. In some embodiments, the immune therapy can be checkpoint inhibitors, immunostimulatory therapies, cancer vaccines, oncolytic viruses, neutralizing immune inhibitors, activating cytokines, and/or any combinations thereof. In some examples, the checkpoint inhibitors include CTLA-4, LAG3, TIM3, and combinations thereof. In other embodiments, the checkpoint inhibitors include PD-1 blockade, PD-L1 blockade, and combinations thereof.

The application of immune therapy can occur after the histotripsy therapy. In some embodiments, the immune therapy is applied weeks or even months after the histotripsy. For example, in one embodiment the immune therapy can be applied between 1 to 6 weeks after applying histotripsy. In other embodiments, the immune therapy can be applied between 2 to 4 weeks after applying histotripsy.

Applying the immune therapy can include oral administration, systemic infusion, loco-regional catheter-based infusion, intratumoral injection, loco-regional injection, subcutaneous injection, and/or combinations thereof. In some implementations, the robotic positioning system is used for the loco-regional catheter infusion, loco-regional injection, intratumoral injection, and/or combinations thereof.

The histotripsy immunosensitization techniques described above can be used to create a form of in situ cancer vaccine by liquefying resected tumor tissue and mechanically disrupting the tumor cells to release potential tumor antigens. In some embodiments, histotripsy systems may be configured for laboratory and/or bench use, for the purpose of creating tumor lysates and/or vaccines. For patients who undergo surgery to remove a primary focal tumor, histotripsy can be used to ablate a portion of the resected tumor in vitro. The ablated resected tumor can be examined by centrifugation and microscopic evaluation to confirm that the tumor was sufficiently broken down to acellular debris. The acellular debris can be harvested and used to create injectable tumor-specific vaccines. The administration of histotripsy generated cancer vaccines generated in this manner can be capable of significantly reducing tumor growth compared with non-vaccinated controls.

Figure 5:
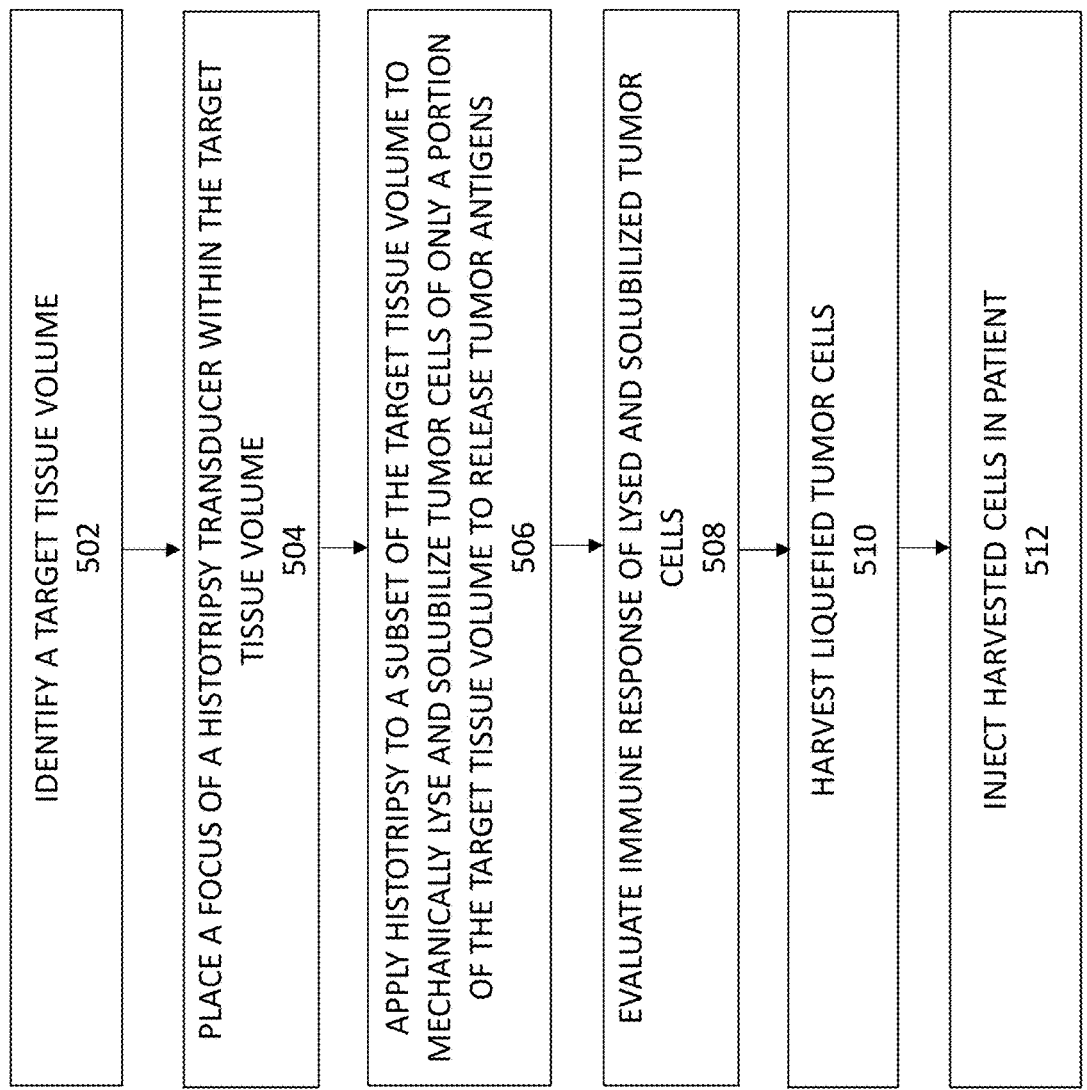
FIG. 5 is a flowchart that describes a method for creating cancer vaccines with histotripsy therapy.

Referring to flowchart 500 of FIG. 5, a method of creating a cancer vaccine is described. At step 502 of flowchart 500, the method can include identifying at least one target tissue volume. Step 502 can include identifying the precise location of the target tissue volume within the body of the patient, including identifying details about the size, shape, volume, mass, and tissue type(s) of the target tissue volume. For example, the identifying step can include identifying the type of volume (e.g., tumor), the type of tissue or organ within which the volume is located, and the volume or mass of the target volume itself. In some implementations, identifying the at least one target tissue volume can be achieved with a medical imaging modality such as ultrasound, MRI, CT, or the like.

The target tissue volume can comprise tumors or other abnormal tissue volumes within a liver, a kidney, a spleen, a pancreas, a colorectal, a bowel, a stomach, an esophagus, a breast, a lung, a head, a neck, a thyroid, skin, nervous tissue, hematological malignancies, a sarcoma, primary and metastatic lesions, and brain tissue.

In some examples, identifying the target tissue volume can further include determining a treatment volume of the target tumor to ablate so as to maximize the cell response of releasing tumor antigens. For example, if the chosen treatment volume is too small, the stimulated immune response will be insufficient. Conversely, if the ablation volume is too large, treatment-related clinical complications could ensue and/or the immune response may be sub-optimal. Determining treatment volume can be critical for the purpose of immune stimulation, such that sufficient immune stimulation is achieved without significant complications. In some examples, ablation of sufficient number of cells typically comprises ablation of >1 mL tissue or >10% of the target tumor. In another embodiment, the treatment volume of the at least one target tumor ranges from 25% to 90% of a volume of the at least one target tumor. In another implementation, the treatment volume of the at least one target tumor is at least 1 cm$^3$ in volume. The extent of immune stimulation by histotripsy may be impacted by ablation volume (20% vs. 80% vs. 100%; 1 mL vs. 20 mL vs. 60 mL) and can also be impacted by the type of cancer or the location of the target tumor region. For example, the location of the target tissue volume or the target tumor type can be used to determine the optimal treatment volume.

In other embodiments, identifying the target tissue volume can further include determining a treatment location to increase, enhance, and/or maximize the cell response of releasing tumor antigens. For example, in some embodiments, the treatment location comprises only a central/inner portion of the at least one target tumor. In other embodiments, the treatment location comprises only a periphery of the at least one target tumor. In another implementation, the treatment location comprises a plurality of programmed treatment locations distributed spatially through the at least one target tumor. It is possible that the extent of immune stimulation by histotripsy may be impacted by the pattern of ablation (e.g., ablation of the inner core/central portion vs. outer rim/periphery only; contiguous ablation vs. checkerboard pattern). For example, a checkerboard ablation pattern may allow more vascular access to the ablated acellular debris, which may increase the magnitude of the stimulated immune response as compared to a contiguous pattern of ablation. The treatment location chosen at step 206 can depend on the type of tissue to be treated, including the tumor type/cancer type, the surrounding tissues, the size and or shape of the target tumor, etc.

In some embodiments, identifying the target tissue volume further comprises identifying a first target tissue volume and a second target tissue volume. In some embodiments, the first and second target tissue volumes are located in the same organ or anatomical location. In other embodiments, the first and second target tissue volumes are located in different organs or anatomical locations.

In some embodiments, a target tumor volume can be surgically resected from a patient. In other examples, some or all of the target tissue volume is resected. Furthermore, one or more target tissue volumes can be resected in a single surgical procedure. It is possible to ablate the tumor samples extracted via biopsy. While the tumor can be resected from the patient, in other embodiments, it is possible to use histotripsy to ablate the tumor tissue in situ into liquefied acellular debris inside the patient, and then extract the liquefied cells out via a catheter to use as a histotripsy cancer vaccine, as described below. In some cases and as previously mentioned, such lysates may be banked/stored for later use, including in chronic disease management or during disease stage progression (e.g., banked at time of curative surgery and to be used later if/when recurrence or progression occurs).

At step 504 of flowchart 500, the method can include placing a focus of a histotripsy therapy transducer within the target tissue volume. In some examples, placing the focus can comprise placing the focus with a robotic positioning system. For example, a histotripsy therapy transducer can be positioned on a robotic arm of the robotic positioning system, and the robotic positioning system can use real-time feedback to place the focus within the target tissue volume, or alternatively, the robotic positioning system can use knowledge of the focal distance of the transducer to accurately place the focus at the desired position within tissue. in some embodiments, the robotic positioning system comprises a robotic arm with a minimum of 3 degrees of freedom. In other embodiments, the robotic positioning system comprises a robotic arm that directs a histotripsy therapy transducer through a pre-programmed three-dimensional treatment routine.

At step 506 of flowchart 500, the histotripsy therapy transducer can apply histotripsy therapy to a subset of the target tissue volume to mechanically lyse, solubilize, and/or liquefy tumor cells of only a portion of the target tissue volume to release tumor antigens. The histotripsy therapy is applied so as to disrupt the tumor cell membranes without generating adequate heating in the target tissue volume to cause protein denaturation. To achieve this goal, the histotripsy immunosensitization therapy described in step 506 may be carried out in one or more sessions, over which an optimal volume is ablated during each session.

As described above, histotripsy therapy creates cavitation in a target tissue volume with by applying histotripsy pulses to the histotripsy therapy transducer that have microsecond pulse lengths (<20 us), high peak negative pressure (>10 MPa), and a low duty cycle (<5%), to mechanically lyse, solubilize, and/or liquefy the target tumor volume and to disrupt the tumor cell membrane, while avoiding tissue heating.

In another example, our preliminary data shows that histotripsy monotherapy of one tumor site results in significant reduction in the number and volume of distant untreated tumor site, including metastases (abscopal effect). This includes therapeutic response locally, regionally (draining lymphatic) and systemically (circulation). Thus, the method provided herein can be used not only to treat the ablated tumor volume, but also tumor/cancer volumes that are separate from or apart from the targeted tumor volume. As a further example, one of a plethora of colorectal metastases may be treated in the liver, with an observed therapeutic response seen in the stabilization or reduction in tumor burden of other non-treated tumors (and of non-liver origin).

To control the ablation of specific volume, shape, and patter, histotripsy delivery can be assisted by the robotic arm and/or navigation system described above, which can be used to mechanically move the histotripsy transducer, such that the histotripsy focus will be scanned to cover the planned tumor volume, with specific volume, shape, and pattern. Furthermore, the system can be configured to control the ablation of specific volume, shape, and pattern, histotripsy delivery by electronic focal steering using a 2D phased array ultrasound transducer, which can be used to electronically move the histotripsy transducer, such that the histotripsy focus will be scanned to cover the planned tumor volume, with specific volume, shape, and pattern.

In some embodiments, the histotripsy can be applied to only a subset of the target tissue volume. For example, the histotripsy can be applied only to a subset of the target tissue volume that comprises approximately 25% to 90% of the target tissue volume. Alternatively, the subset can comprise at least 1 cm³ in volume. In some embodiments, the subset comprises only a central portion of the target tissue volume. Alternatively, the subset can include only a periphery or peripheral/outer portion of the target tissue volume. In one implementation, the applying histotripsy to the subset of the target tissue volume further comprises applying histotripsy to a plurality of programmed treatment locations distributed spatially through the target tissue volume.

As described above, histotripsy targeting and delivery to the target tumor can be guided by real-time imaging, e.g., ultrasound imaging, CT, or MRI. The imaging feedback can confirm that histotripsy is used to treat the planned tumor volume of a specific volume, shape, and pattern.

At step 508 of flowchart 500, the method can further include evaluating the immune response and therapeutic effect after delivery of histotripsy therapy to the target tumor location. Evaluating the immune response can allow time for the lysed, solubilized, and or liquefied acellular debris produced by histotripsy to stimulate adaptive immune responses in tumor draining lymph nodes and within the systemic circulation, and can allow time to cause inflammation and DAMP release. These changes are expected to lead to regional and systemic tumor-specific immune responses. The evaluation step can include assessment of immunological cell death and/or immune activation.

The evaluating step can comprise imaging the cell response, the imaging comprising ultrasound, CT, MRI, and/or PET imaging. In some embodiments, evaluating the immune response comprises imaging the at least one target tumor and/or performing a tissue biopsy on the at least one target tumor. The stimulated immune response can be evaluated with blood tests, and abscopal effects on distant tumor sites can be evaluated with non-invasive imaging following histotripsy immunosensitization. In some examples, evaluating the immune response comprises evaluating the immune response in one or more organs or anatomical locations. In other embodiments, evaluating the immune response includes biomarker analyses of tissue, cells, blood and/or combinations thereof. In some examples, the evaluation can takes 1-10 days to stimulate sufficient immune response. In other embodiments, the evaluation can occur weeks to months after delivering histotripsy therapy.

At step 510 of flowchart 500, if sufficient cellular response is observed, the liquefied and solubilized tumor cells can be harvested from the target tissue volume. Finally, at step 512 of flowchart 500, the harvested cells can be injected into a patient. In some embodiments, the patient can be the same patient from which the tumor was originally resected. In other embodiments, the harvested cells can be injected into other patients in the form of a cancer vaccine.

In some embodiments, a targeted cancer vaccine can be created from the components of the harvested cells. The histotripsy cancer vaccines described herein are most effective for the patient, from who the tumor tissue is extracted to make the vaccine, as the histotripsy cancer vaccine carries the specific tumor antigens for that patient.

The immunoprotective effect of histotripsy cancer vaccines may be potentiated by the use of immune adjuvants or dendritic cell vehicles. Histotripsy cancer vaccines as described herein may be frozen for future use. The availability of personalized tumor-specific vaccines derived from patient tumors may allow for future administration in the event of tumor recurrence. Histopsy cancer vaccines have the potential to reduce growth of existing tumors, or protect against the growth of future recurrent tumors.

A sufficient volume of the resected tumor needs to be ablated by histotripsy to get an adequate histotripsy cancer vaccine dose for therapeutic effect. The acellular nature of histotripsy cancer vaccines may enable their use in other patients with the same tumor type. The efficacy of histotripsy cancer vaccines may be enhanced through the use of multiple administrations (boosters). Furthermore, the efficacy of histotripsy cancer vaccines may be enhanced by encapsulated the acellular histotripsy cancer vaccine in nanoparticles.

Figure 6:
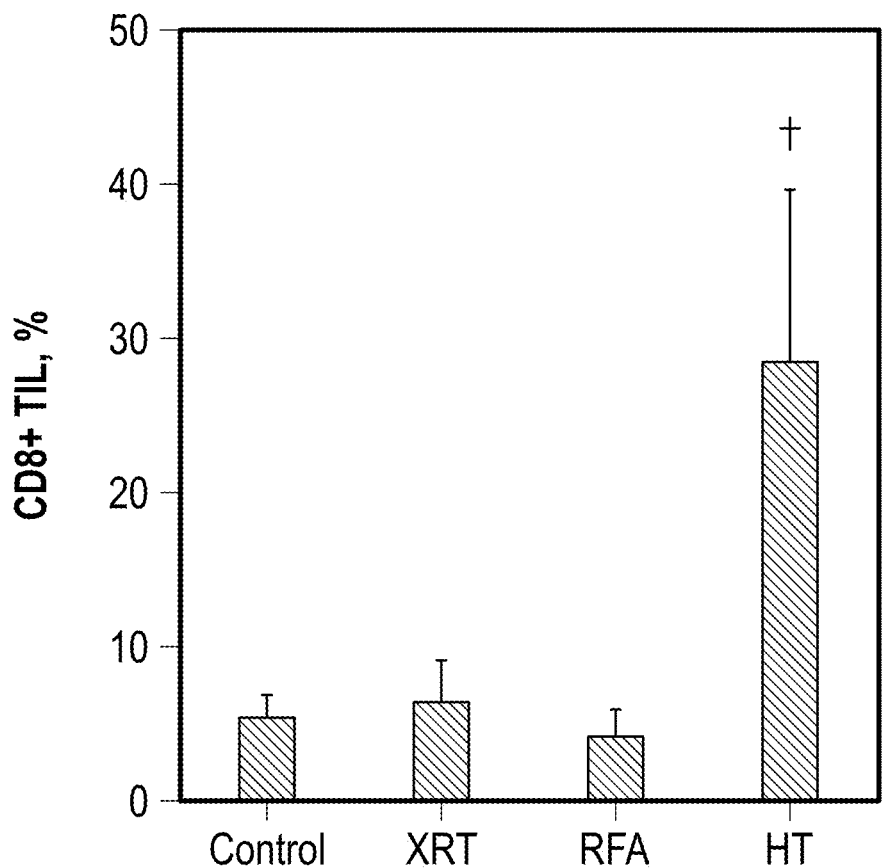
FIG. 6 illustrates the results of one experiments that establish the efficacy of histotripsy in inducing the release of cancer antigens and the efficacy of cancer vaccines formed with histotripsy therapy.

Proof of Concept. Histotripsy stimulates potent immune responses within the tumor as well as within regional and systemic lymphoid compartments. FIG. 6 illustrates experiments that have been performed to prove that histotripsy stimulates abscopal immune responses. Referring to FIG. 6, C57BL/6 mice inoculated with B16GP33 tumors 47-49 received no treatment (control), radiation (XRT), radiofrequency ablation (RFA), or histotripsy on day 10. Flow cytometric (FACS) analysis of TIL on day 21 demonstrated no measurable increases in CD8+ T cell infiltration following XRT or RFA; in contrast, histotripsy stimulated significant intratumoral CD8+ T cell infiltration.

Figure 7B:
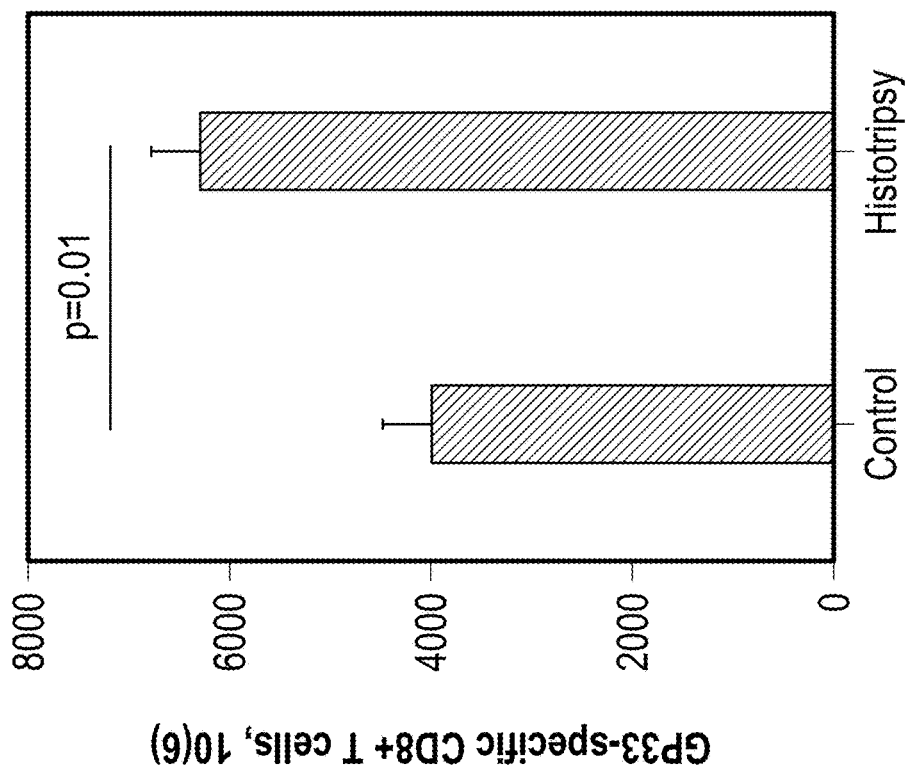
FIGS. 7A and 7B illustrate how histotripsy ablation stimulates regional and systemic tumor-specific CD8+ T cell responses.
Figure 7A:
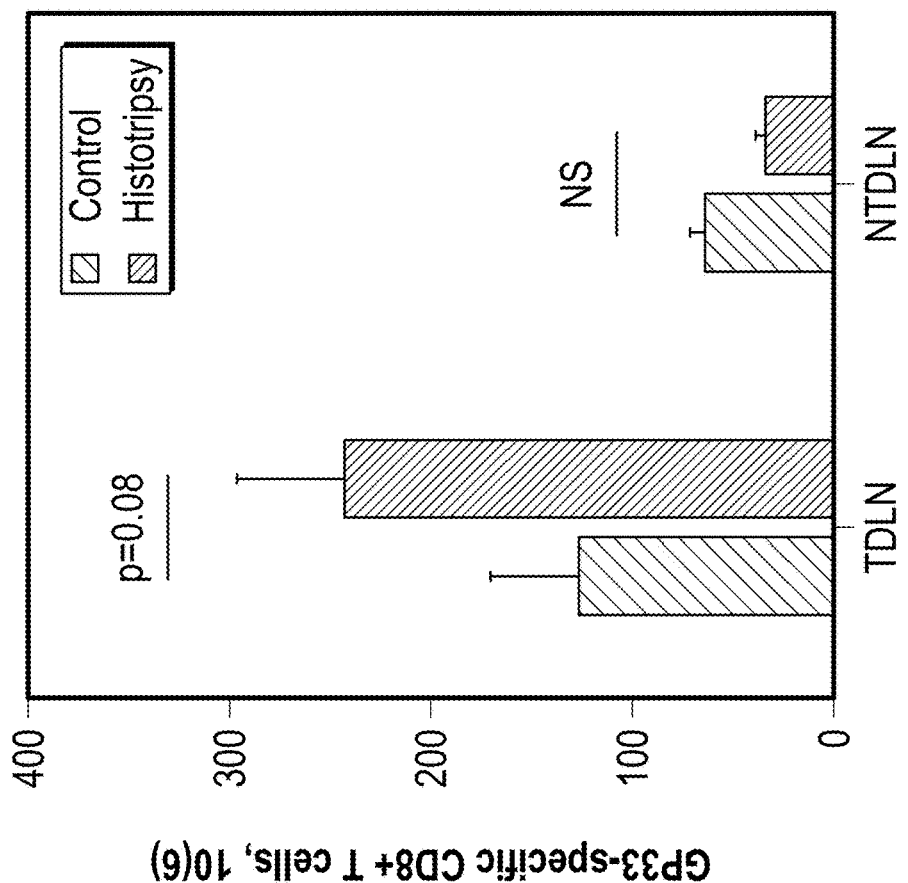

FIGS. 7A and 7B illustrate how histotripsy ablation stimulates regional and systemic tumor-specific CD8+ T cell responses. In this experiment, mice were inoculated with B16GP33 melanoma tumors, then treated with or without roughly 80% histotripsy ablation on day 9. Tumor draining lymph nodes (TDLN), contralateral axillary non-tumor-draining lymph nodes (NTDLN), and splenocytes (SC) were harvested on day 20. FACS analysis of ipsilateral tumor-draining lymph nodes (TDLN), contralateral axillary non-tumor-draining lymph nodes (NTDLN) and splenocytes (SC) on day 20 identified more CD8+ T cells in both TDLN and SC in mice treated with histotripsy. FIG. 7A shows CD8+ T cells specific for the tumor neoantigen GP33 among TDLN, and FIG. 7B shows CD8+ T cells specific for the tumor neoantigen GP33 among SC.

Figure 8:
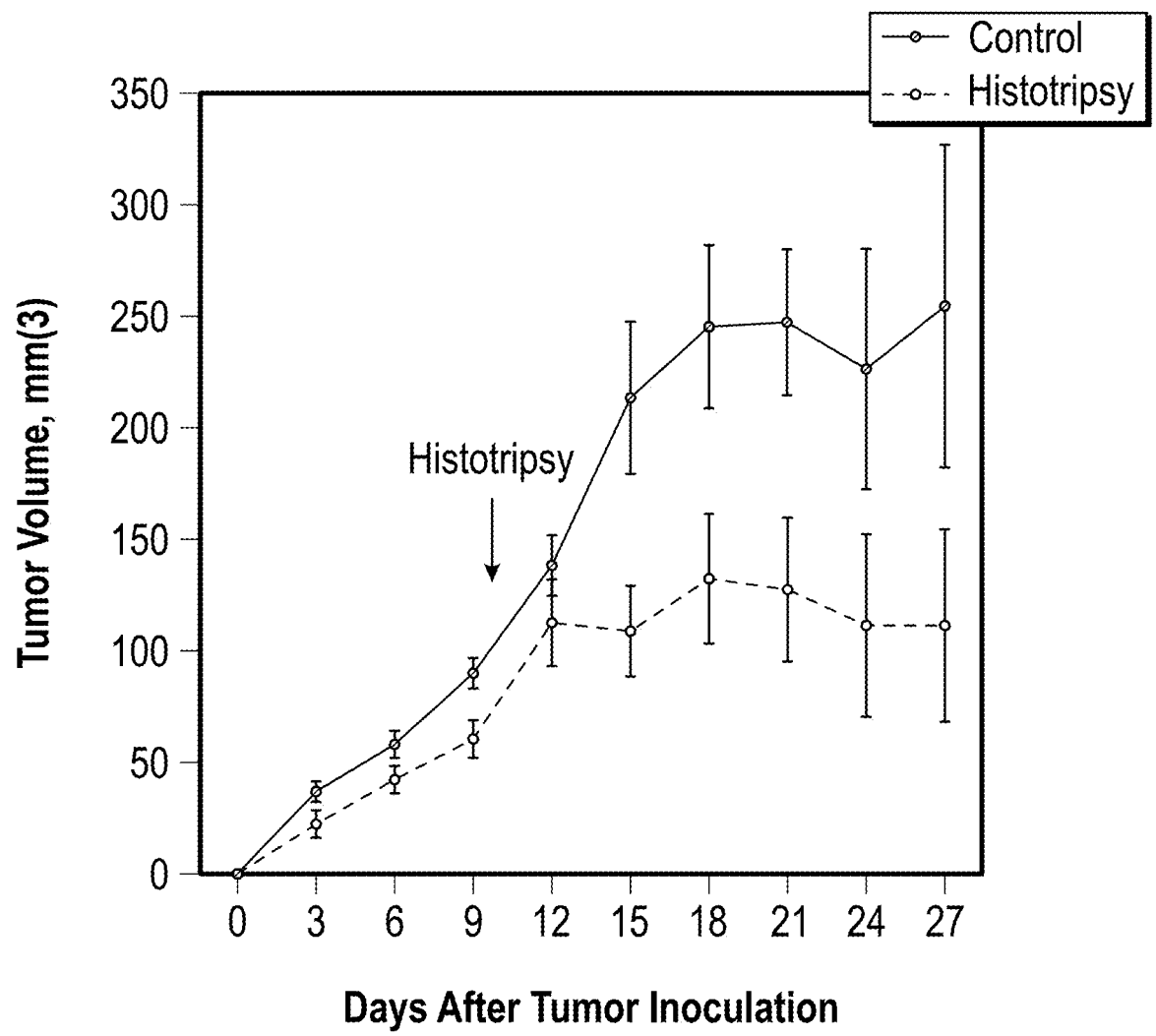
FIG. 8 shows another experiment in which histotripsy ablation of a flank tumor in mice resulted in significant reduction of a contralateral untreated tumor compared to a control case.

FIG. 8 shows another experiment in which histotripsy ablation of a flank tumor in mice resulted in significant reduction of a contralateral untreated tumor compared to a control case. C57BL/6 mice bearing bilateral flank Hepa1-6 hepatocellular carcinoma tumors underwent no treatment (control) or histotripsy of unilateral tumors on day 9. Histotripsy ablation of the flank tumor resulted in significant reduction of the contralateral, untreated tumor compared to the control cases.

Figure 9B:
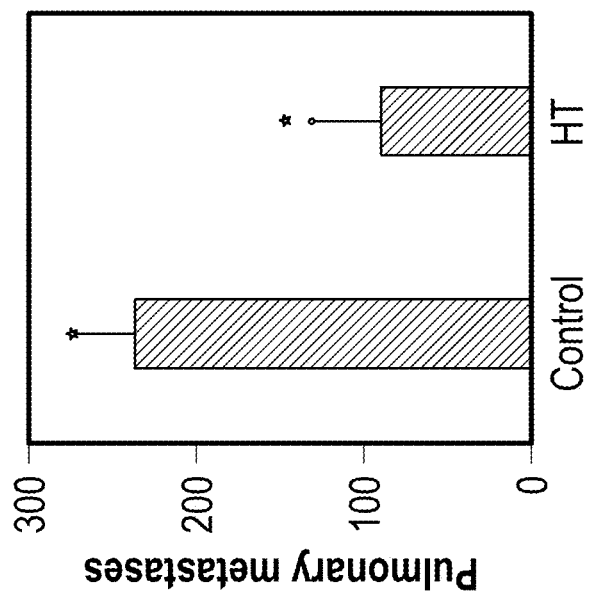
FIGS. 9A-9C illustrate additional experiments in which mice bearing unilateral B16GP33 flank tumors received intravenous injections of B16GP33 to establish pulmonary metastases.
Figure 9A:
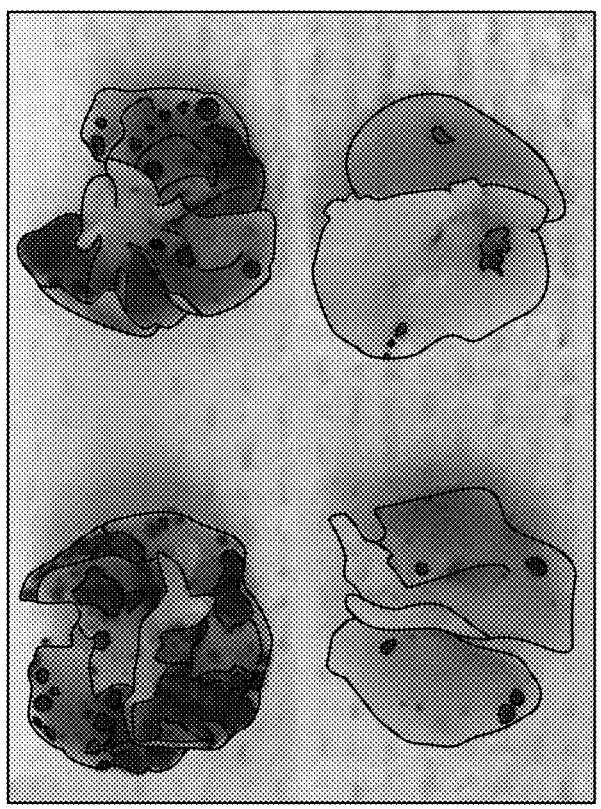
Figure 9C:
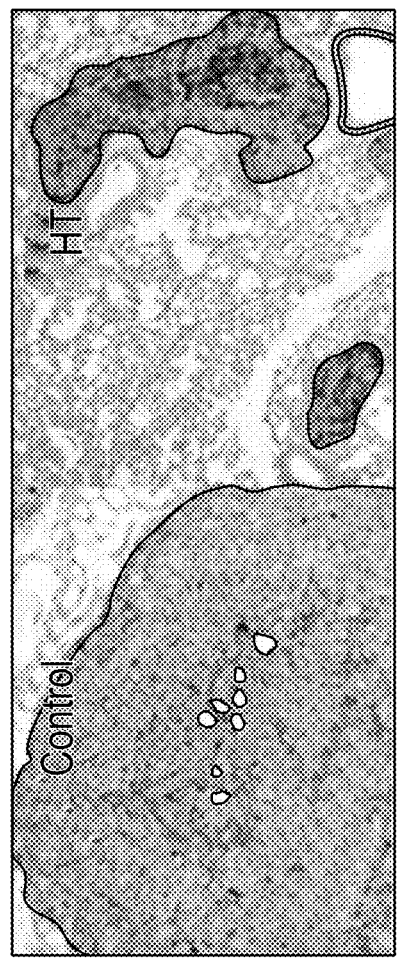

In parallel experiments, referring to FIGS. 9A-9C, mice bearing unilateral B16GP33 flank tumors received intravenous injections of B16GP33 to establish pulmonary metastases. Histotripsy ablation of flank tumors (on day 9 after injection) significantly decreased the number and volume of pulmonary metastases compared to untreated controls (see FIGS. 9A-9B). Immunohistochemistry of the pulmonary metastases, as shown in FIG. 9C, shows dense abscopal CD8+ T cell infiltration with histotripsy. This abscopal immunostimulation demonstrates the therapeutic potential of histotripsy immunosensitization.

Figure 10C:
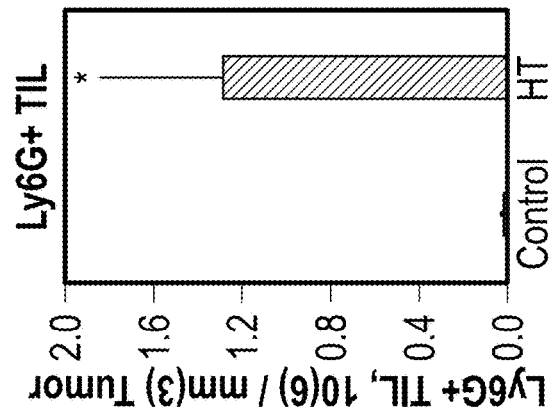
FIGS. 10A-10E show histotripsy results in pro-inflammatory changes within the tumor microenvironment.
Figure 10B:
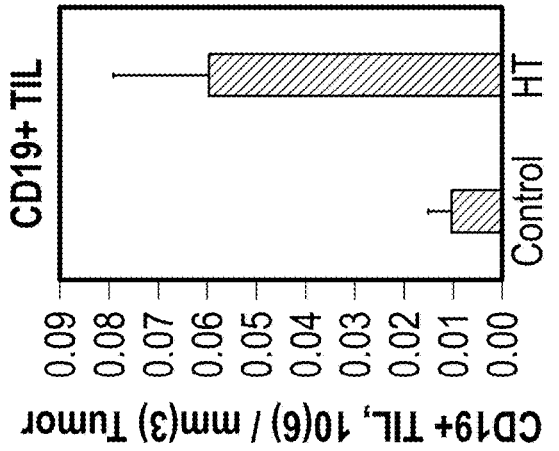
Figure 10E:
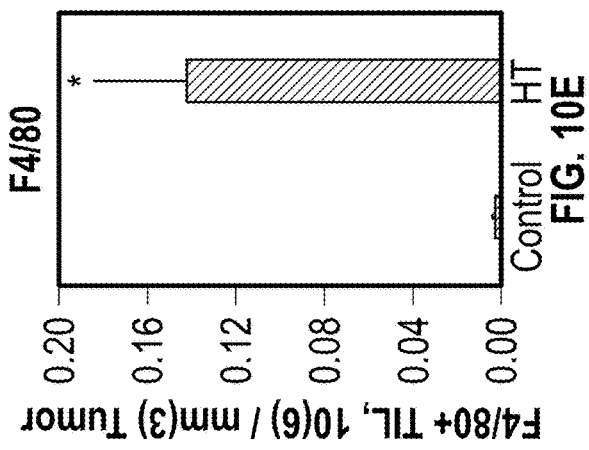
Figure 10A:
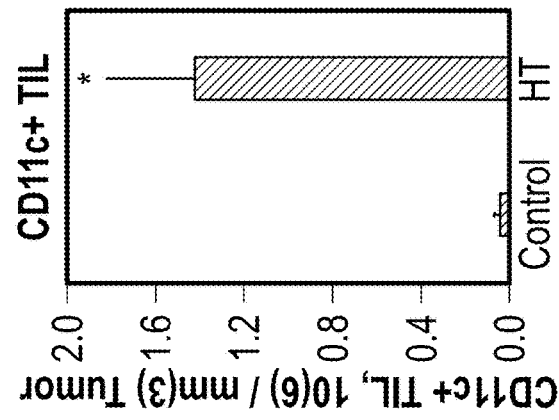
Figure 10D:
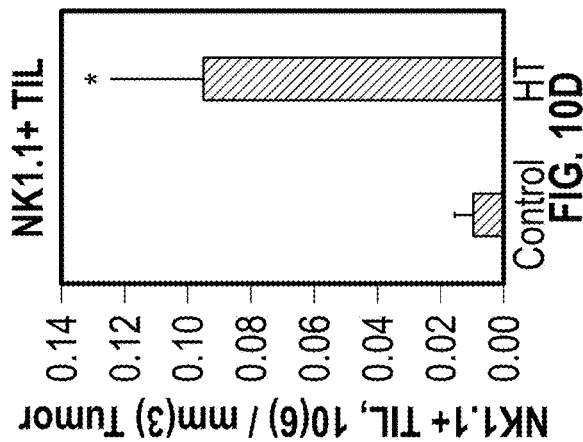

FIGS. 10A-10E show histotripsy results in pro-inflammatory changes within the tumor microenvironment. C57BL/6 mice bearing B16GP33 flank tumors were treated with histotripsy ablation. FACS analysis of tumor-infiltrating cell populations identified significant upregulation of various non-T cell adaptive and innate immune populations indicative of marked pro-inflammatory changes within the tumor microenvironment. FIG. 10A shows larger numbers of dendritic cells, FIG. 10B shows larger numbers of B cells, FIG. 10C shows larger numbers of neutrophils, FIG. 10D shows larger numbers of natural killer cells, and FIG. 10E shows larger numbers of macrophages after histotripsy. Therefore, histotripsy induces a pro-inflammatory state that can support tumor ICD.

Physiological stress and histotripsy induce the release of HMGB1 from cancer cells. HMGB1 is constitutively expressed by Hepa1-6.50-5650-5253, 55, 5653, 55, 5653, 55, 56. Three and ten days after histotripsy, immunofluorescence studies identified increased levels of extranuclear HMGB1 in B16GP33 tumors treated with histotripsy. Ten days after histotripsy, ELISA studies identified increased levels of HMGB1 in the serum. These findings suggest that histotripsy is capable of promoting ICD through the potent release of intratumoral DAMPs.

Figure 11:
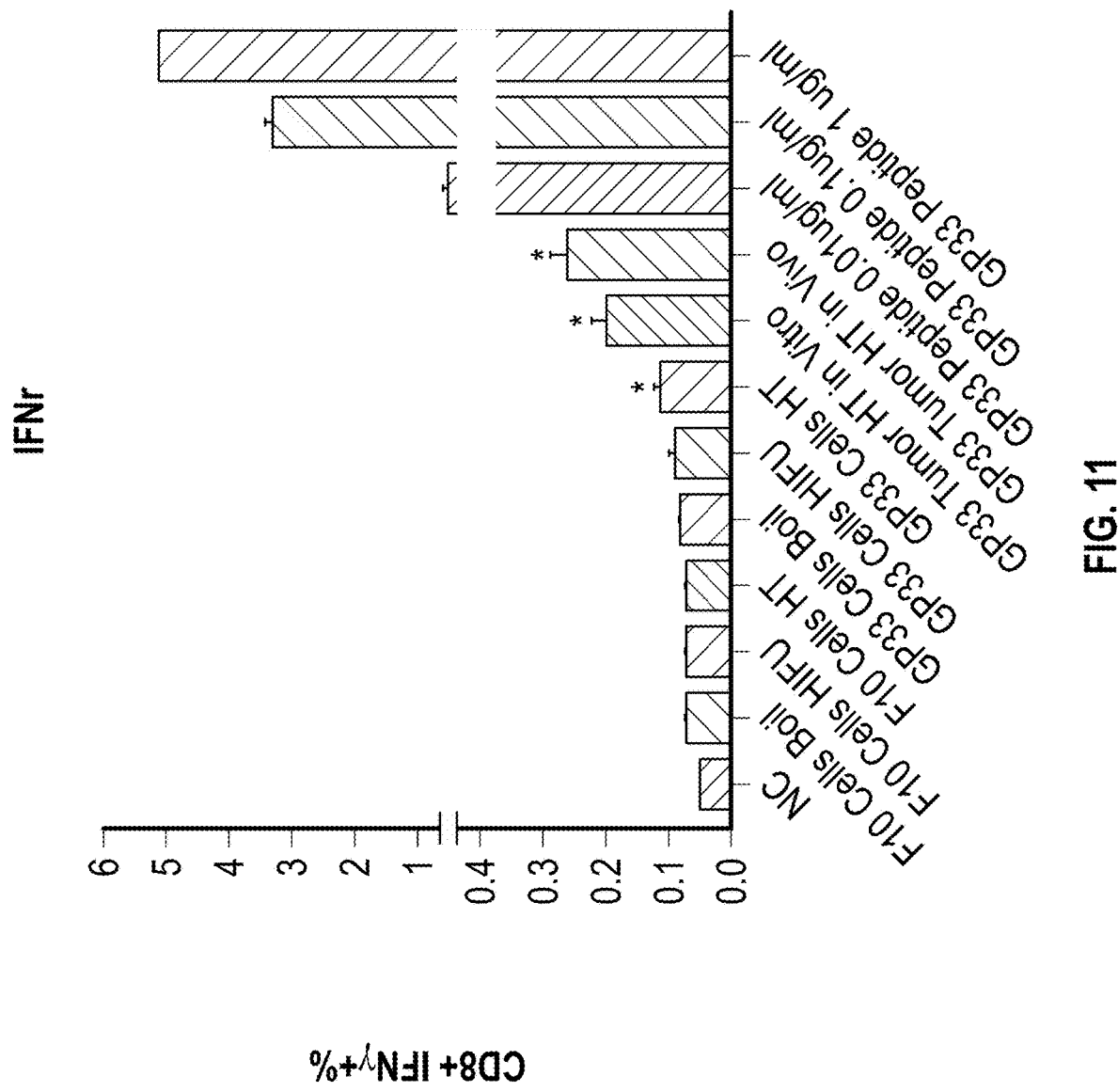
FIG. 11 shows the results of an experiment in which histotripsy causes immunogenic neoantigens to be released from treated tumors.

Histotripsy releases immunogenic peptides from the tumor. B16GP33 or B16F10 melanoma tumors were expanded or inoculated into C57BL/6 mice. Melanoma cells were centrifuged into pellets and treated in vitro with boiling, HIFU, or histotripsy; alternatively, melanoma tumors were treated with HIFU or histotripsy in vivo, then excised and mechanically homogenized. GP33-specific CD8+ T cells were harvested from the spleens of C57BL/6 mice 8 days after LCMV infection, then exposed in vitro to B16F10 or B16GP33 cell lines or tumors treated with boiling, HIFU or histotripsy in the presence of IL-1. After five hours of stimulation, CD8+ T cells were collected and analyzed by flow cytometry for expression of IFN. As shown in FIG. 11, GP33-specific CD8+ T cells exhibited no IFN release in response to B16F10 cells or tumors treated with boiling, HIFU or histotripsy (negative control). Whereas B16GP33 cells or tumors treated with boiling or HIFU did not induce IFN expression, only B16GP33 cells or tumors treated with histotripsy stimulated GP33-specific CD8+ T cells. These methodologies show the ability of histotripsy to release immunogenically intact tumor neoantigen peptides mediates its immunostimulatory effects.

Figure 12:
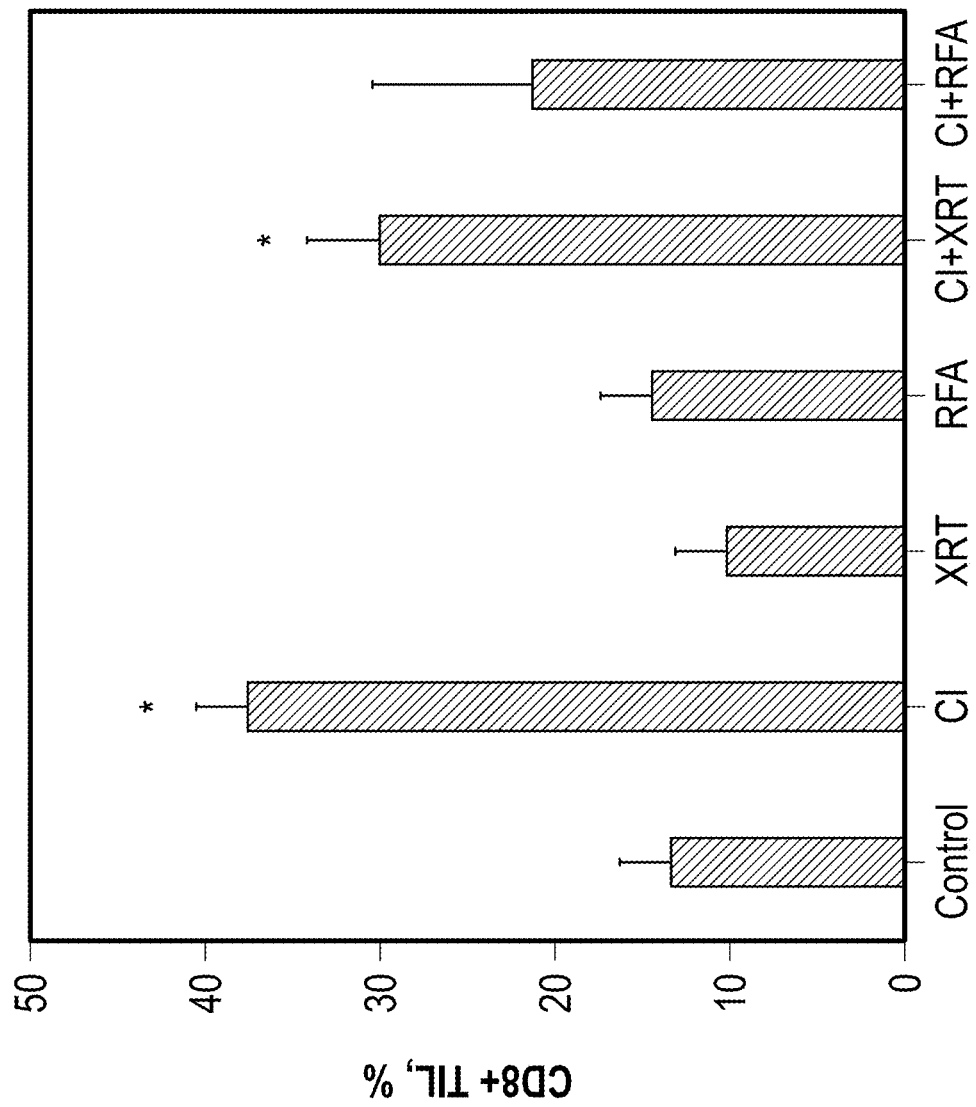
FIG. 12 shows an experiment in which checkpoint inhibition is not enhanced by radiation or thermal ablation.

FIG. 12 shows an experiment in which checkpoint inhibition is not enhanced by radiation or thermal ablation. XRT and RFA do not enhance CI immunotherapy. C57BL/6 mice bearing bilateral B16GP33 melanoma tumors were treated with no therapy (control), anti-CTLA-4 mAb on days 6, 9 and 12 (CI), XRT or RFA on day 10, or combination therapy (CI+XRT or CI+RFA) (FIG. 12). FACS analysis identified induction of local CD8+ TIL after CI, but not after XRT or RFA. Combination therapy did not increase CD8+ TIL beyond that with CI alone. We believe this absence of benefit is an opportunity for significant improvement.

FIGS. 13A-13C illustrate an experiment which shows that histotripsy enhances the efficacy of immunotherapy. Histotripsy improves CI immunotherapy in the flank Hepa1-6 tumor. C57BL/6 mice bearing bilateral flank B16GP33 melanoma tumors received no therapy (control), anti-CTLA-4 mAb (CI) on days 6, 9 and 12, histotripsy of unilateral tumors on day 10, or CI plus histotripsy. Histotripsy plus CI resulted in the best tumor inhibition, CD8+ TIL, and CD8+ T cells within TDLN. FIG. 13A shows how tumor growth of contralateral (untreated) tumors was inhibited after histotripsy therapy. FIG. 13B shows that histotripsy resulted in significant increases in CD8+ TIL, with optimal TIL populations seen after histotripsy. FIG. 13C shows that the presence of tumor-specific CD8+ T cell populations among TDLN was highest after histotripsy. These observations suggest that histotripsy can sensitize tumors to respond to immunotherapy.

Figure 14:
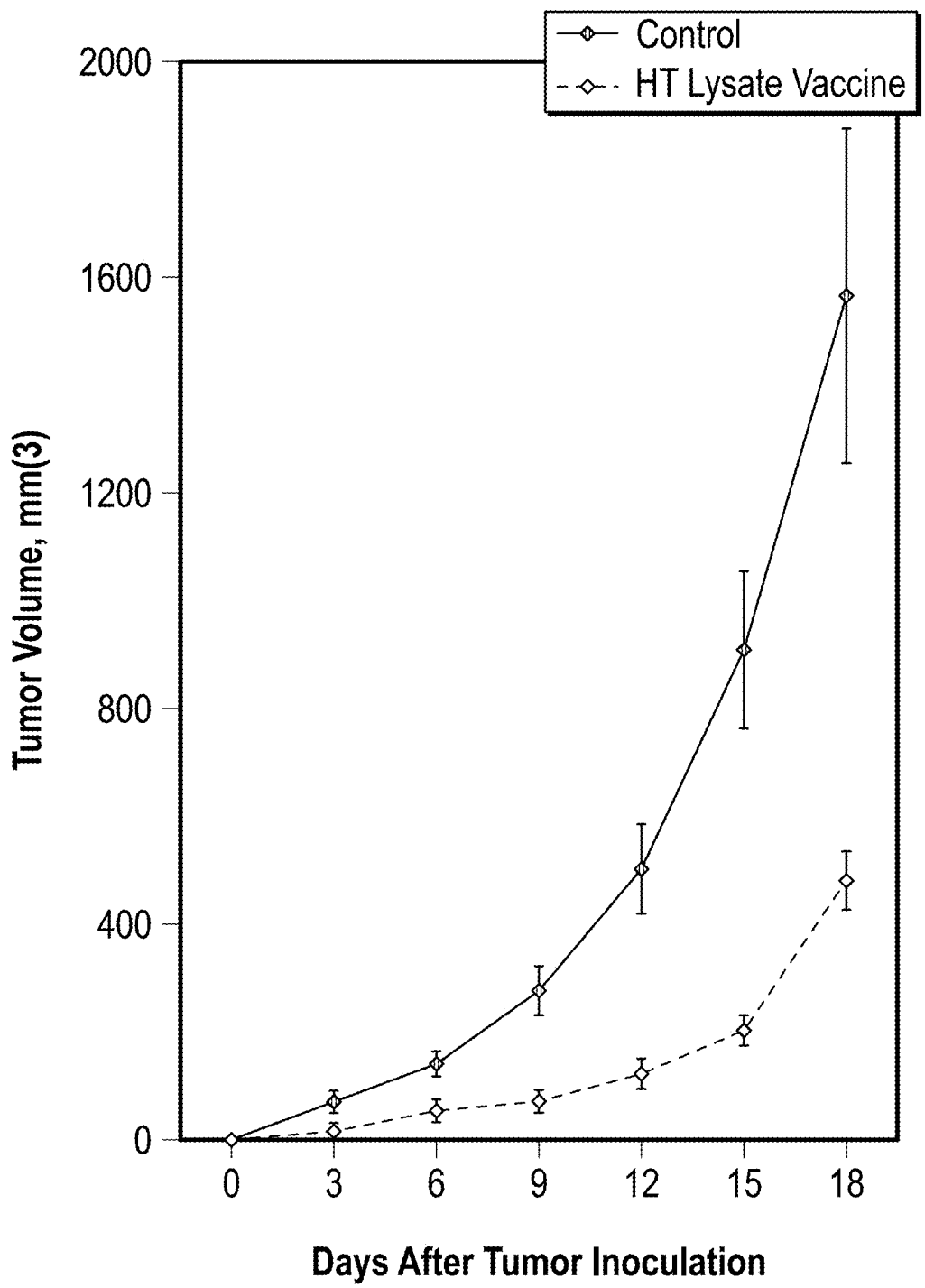
FIG. 14 is another experiment which shows that histotripsy-ablated tumors can function as immunoprotective cancer vaccines.

FIG. 14 is another experiment which shows that histotripsy-ablated tumors can function as immunoprotective cancer vaccines. C57BL/6 mice were inoculated with B16GP33 tumors. Tumors were treated with histotripsy ablation on day 10 and resected on day 13. After removing viable cells through centrifugation, the acellular lysate was injected intraperitoneally into mice 1 day prior to challenge with B16GP33 tumors. Mice treated with histotripsy cancer vaccines demonstrated significantly slower tumor growth compared with non-vaccinated controls (FIG. 14).

Thus, any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and/or methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the patient matter may be practiced. As mentioned, other embodiments may be utilized and derived there from, such that structural and logical substitutions and changes may be made without departing from the scope of this disclosure. Such embodiments of the inventive patient matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating tissue, comprising:
   identifying at least one target tumor;
   determining a treatment volume and a treatment location of the at least one target tumor that will increase a cell response of releasing tumor antigens; and
   applying histotripsy treatment based on the treatment volume and the treatment location to the at least one target tumor to mechanically lyse and solubilize tumor cells to release the tumor antigens.

2. The method of claim 1, wherein the cell response includes immunogenic cell death, infiltration of inflammatory and antigen presenting cells, infiltration and activation of T cells, increased tumor-specific T cells, infiltration of natural killer cells, B cells and CD4+ T cells, and/or depletion of immunosuppressive regulatory T cells and myeloid-derived suppressor cells.

3. The method of claim 1, wherein the treatment volume of the at least one target tumor ranges from 25% to 90% of a volume of the at least one target tumor.

4. The method of claim 3, wherein the treatment volume of the at least one target tumor is at least 1 cm³ in volume.

5. The method of claim 1, further comprising evaluating an immune response of the lysed and solubilized tumor cells.

6. The method of claim 5, wherein evaluating the immune response includes assessment of immunological cell death and/or immune activation.

7. The method of claim 5, wherein evaluating the immune response comprises imaging the at least one target tumor and/or performing a tissue biopsy on the at least one target tumor.

8. The method of claim 7, wherein the imaging comprises CT, MRI, and/or PET imaging.

9. The method of claim 7, wherein performing the tissue biopsy comprises performing a liquid biopsy.

10. The method of claim 1, further comprising applying immune therapy after applying the histotripsy treatment.

11. The method of claim 10, wherein the immune therapy is selected from the group consisting of checkpoint inhibitors, immunostimulatory therapies, cancer vaccines, oncolytic viruses, neutralizing immune inhibitors, and activating cytokines.

12. The method of claim 11, wherein the checkpoint inhibitors include CTLA-4, LAG3, TIM3, and combinations thereof.

13. The method of claim 11, wherein the checkpoint inhibitors include PD-1 blockade, PD-L1 blockade, and combinations thereof.

14. The method of claim 1, further comprising harvesting the lysed and solubilized tumor cells.

15. The method of claim 14, further comprising:
preparing an immune directed therapy using the lysed and solubilized tumor cells; and
administering the immune directed therapy into a patient.

16. The method of claim 15, wherein administering the immune directed therapy is selected from the group consisting of oral administration, systemic infusion, loco-regional catheter-based infusion, intratumoral injection, loco-regional injection, subcutaneous injection, and combinations thereof.

17. The method of claim 15, wherein the immune directed therapy is a cell therapy.

18. The method of claim 1, wherein applying the histotripsy treatment is configured to elicit an immune response in at least one distant tumor of the same phenotype as the at least one target tumor.

19. The method of claim 18, wherein the at least one distant tumor is located in a different organ or anatomical location than the at least one target tumor.

20. The method of claim 1, wherein the at least one target tumor is located in the group consisting of a liver, a kidney, a spleen, a pancreas, a colorectal, a bowel, a stomach, an esophagus, a breast, a lung, a head, a neck, a thyroid, skin, nervous tissue, hematological malignancies, a sarcoma, primary and metastatic lesions, and brain tissue.

21. The method of claim 1, wherein the treatment location comprises only a central portion of the at least one target tumor.

22. The method of claim 1, wherein the treatment location comprises only a periphery of the at least one target tumor.

23. The method of claim 1, wherein the treatment location comprises a plurality of programmed treatment locations distributed spatially through the at least one target tumor.

24. A method of treating tissue previously treated with radiation therapy and/or resistant to the radiation therapy, comprising:
identifying at least one target tumor;
determining a treatment volume and a treatment location of the at least one target tumor that will increase cell response of releasing tumor antigens; and
applying histotripsy treatment to the at least one target tumor to mechanically lyse and solubilize tumor cells to release the tumor antigens.

25. A method of treating tissue previously treated with immunotherapy and non-responsive or resistant to immunotherapy, comprising:
identifying at least one target tumor;
determining a treatment volume and a treatment location of the at least one target tumor that will increase cell response of releasing tumor antigens; and
applying histotripsy treatment to the at least one target tumor to mechanically lyse and solubilize tumor cells to release the tumor antigens.

* * * * *